US012569449B1

(12) United States Patent
Zhang

(10) Patent No.: US 12,569,449 B1
(45) Date of Patent: Mar. 10, 2026

(54) CATIONIC LIPID COMPOUND, AND PREPARATION METHOD THEREFOR AND USE THEREOF

(71) Applicants: RONGCAN (SHANGHAI) BIOTECH CO., LTD, Shanghai (CN); SHANGHAI JIAO TONG UNIVERSITY, Shanghai (CN)

(72) Inventor: Xueqing Zhang, Shanghai (CN)

(73) Assignees: RONGCAN (SHANGHAI) BIOTECH CO., LTD, Shanghai (CN); SHANGHAI JIAO TONG UNIVERSITY, Shanghai (CN)

( * ) Notice: Subject to any disclaimer, the term of this patent is extended or adjusted under 35 U.S.C. 154(b) by 0 days.

(21) Appl. No.: 18/852,937

(22) PCT Filed: Mar. 30, 2023

(86) PCT No.: PCT/CN2023/085225
§ 371 (c)(1),
(2) Date: Apr. 22, 2025

(87) PCT Pub. No.: WO2023/186041
PCT Pub. Date: Oct. 5, 2023

(30) Foreign Application Priority Data

Mar. 31, 2022 (CN) ......................... 202210344395.1

(51) Int. Cl.

| | |
|---|---|
| ***A61K 9/51*** | (2006.01) |
| ***A61K 47/18*** | (2017.01) |
| ***A61K 48/00*** | (2006.01) |
| ***C07C 219/06*** | (2006.01) |
| ***C07C 219/20*** | (2006.01) |
| ***C07C 229/24*** | (2006.01) |
| ***C07C 229/30*** | (2006.01) |
| ***C07C 275/20*** | (2006.01) |
| ***C07C 335/10*** | (2006.01) |

(52) U.S. Cl.
CPC ............ *A61K 9/5123* (2013.01); *A61K 47/18* (2013.01); *A61K 48/0033* (2013.01); *C07C 219/06* (2013.01); *C07C 219/20* (2013.01); *C07C 229/24* (2013.01); *C07C 229/30* (2013.01); *C07C 275/20* (2013.01); *C07C 335/10* (2013.01)

(58) Field of Classification Search
None
See application file for complete search history.

(56) References Cited

U.S. PATENT DOCUMENTS

2016/0326090 A1 11/2016 Albrecht et al.

FOREIGN PATENT DOCUMENTS

| | | | |
|---|---|---|---|
| CN | 108368028 | A | 8/2018 |
| CN | 110520409 | A | 11/2019 |
| CN | 112979483 | A | 6/2021 |
| CN | 113018449 | A | 6/2021 |
| CN | 113402405 | A | 9/2021 |
| CN | 113993839 | A | 1/2022 |
| CN | 114890907 | A | 8/2022 |
| CN | 115710192 | A | 2/2023 |
| GB | 2052977 | A | 2/1981 |
| WO | 2020061367 | A1 | 3/2020 |
| WO | 2021142280 | A1 | 7/2021 |
| WO | 2022060871 | A1 | 3/2022 |

*Primary Examiner* — Brian J Davis
(74) *Attorney, Agent, or Firm* — NKL Law; Bin Lu; Allen Xue

(57) ABSTRACT

A cationic lipid compound, and a preparation method therefor and use thereof are provided. The cationic lipid compound features a hydroxyl group at the head part, and its overall structure resembles a cone with a small head and a large tail. The LNPs prepared using the cationic lipid compounds with the aforementioned optimal structure usually exhibit enhanced biocompatibility and higher in vivo mRNA transfection efficiency, achieving unexpected technical effects. The synthesis route of the cationic lipid compounds is straightforward and practicable, with inexpensive and readily available raw materials, facilitating industrial production. Furthermore, the LNPs produced from the cationic lipid compounds possess a stable nanostructure that can be stored at low temperatures for a long time, thereby prolonging the shelf life of the pharmaceutical products while reducing the transportation requirements.

12 Claims, 1 Drawing Sheet

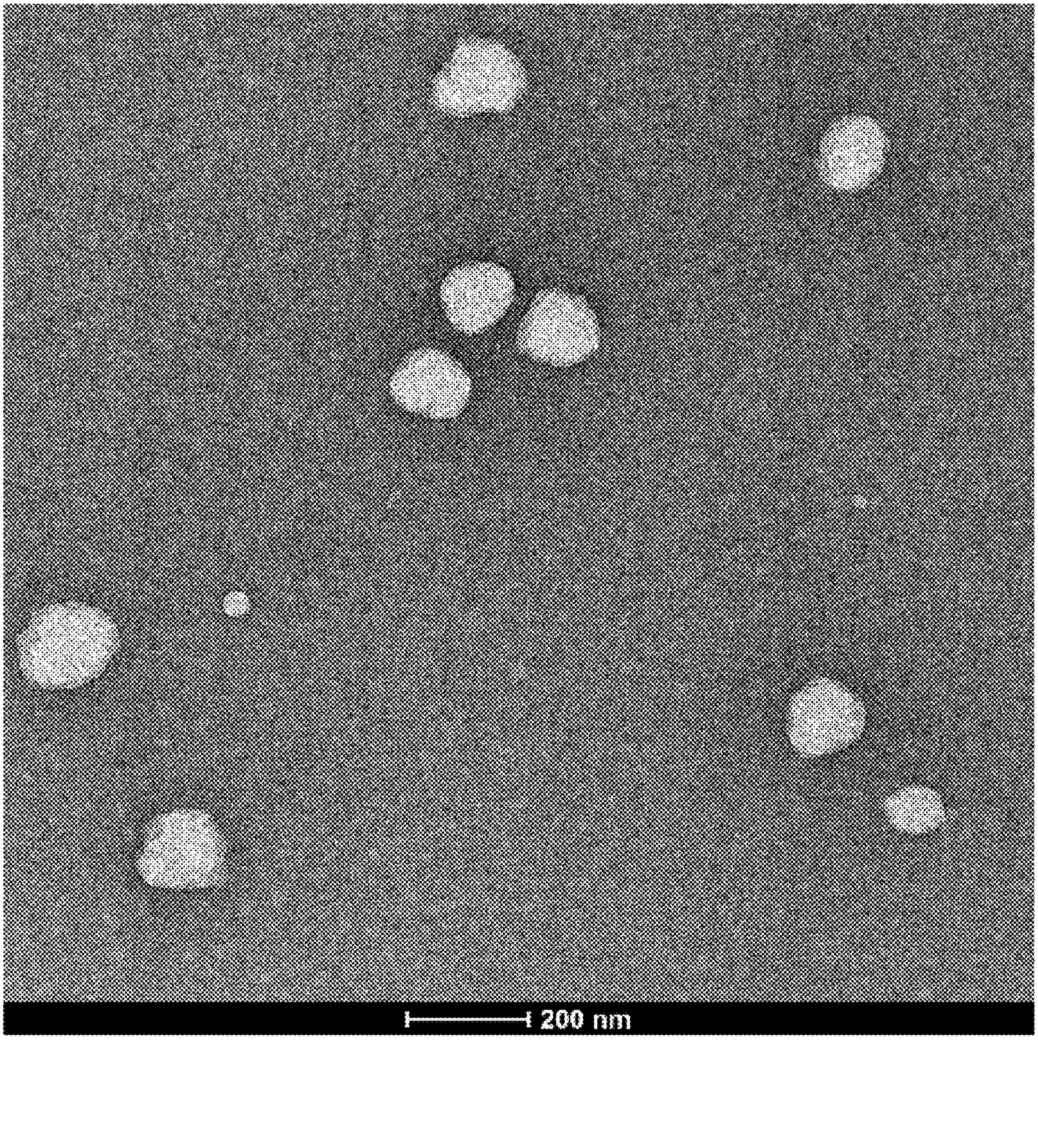
200 nm

CATIONIC LIPID COMPOUND, AND PREPARATION METHOD THEREFOR AND USE THEREOF

TECHNICAL FIELD

This invention relates to the field of biomedicine, particularly a cationic lipid compound, and preparation method therefor and use thereof.

BACKGROUND

Gene therapy is a treatment method that aims to correct or compensate for diseases caused by defective or abnormal genes by introducing exogenous genes into target cells. Nucleic acid vaccines, also known as genetic vaccines, refer to the encoding immunogenic protein or peptide nucleic acid sequence (such as DNA, mRNA, etc.) into the host. These sequences are then expressed by the host cells, resulting in the production of immunogenic proteins or polypeptides, inducing host cells to produce immune response to the immunogen, in order to achieve the purpose of prevention and treatment of diseases. The success of both gene therapy and genetic vaccines heavily relies on the effective delivery of exogenous genes. Among various methods for gene delivery, the development of suitable lipid nanoparticles (LNPs) for encapsulating nucleic acids, targeting them to the desired cells, and delivering specific genes into the cells has gradually been adopted by scientists.

An obvious difference between nucleic acid drugs and traditional chemical drugs is that the nucleic acid drugs have a large number of phosphate groups, resulting in a negative charge and a high molecular weight. In order to enable their better encapsulation by LNPs, various lipid compounds such as ionizable lipids have been developed.

LNP is a class of nanoparticle formed by lipid compounds, exhibiting a bilayer or multilayer membrane structure. The outer membrane is mainly composed of PEG lipids, or neutral lipids, while the inner membrane is mainly composed of neutral lipids, with some cholesterols serving as structural lipids. Neutral ionizable lipids, cationic lipid compounds, and the nucleic acids encapsulated in nanoparticles are distributed within the nanoparticles. “LNPs” refers to a nanostructure formed by encapsulating or associating therapeutic agents like nucleic acids with cationic lipid compounds. LNP and its compositions can be used for a diverse range of applications, including the in vitro and in vivo delivery of encapsulated or integrated (e.g., complexed) therapeutic agents, such as nucleic acids, into cells to induce the expression of target proteins or peptides or to inhibit the expression of target genes.

“Cationic lipid compounds” refers to a class of lipids capable of carrying positive charge. Exemplary cationic lipids comprise one or more positively charged amine groups. The preferred cationic lipids are ionizable and can exist in a positively charged state or neutral stats depending on the pH value. The physicochemical properties alter the surface charge of LNPs under different pH conditions. This charge state significantly influences immune recognition, blood clearance, distribution in the blood and tissue, and the ability to escape from endosomes within cells. These factors are crucial for intracellular delivery of nucleic acids.

In order to generate the desired therapeutic effect and/or trigger the desired immune response in biological systems, there are still many challenges in the development of nucleic acid-based therapeutics. Firstly, nucleic acid molecules are easily degraded by nucleases existing in vivo and in vitro.

Secondly, the ability of nucleic acid molecules to enter cells, interact with target organelles, and regulate the expression of target genes or proteins is limited. LNPs formed by cationic lipids and other lipid components (such as helper lipids, cholesterols, and PEGylated lipids) and nucleic acids have the ability to protect nucleic acids from degradation and promote cellular uptake of nucleic acids. An mRNA-LNP with excellent biocompatibility, superior mRNA in vivo transfection efficiency, high stability, and elevated biosafety is needed. Such LNPs are designed for various unmet clinical needs, can be applied to diverse application scenarios and purposes (cell therapy, gene editing, targeting technologies, etc.) through various administration routes (such as intramuscular injection, subcutaneous injection, intravenous injection, local injection, inhalation, and transdermal delivery, etc.). The LNPs described in this invention provide safe and effective delivery vehicles for the development of nucleic acid therapeutics or vaccines to treat a wide range of diseases (including metabolic disorders, respiratory illnesses, cardiovascular diseases, and tumors, etc.).

SUMMARY OF THE INVENTION

In order to solve the limitations of the prior art, the objective described in this invention is to provide a new class of cationic lipid compounds, preparation method therefor and use thereof. The mRNA-LNPs prepared using these novel cationic lipid compounds described in this invention exhibit excellent biocompatibility, superior mRNA in vivo transfection efficiency, high stability, and elevated biosafety.

In order to achieve the aforementioned objectives, the technical solution described in this invention is as follows:

A cationic lipid compound having the following structure:

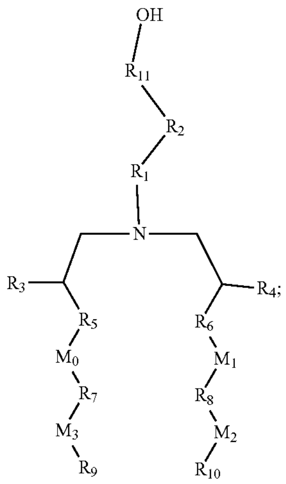

$R_1$ is

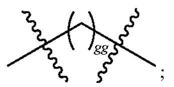

$gg = 0\text{-}10$ $R_2$ is
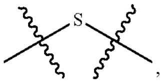
,
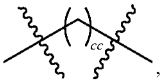
,
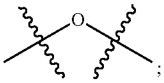
;
*cc* = 0-10
$R_3$ is H,
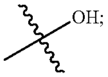 [SMILES: *O]
$R_4$ is H,
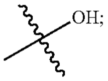 [SMILES: *O]
$R_5$ is
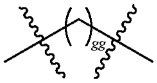
;
*gg* = 0-10
$R_6$ is
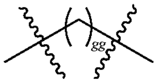
;
*gg* = 0-10
$R_7$ is
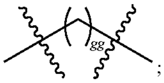
;
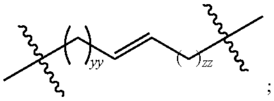
;
*gg* = 0-10
*yy* = 0-10
zz = 0-10
$R_8$ is
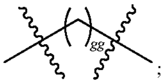
;
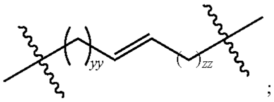
;
*gg* = 0-10
*yy* = 0-10
zz = 0-10
$R_9$ is
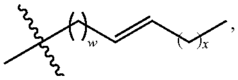
,
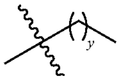
,
*w* = 0-10
*x* = 0-10
M = H, $CH_3$
*y* = 0-10
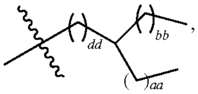
,
*aa* = 0-20
*bb* = 0-20
*dd* = 0-10
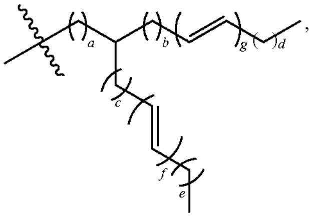
,
*a* = 0-10
*b* = 0-10
*g* = 0-1
*d* = 0-10
*e* = 0-10
*f* = 0-1
*c* = 0-10
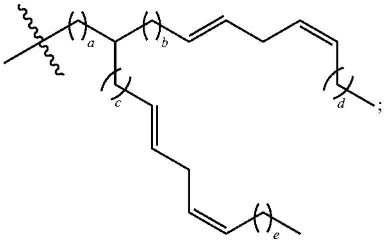
;
*a* = 0-10
*b* = 0-10
*c* = 0-10
*d* = 0-10
*e* = 0-10
$R_{10}$ is
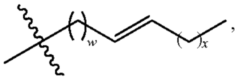
,
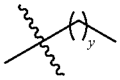
,
*w* = 0-10
*x* = 0-10
M = H, $CH_3$
*y* = 0-10
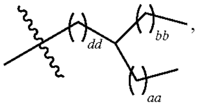
,
*aa* = 0-20
*bb* = 0-20
*dd* = 0-10
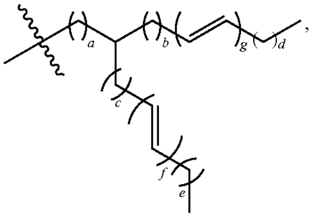
,
*a* = 0-10
*b* = 0-10
*g* = 0-1
*d* = 0-10
*e* = 0-10
*f* = 0-1
*c* = 0-10

-continued

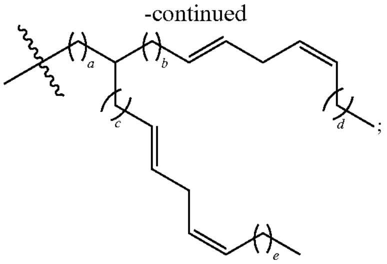;

*a* = 0-10
*b* = 0-10
*c* = 0-10
*d* = 0-10
*e* = 0-10

$R_{11}$ is

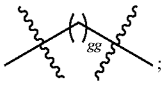;

*gg* = 0-10

$M_0$ and $M_1$ are:

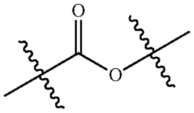, 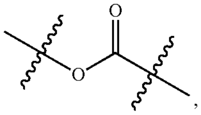,

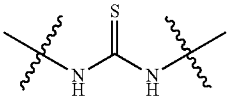, 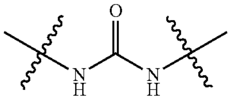,

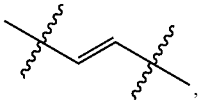, 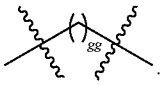.

*gg* = 0-10

$M_2$ and $M_3$ are:

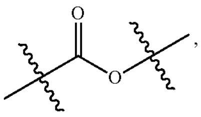, 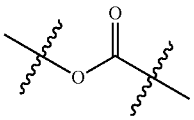,

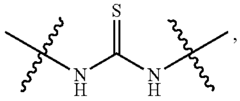, 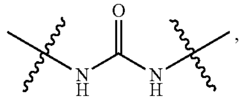,

*gg* = 0-10

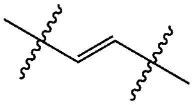, 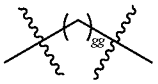.

The structure described in this invention introduces hydroxyl group at the head part, while the overall structure resembles a cone shape, featuring a small head and a large tail (which means that when the N atom is regarded as a center, the molecular structure space occupied by the head part with hydroxyl group is smaller than that of the tail part with alkane chain at the end). The structural optimization results in better biocompatibility and higher mRNA in vivo transfection efficiency of cationic lipid compounds.

The aforementioned cationic lipid compound, as a preferred embodiment, wherein at least two of $M_0$, $M_1$, $M_2$, and $M_3$ have ester bonds. Degradable ester bonds introduced at the hydrophobic tail part of lipid molecules can alter metabolic behavior of lipid molecules in vivo, thereby improving the biosafety of mRNA-LNPs.

The aforementioned cationic lipid compound, as an embodiment, wherein the cationic lipid compound is selected from the group consisting of:

H-1

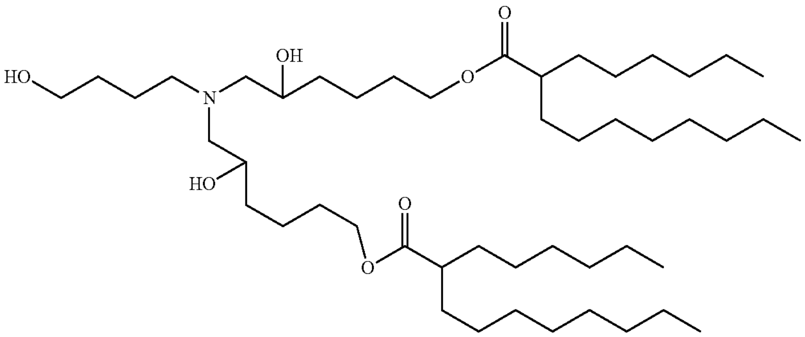,

-continued
H-3
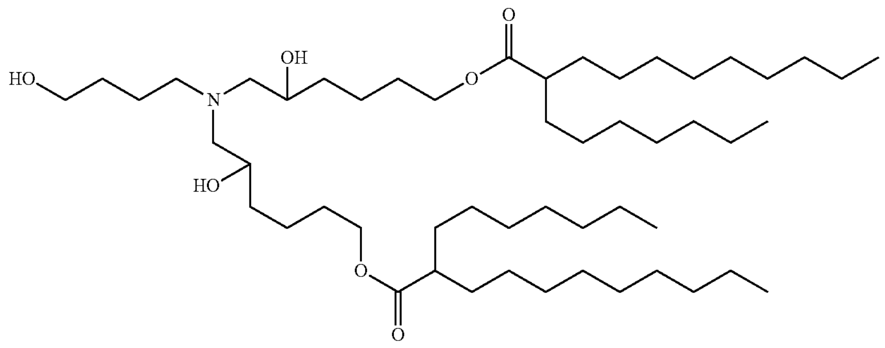
H-4
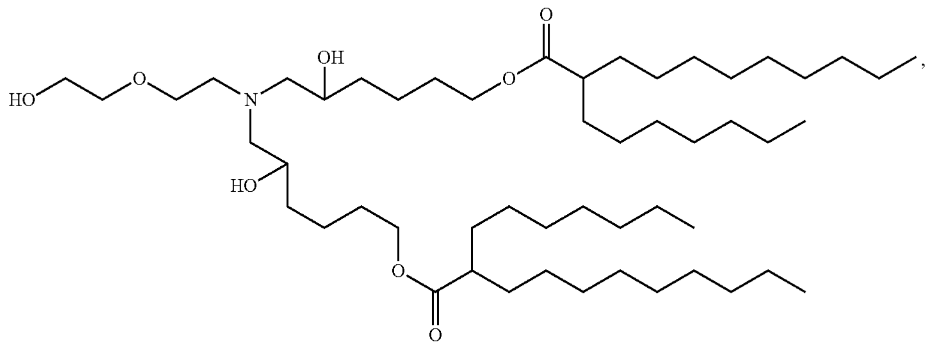
,
H-5
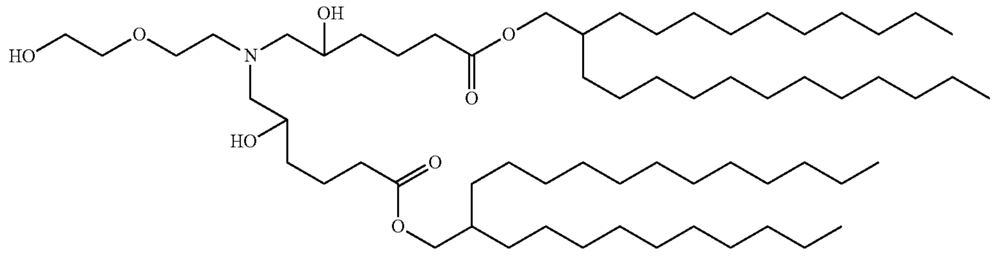
H-6
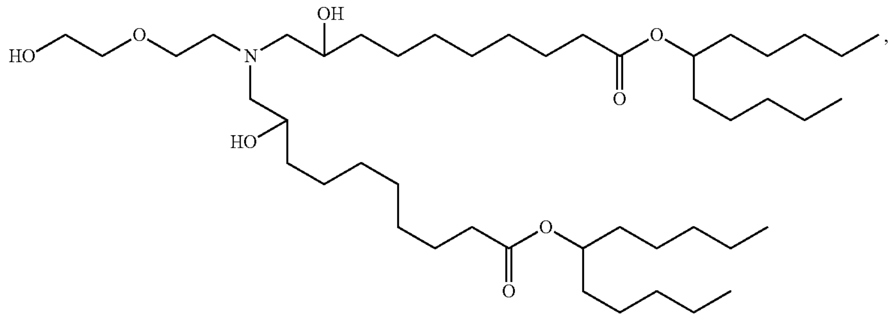
,
H-7
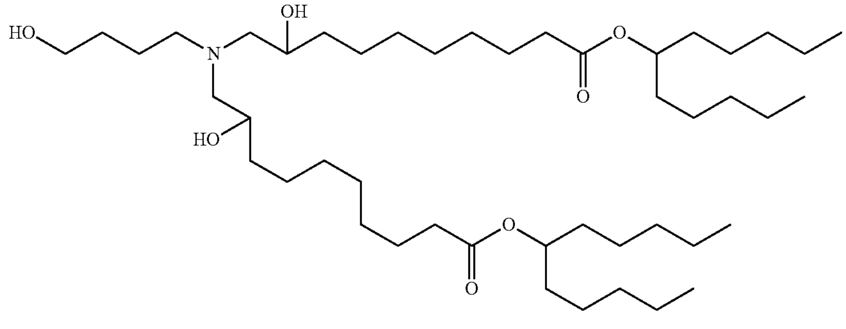

-continued
H-8
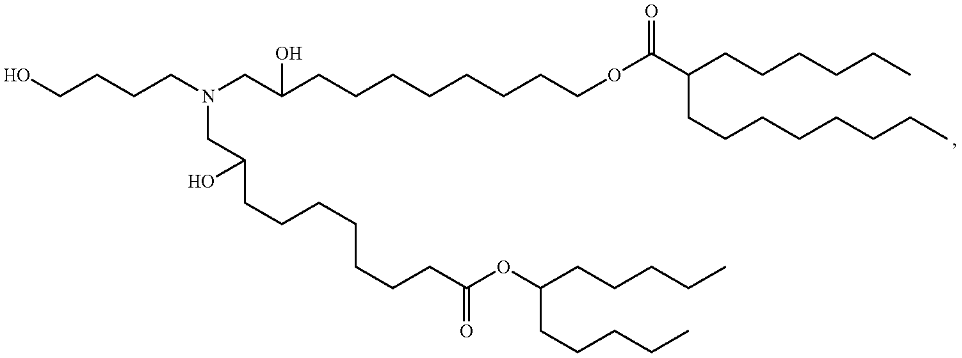
H-9
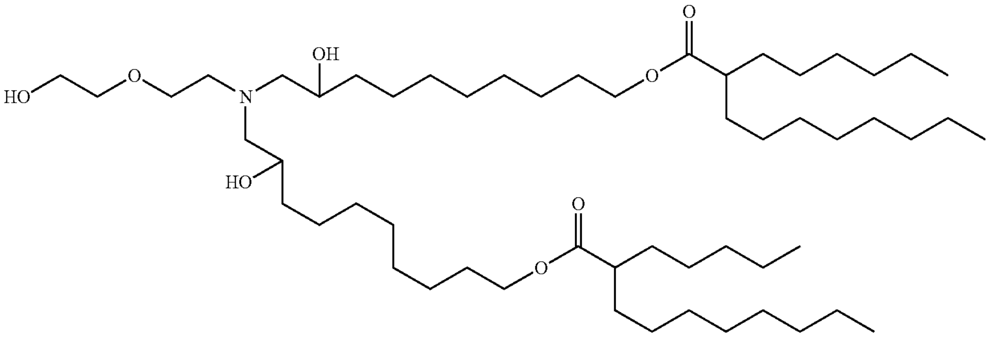
H-10
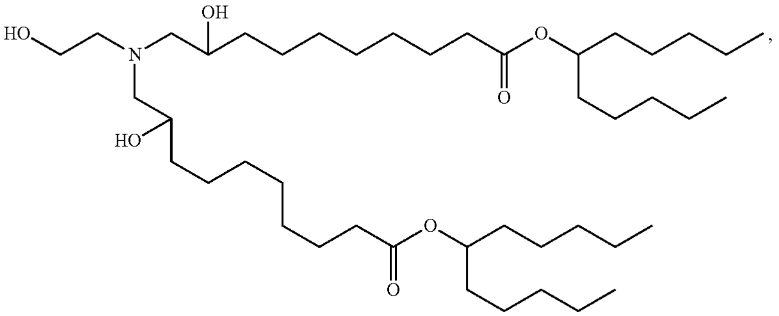
H-11
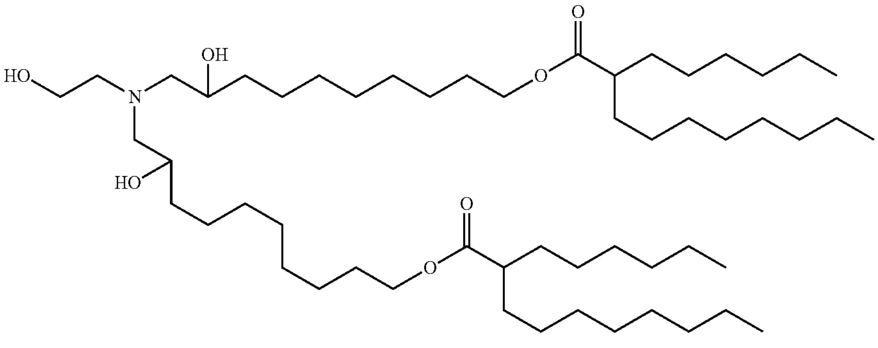

-continued
H-12
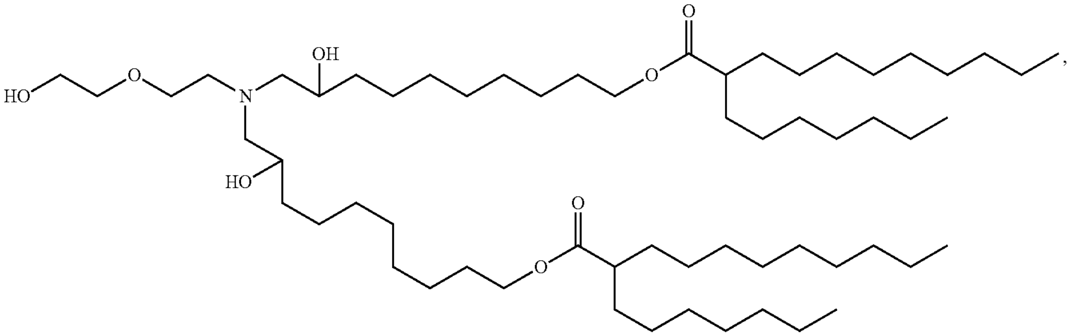
,
H-13
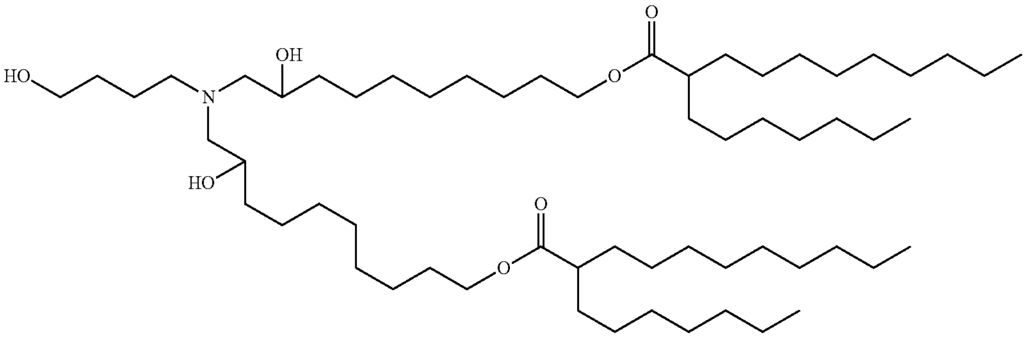
H-14
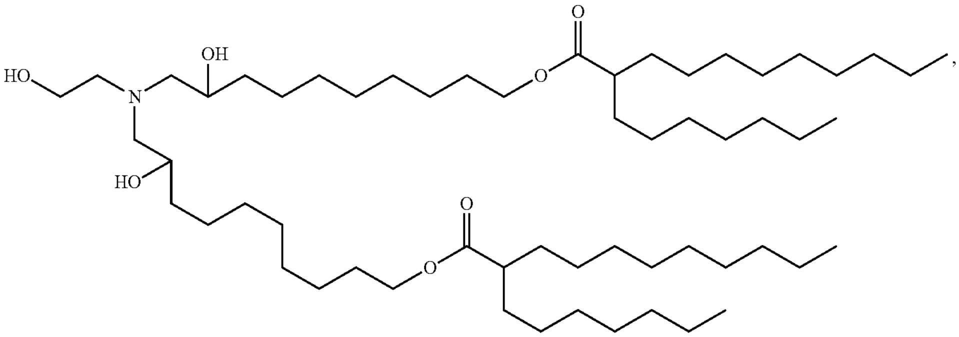
,
H-15
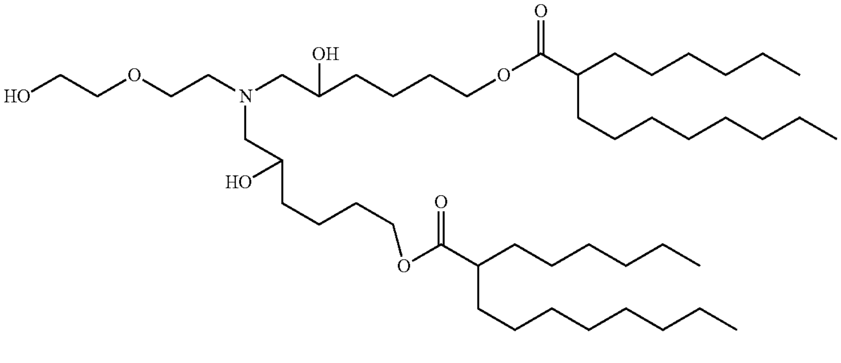

-continued
H-16
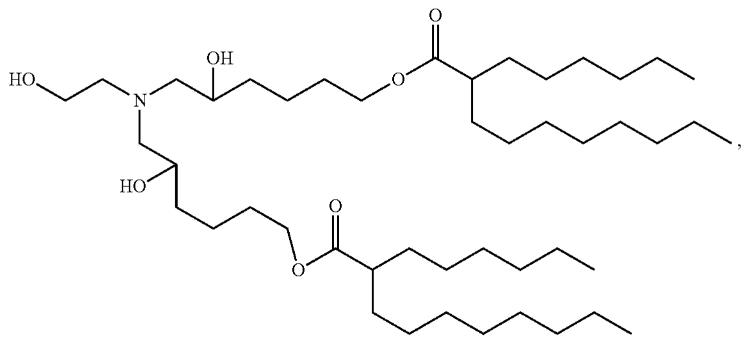
H-18
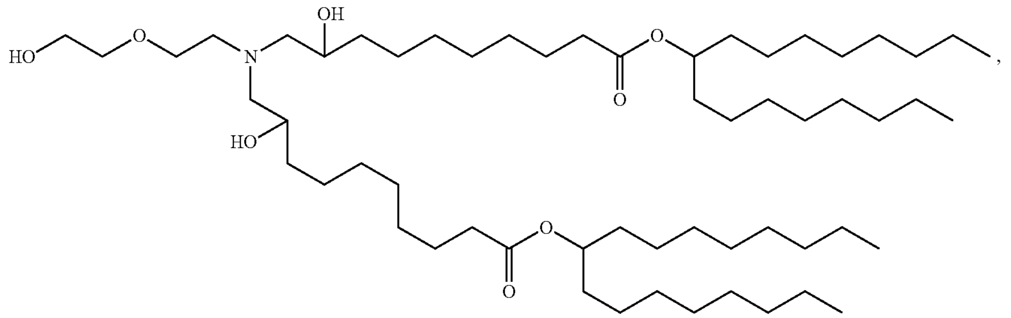
H-19
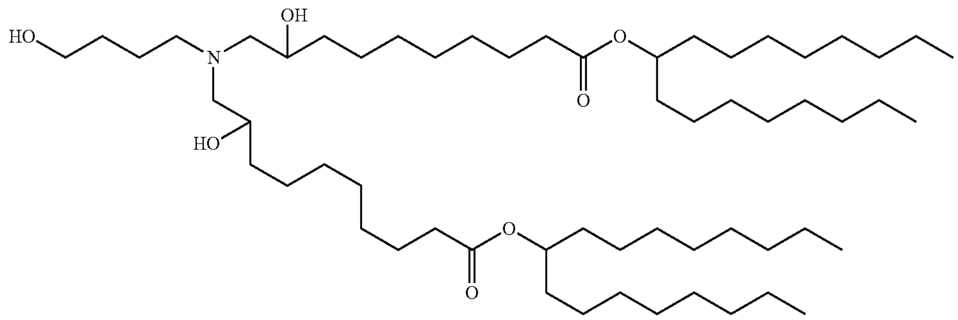
H-20
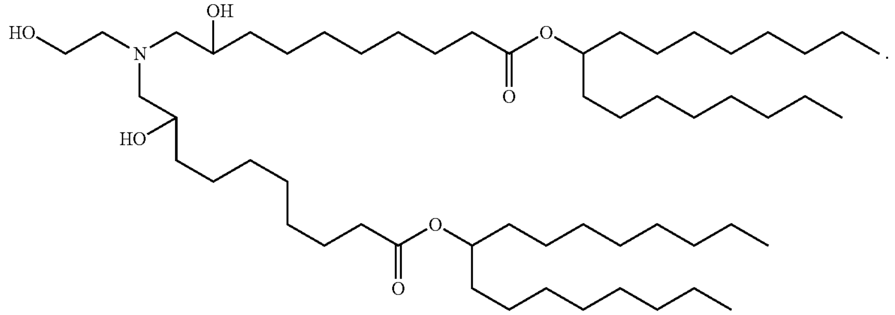

The aforementioned cationic lipid compound, as an embodiment, wherein the compound is as follows:
H-21
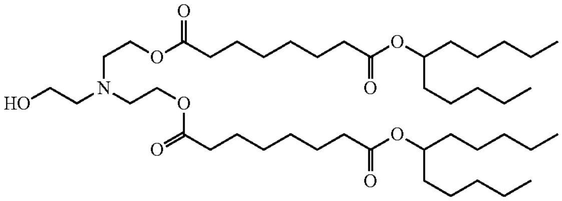
H-23
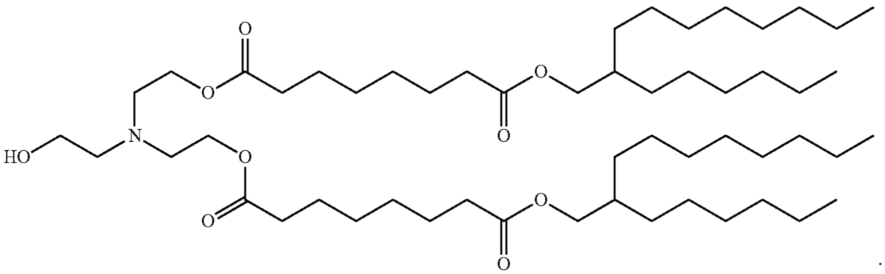
.
The aforementioned cationic lipid compound, as an embodiment, wherein the compound is as follows:
H-22
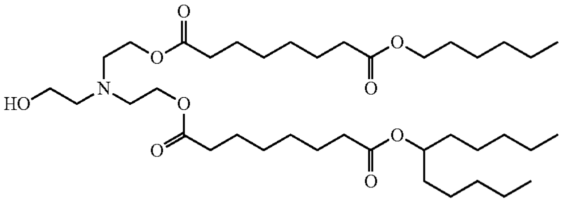
H-24
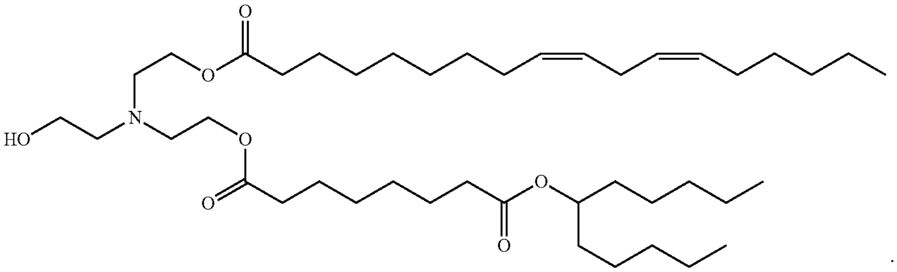
.
The aforementioned cationic lipid compound, as an embodiment, wherein the compound is as follows:

H-25
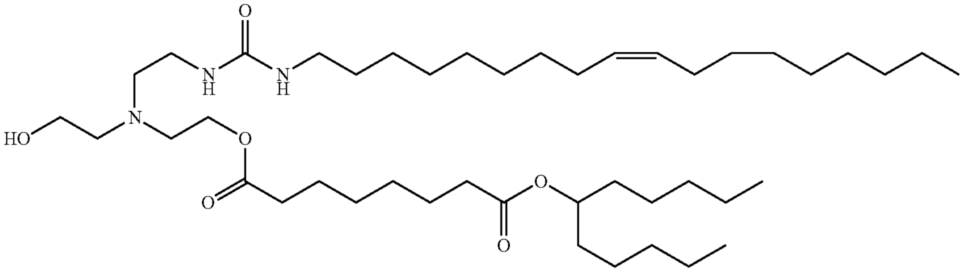
H-26
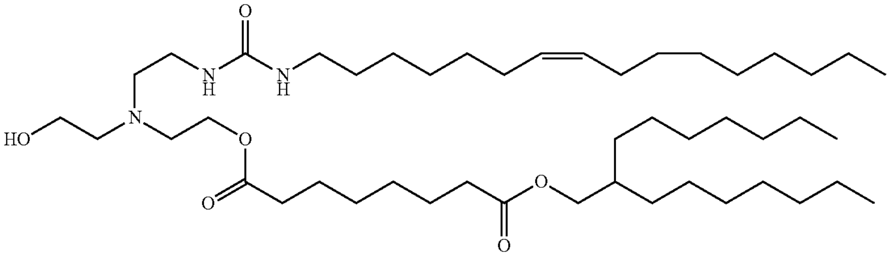
H-27
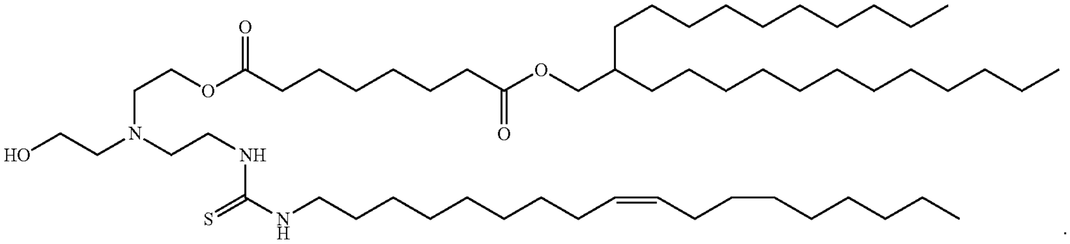
.
The aforementioned cationic lipid compound, as an embodiment, wherein the compound is as follows:
H-28
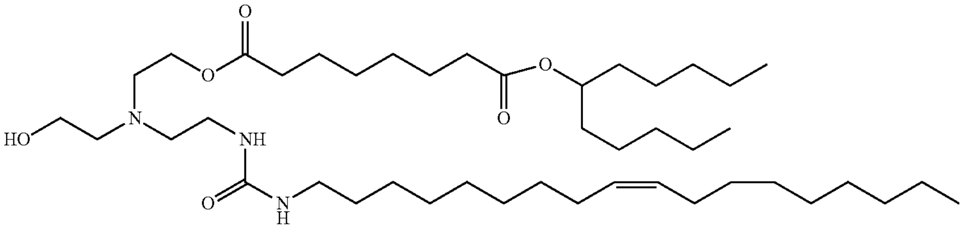
H-29
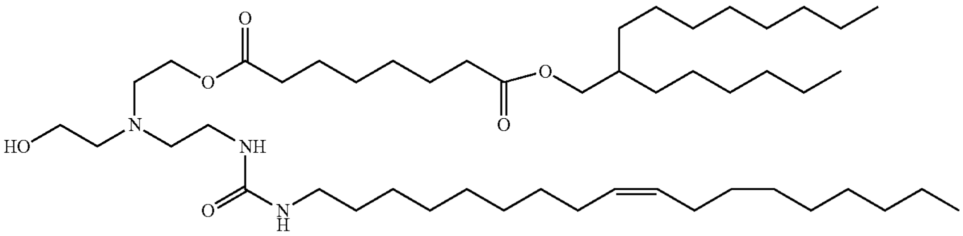
.
The aforementioned cationic lipid compound, as an embodiment, wherein the compound is as follows:

H-17
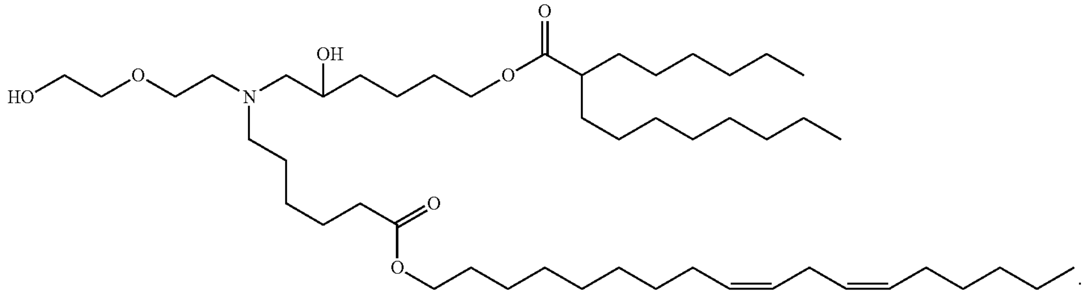
The aforementioned cationic lipid compound, as an embodiment, wherein the compound is as follows:
H-2
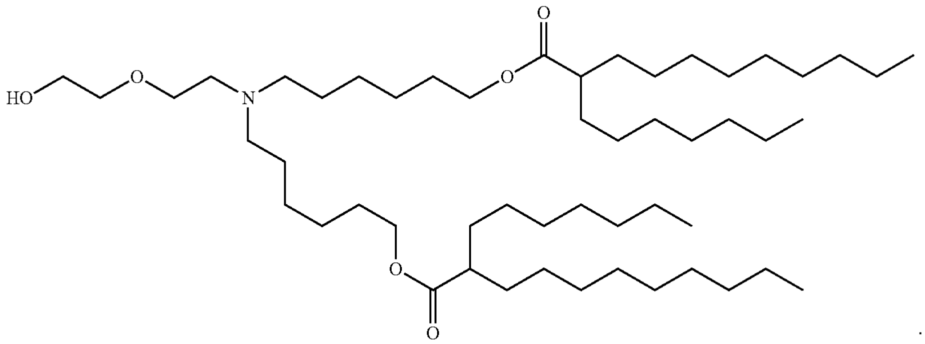
The aforementioned cationic lipid compound, wherein the compound is as follows:
H-30
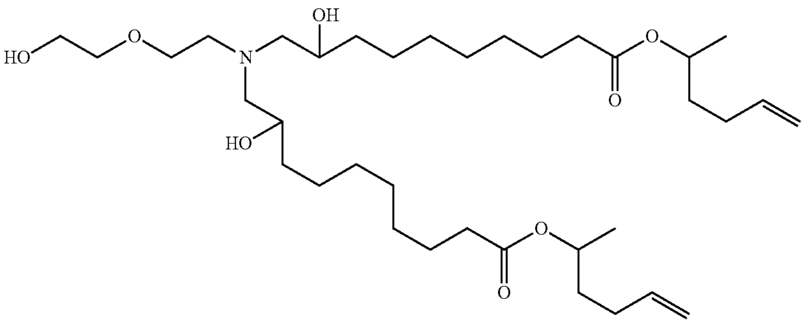
H-31
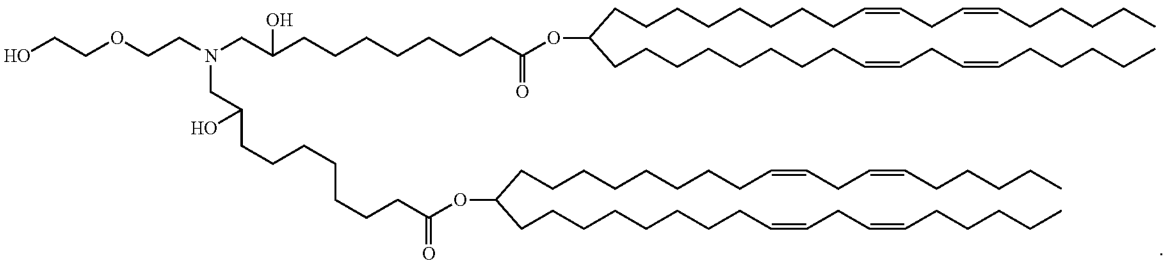

The preparation method of aforementioned cationic lipid compounds H-1, H-3-H-16, and H-18-H-20 comprises the following steps:

Synthesis of the first intermediate: the long-chain alkyl carboxylic acid dissolved in dichloromethane is esterified with olefin-ended long-chain alkyl alcohol with the existence of 1-(3-dimethylaminopropyl)-3-ethylcarbodiimide as an activator to obtain the first intermediate;

Synthesis of the second intermediate: the double bond is oxidized by meta-Chloroperbenzoic acid to form epoxy to obtain the second intermediate;

Synthesis of cationic lipid compounds: the amine undergoes the ring-opening reaction with the epoxy under heating so as to form the cationic lipid compound by linking the hydrophilic head and hydrophobic tail of the cation.

Preparation method of aforementioned cationic lipid compounds with H-21 and H-23 structures comprises the following steps:

Synthesis of the first intermediate: long-chain alkyl carboxylic acid dissolved in dichloromethane is esterified with triethanolamine with the existence of 1-(3-dimethylaminopropyl)-3-ethylcarbodiimide as an activator;

Synthesis of the second intermediate: long-chain alkyl carboxylic acid dissolved in dichloromethane is esterified with long-chain alkyl alcohol compound with the existence of 1-(3-dimethylaminopropyl)-3-ethylcarbodiimide as activators to obtain the second intermediate;

Synthesis of cationic lipid compounds: the second intermediate dissolved in dichloromethane is esterified with the first intermediate with the existence of 1-(3-dimethylaminopropyl)-3-ethylcarbodiimide as an activator.

Preparation method of aforementioned cationic lipid compounds H-22 and H-24 comprises the following steps:

Synthesis of the first intermediate: under alkalines condition, using long-chain alkyl amine and carbon disulfide to form the corresponding isothiocyanate with the existence of 4-dimethylaminopyridine and di-tert-butyl dicarbonate ester as an catalyst;

Synthesis of the second intermediate: isothiocyanate reacts with amine through affinity substitution in solvent to form the corresponding thiourea.

Synthesis of the third intermediate: long-chain alkyl carboxylic acid dissolved in dichloromethane is esterified with long-chain alkyl alcohol compound with the existence of 1-(3-dimethylaminopropyl)-3-ethylcarbodiimide as an activator;

Synthesis of cationic lipid compounds: the third intermediate dissolved in dichloromethane is esterified with the second intermediate with the existence of 1-(3-dimethylaminopropyl)-3-ethylcarbodiimide as an activator.

Preparation method of aforementioned cationic lipid compounds H-25, H-26, and H-27 comprises the following steps:

Synthesis of the first intermediate: amine is used to react with triphosgene to form isocyanate under alkaline conditions, then the corresponding first intermediate containing urea unit was formed by the reaction between the isocyanate reacts and amine;

Synthesis of the second intermediate: long-chain alkyl carboxylic acid dissolved in dichloromethane is esterified with long-chain alkyl alcohol compound with the existence of 1-(3-dimethylaminopropyl)-3-ethylcarbodiimide as an activator;

Synthesis of cationic lipid compounds: the second intermediate dissolved in dichloromethane is esterified with the first intermediate with the existence of 1-(3-dimethylaminopropyl)-3-ethylcarbodiimide as an activator.

Preparation method of aforementioned cationic lipid compounds with H-28 and H-29 structures comprises the following steps:

Synthesis of the first intermediate: esterification occurs between linoleic alcohol and bromoacyl chloride under alkaline condition to obtain brominated long-chain alkane;

Synthesis of the second intermediate: the double bond is oxidized by meta-Chloroperbenzoic acid to form epoxy;

Synthesis of the third intermediate: the intermediate was formed by the nucleophilic substitution reaction between the brominated long-chain alkane of the first intermediate under alkaline conditions;

Synthesis of cationic lipid compounds: under heating condition, the compound was formed by ring opening reaction between the epoxy of the second intermediate and the amine of the third intermediate.

Preparation method of the aforementioned cationic lipid compound with H-17 structure comprises the following steps:

Synthesis of the first intermediate: long-chain alkyl carboxylic acid compound dissolved in dichloromethane is esterified with dihydric alcohol with the existence of 1-(3-dimethylaminopropyl)-3-ethylcarbodiimide as an activator;

Synthesis of the second intermediate: the first intermediate long-chain alkyl alcohol is oxidized to long-chain alkyl aldehyde using Dess-Martin periodinane;

Synthesis of cationic lipid compounds: obtained by reduction amination reaction between amine and aldehyde group of the second intermediate.

Preparation method of aforementioned cationic lipid compound with H-2 structure comprises the following steps:

The synthesis of the first intermediate: the double bond is oxidized by meta-Chloroperbenzoic acid to form epoxy to obtain the first intermediate;

Synthesis of the second intermediate: long-chain epoxy alkyl carboxylic acid dissolved in dichloromethane is esterified with terminal long-chain alkyl alcohol under the activation of 1-(3-dimethylaminopropyl)-3-ethylcarbodiimide to obtain the second intermediate;

Synthesis of cationic lipid compounds: cationic lipid compound was formed by the ring opening reaction between amine and epoxy under heating condition to link the hydrophilic head and hydrophobic tail of the cation.

Preparation method of aforementioned cationic lipid compounds with H-30 and H-31 structures comprises the following steps:

The synthesis of the first intermediate: the double bond is oxidized by meta-Chloroperbenzoic acid to form epoxy to obtain the first intermediate;

Synthesis of the second intermediate: long-chain epoxy alkyl carboxylic acid dissolved in dichloromethane is esterified with terminal long-chain alkyl alcohol under the activation of 1-(3-dimethylaminopropyl)-3-ethylcarbodiimide to obtain the second intermediate;

Synthesis of cationic lipid compounds: cationic lipid compound was formed by the ring opening reaction between amine and epoxy under heating condition to link the hydrophilic head and hydrophobic tail of the cation.

The application of the aforementioned cationic lipid compound for a composition comprising a cationic lipid compound, a stereoisomer thereof, tautomer thereof, or pharmaceutically acceptable salt thereof.

The application of the aforementioned cationic lipid compound, wherein the composition comprising the cationic lipid compound comprises: a carrier, a loaded drug, a pharmaceutical adjuvant.

The application of the aforementioned cationic lipid compound, wherein the carrier is LNPs, the average size of the LNPs ranges from 30-200 nm, and the polydispersity index of the LNPs is ≤0.5.

The application of the aforementioned cationic lipid compound, wherein the carrier comprises one or more ionizable lipid compounds.

The application of the aforementioned cationic lipid compound, wherein the carrier further comprises: helper lipids, and the molar ratio of cationic lipid compounds to helper lipids ranges from 0.5:1-10:1. Such molar ratio is a preferred embodiment, and any composition of cationic lipid compounds with the structure listed in this invention fall within the scope of protection of this invention and is inspired by this invention. The helper lipids include one or more of phosphatidylcholine, phosphatidylethanolamine, sphingomyelin, sterols and their derivative, ceramide, and charged lipid.

The application of the aforementioned cationic lipid compound, wherein the carrier further comprises structural lipids or polymer-conjugated lipids.

The application of the aforementioned cationic lipid-compound, wherein the carrier further comprises structural lipids, and the molar ratio of cationic lipid compounds to structural lipids ranges from 0.5:1-5:1. Such molar ratio is a preferred embodiment, and any composition of cationic lipid compounds with the structure listed in this invention fall within the scope of protection of this invention and is inspired by this invention.

The application of the aforementioned cationic lipid compound, wherein the carrier further comprises polymer-conjugated lipids, and the molar ratio of cationic lipid compounds to polymer-conjugated lipids ranges from 20:1-250:1. The polymer-conjugated lipid is PEGylated lipid.

The application of the aforementioned cationic lipid compound, wherein the drug reagent includes one or more of nucleic acid molecules, small molecule compounds, peptides, or proteins.

The selection and formulation of the drug reagents are not limited, and any cationic lipid compound with the structure listed in this invention fall within the scope of protection of this invention and are inspired by this invention.

The application of the aforementioned cationic lipid compound, wherein the drug adjuvant includes one or more of diluents, stabilizers, preservatives, or lyoprotectants. The selection and formulation of drug adjuvants are not limited, and any cationic lipid compounds with the structure listed in this invention fall within the scope of protection of this invention and are inspired by this invention.

The advantages described in this invention are as follows:

The lipid compounds described in this invention feature hydroxyl group in the head structure, which confers hydrophilicity and capacities of fusing membrane. Meanwhile, the overall structure resembles a cone with a small head (nitrogen-containing moiety) and a large tail (long-chain alkane of hydrophobic moiety). The LNPs prepared using the cationic lipid compounds with the aforementioned optimal structure usually exhibit enhanced biocompatibility and higher in vivo mRNA transfection efficiency, achieving unexpected technical effects.

The ionization of amine groups in the cationic lipid compounds described in this invention can efficiently bind to nucleic acids, favoring encapsulation of nucleic acid's;

Degradable ester bonds introduced into the hydrophobic tail part of the cationic lipid compounds described in this invention can be rapidly degraded by esterolytic enzymes in vivo. This modification alters the metabolic behavior of lipid molecules in vivo, thereby enhancing the biosafety of mRNA-LNPs.

The LNPs prepared from the cationic lipid compounds described in this invention form stable nanostructures with narrow size distributions, ranging from 30 to 200 nm, with variations dependent on the specific lipid compound structures;

The LNPs described in this invention are stable and can be stored at low temperatures for 120-150 days.

Compared with the synthesis of cationic lipid compounds commonly used in the prior art (such as MC3), the synthesis process described in this invention is simple, feasible and inexpensive. The raw materials are readily available, thus being suitable for industrial production.

The mRNA-LNPs prepared from the cationic lipid compounds described in this invention can provide safe and effective delivery vehicles for the development of nucleic acid therapeutics or vaccines to treat a wide range of diseases (including metabolic disorders, respiratory illnesses, cardiovascular diseases, and tumors, etc.). Such LNPs are designed for various unmet clinical needs, can be applied for diverse application scenarios and purposes (cell therapy, gene editing, targeting technologies, etc.) through various administration routes (such as intramuscular injection, subcutaneous injection, intravenous injection, local injection, inhalation, and transdermal delivery, etc.).

BRIEF DESCRIPTION OF THE DRAWINGS

The FIGURE depicts a transmission electron microscopy image of the LNPs formed from the cationic lipid compound H-1 in Example 3 described in this invention.

Terms and Abbreviations:

Nucleic acids, collectively referring to deoxyribonucleic acid (DNA) and ribonucleic acid (RNA), are biological macromolecules composed of multiple nucleotide monomers. Nucleic acids consist of nucleotides, each containing a pentose, a phosphate group, a nitrogenous base, or any modification group. If the pentose is ribose, the resulting polymer is RNA; if the pentose is deoxyribose, the resulting polymer is DNA.

Nucleic acid molecules include single-stranded DNA, double-stranded DNA, short isoforms, mRNA, tRNA, rRNA, long non-coding RNA (lncRNA), micro non-coding RNA (miRNA), siRNA, telomerase RNA component, small nuclear RNA (snRNA), circular RNA (circRNA), synthetic miRNA (miRNA mimics, miRNA agomir, miRNA antagomir), antisense DNA, antisense RNA, ribozymes, asymmetric interfering RNA (aiRNA), dicer-substrate RNA (dsRNA), small hairpin RNA (shRNA), gRNA, sgRNA, crRNA, tracrRNA, locked nucleic acid (LNA), peptide nucleic acid (PNA), morpholine antisense oligonucleotide, morpholine oligonucleotide, or biologically customized oligonucleotide. The examples provided here are not exhaustive, and any nucleotide polymer can be applied to the present invention.

The pharmaceutically acceptable salts include both acid and base addition salts.

Wherein the acids used in acid addition salts include, but are not limited to: hydrochloric acid, hydrobromic acid, sulfuric acid, nitric acid, phosphoric acid, acid phosphate, acetic acid, 2,2-dichloroacetic acid, adipic acid, alginic acid, ascorbic acid, aspartic acid, benzenesulfonic acid, benzoic acid, 4-acetylaminobenzoic acid, camphoric acid, camphor-10-sulfonic acid, capric acid, hexanoic acid, caprylic acid, carbonic acid, cinnamic acid, citric acid, cyclic amino acid, dodecyl sulfuric acid, ethane-1,2-disulfonic acid, ethanesulfonic acid, 2-hydroxyethanesulfonic acid, formic acid, fumaric acid, galactolic acid, gentian acid, gluproheptanoic acid, gluconic acid, glucan acid, glucuronic acid, glutamic acid, glutaric acid, 2-oxoglutaric acid, glycerophosphate, glycolic acid, hippuric acid, isobutyric acid, lactic acid, lactobionic acid, lauric acid, maleic acid, malic acid, malonic acid, mandelic acid, methanesulfonic acid, mucoic acid, naphthalene-1,5-dicarboxylic acid, naphthalene-2-sulfonic acid, 1-hydroxy-2-naphthalic acid, niacin, oleic acid, orotic acid, oxalic acid, palmitic acid, palmitic acid, propionic acid, pyroglutamic acid, pyruvate, salicylic acid, 4-aminosalicylic acid, sebacic acid, stearic acid, succinic acid, tartaric acid, thiocyanic acid, p-toluenesulfonic acid, trifluoroacetic acid, quaternary ammonium acid, and undecylenic acid.

Examples of alkali metal salts include, but are not limited to: sodium salts, potassium salts, lithium salts, ammonium salts, calcium salts, magnesium salts, iron salts, zinc salts, copper salts, manganese salts, and aluminum salts; organic alkali include, but not limited to: ammonia, isopropylamine, trimethylamine, diethylamine, triethylamine, tripropylamine, diethanolamine, ethanolamine, dealcoholization, 2-dimethylaminoethanol, 2-diethylaminoethanol, lysine, arginine, histidine, caffeine, procaine, hydrazine, choline, betaine, benzamine, benzathine, ethylenediamine, glucosamine, methylglucosamine, theobromine, triethanolamine, purine, piperazine, piperidine, N-ethylpiperidine, and polyamine resins; preferably, the organic alkali are isopropylamine, diethylamine, ethanolamine, trimethylamine, dicyclohexylamine, choline, and caffeine.

The charged lipids refer to a class of lipid compounds existing in the form of positive or negative charges. These charges are independent on the physiological pH (such as pH 3-9) range, and are unaffected by pH. Charged lipids can be synthetic or natural origin. Examples of charged lipids include, but are not limited to, DOTAP, DOTMA, and 18PA.

mRNA, also referred to as messenger RNA, is a single-stranded ribonucleic acid transcribed from a strand of DNA, carrying genetic information to guide protein synthesis. mRNA can be either monocistronic mRNA or polycistronic mRNA. Additionally, mRNA may contain one or more functional nucleotide analogues, such as pseudouracil, 1-methyl-pseudouracil, or 5-methylcytosine. The examples are not exhaustive, and any modified mRNA or its derivatives can be applied to the present invention.

The small molecule compounds can serve as active ingredients in reagents used for treatment or prevention, including anti-tumor drugs, anti-infectives, local anesthetics, antidepressants, anticonvulsants, antibiotics/antimicrobials, antifungals, antiparasitic drugs, hormones, hormone antagonists, immunomodulators, neurotransmitter antagonists, antiglaucoma agents, anesthetics, and imaging agents. The examples are not exhaustive.

The peptides are compounds formed by the linking of α-amino acids via peptide bonds, and they represent intermediates of proteolysis.

The proteins are substances composed of amino acids linked together through "dehydration condensation" to form polypeptide chains that fold into specific spatial structures. Proteins can include interferons, protein hormones, cytokines, chemokines, and enzymes, etc.

The diluents are any water-soluble excipients known to those skilled in the art in this field, which can be pharmaceutically acceptable, including amino acids, monosaccharides, disaccharides, trisaccharides, tetrasaccharides, pentaccharides, other oligosaccharides, mannitol, dextroside, sodium chloride, sorbitol, polyethylene glycol, phosphates, or derivatives thereof.

The stabilizers can be any pharmaceutical excipients known to those skilled in the art in this field, including: Tween-80, sodium dodecyl sulfate, sodium oleate, mannitol, mannose, or sodium alginate, etc.

The preservatives can be any pharmaceutical preservatives known to those skilled in the art in this field, such as thimerosal, etc.

The lyoprotectants can be any pharmaceutical lyoprotectants known to those skilled in the art in this field, such as glucose, mannitol, sucrose, lactose, trehalose, or maltose, etc.

DSPC: distearoyl Phosphatidylcholine, 1,2-distearoyl-sn-glycero-3-phosphoryline, CAS number: 816-94-4.

DPPC: dipalmitoyl Phosphatidylcholine, 1,2-dipalmitoyl-sn-glycero-3-phosphocholine, CAS number: 63-89-8.

DMPC: dimyristoyl Phosphatidylcholine; 1,2-dmyristoyl-sn-glycor-3-phosphocholine, CAS number: 18194-24-6.

DOPC: 1,2-dioloyl-sn-glycerin-3-phosphocholine; CAS number: 4235-95-4.

POPC: 2-oleoyl-1-palmitotin glycerol-3-phosphocholine, CAS number: 26853-31-6.

DOPE: 1,2-dioloyl-sn-glycerin-3-phosphoyl-ethanolamine, CAS number: 4004-05-1.

DOTAP: 1,2-dioleyl-3-trimethylammonium propane (chloride salt), CAS number: 132172-61-3; the chemical structural formula is as follows:

DOTAP

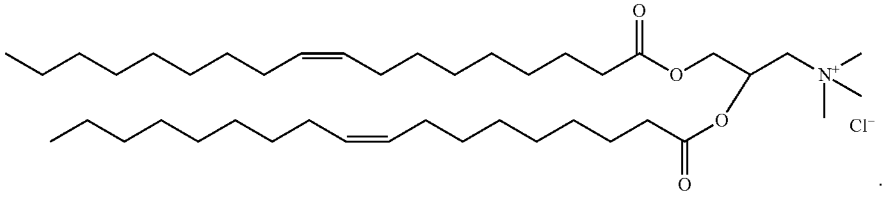

.

DOTMA: N,N,N-trimethyl-2,3-bis(octadecan-9-en-1-yloxy)propan-1-ammonium chloride, CAS number: 1325214-86-5; the chemical structural formula is as follows:

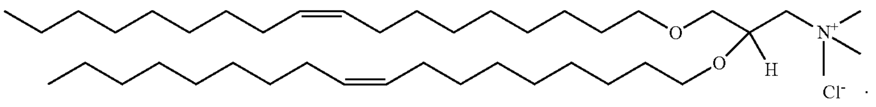 [SMILES: CCCCCCCC/C=C\CCCCCCCCOCC(C[N+](C)(C)C)OCCCCCCCC/C=C\CCCCCCCC ; [Cl-]]

18PA: CAS number: 108392-02-5; the chemical structure formula is as follows:

18PA

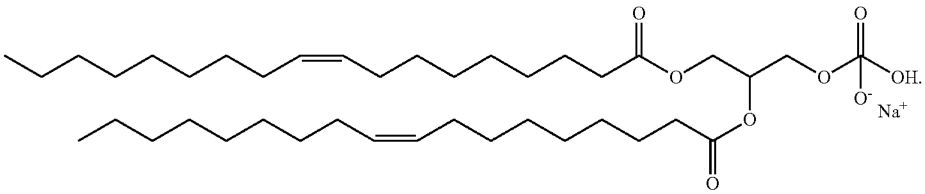

SM: sphingomyelin.

PEG: polyethylene glycol.

In this invention, when the number of repeating units in the compound structure is indicated as "0-10", it means that the number of repeating units can be optionally 0, 1, 2, 3, 4, 5, 6, 7, 8, 9 or 10.

DETAILED DESCRIPTION

The present invention is introduced in detail with the drawings and examples.

Cationic Lipid Compound

The cationic lipid compound described in this invention is a compound of the following structure:

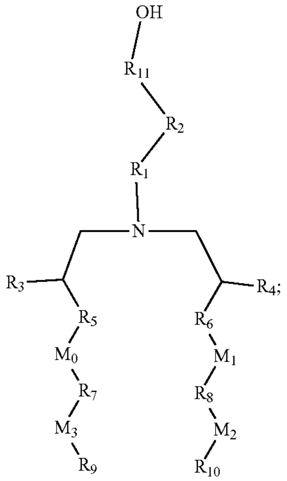

$R_1$ is

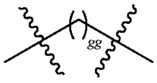

;

gg = 0-10

$R_2$ is

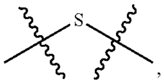

,

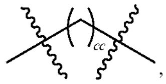

,

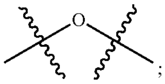

;

cc = 0-10

$R_3$ is H,

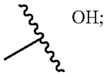

$R_4$ is

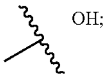

$R_5$ is

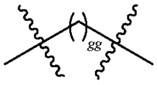

;

gg = 0-10

$R_6$ is
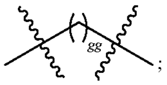
gg = 0-10
$R_7$ is
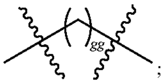
gg = 0-10
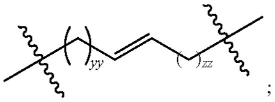
yy = 0-10
zz = 0-10
$R_8$ is
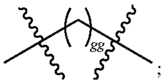
gg = 0-10
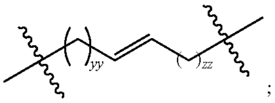
yy = 0-10
zz = 0-10
$R_9$ is
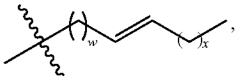
w = 0-10
x = 0-10
M = H, $CH_3$
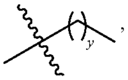
y = 0-10
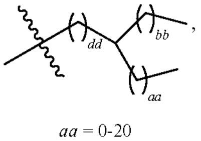
aa = 0-20
bb = 0-20
dd = 0-10
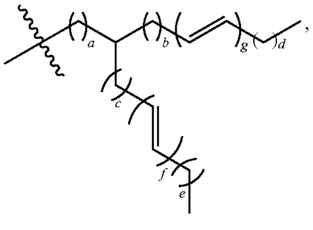
a = 0-10
b = 0-10
g = 0-1
d = 0-10
e = 0-10
f = 0-1
c = 0-10
-continued
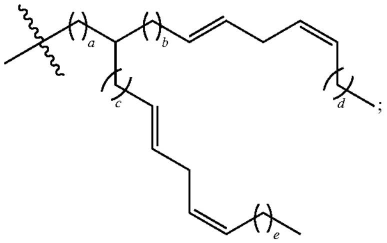
a = 0-10
b = 0-10
c = 0-10
d = 0-10
e = 0-10
$R_{10}$ is
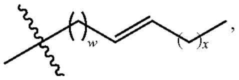
w = 0-10
x = 0-10
M = H, $CH_3$
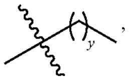
y = 0-10
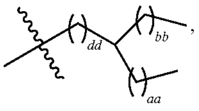
aa = 0-20
bb = 0-20
dd = 0-10
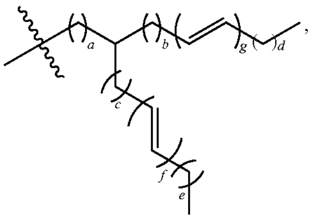
a = 0-10
b = 0-10
g = 0-1
d = 0-10
e = 0-10
f = 0-1
c = 0-10
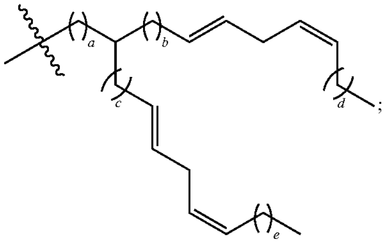
a = 0-10
b = 0-10
c = 0-10
d = 0-10
e = 0-10
$R_{11}$ is
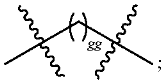
gg = 0-10

$M_0$ and $M_1$ are:

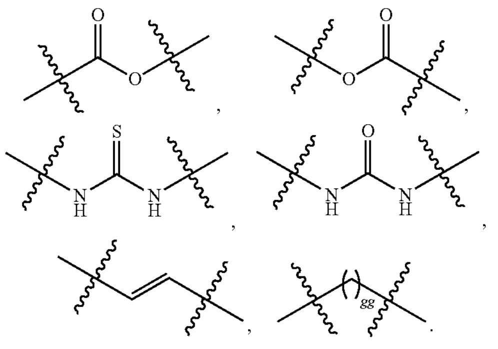

$gg$ = 0-10

$M_2$ and $M_3$ are:

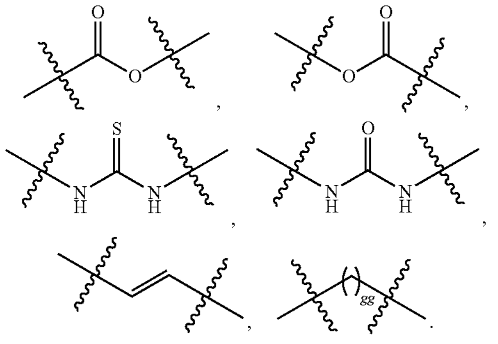

$gg$ = 0-10

The structure of compounds described in this invention resembles a cone with a small head and a large tail. The cationic lipid compounds with the aforementioned optimal structure and the hydroxyl group introduced in the head have achieved better biocompatibility and higher in vivo mRNA transfection efficiency.

Preparation of Cationic Lipid Compounds

This invention provides a preparation method for the cationic lipid compound, which comprises the following steps:

- Synthesis of the first intermediate: the long-chain alkyl carboxylic acid dissolved in dichloromethane is esterified with olefin-ended long-chain alkyl alcohol with the existence of 1-(3-dimethylaminopropyl)-3-ethylcarbodiimide as an activator to afford the first intermediate;
- Synthesis of the second intermediate: the double bond is oxidized by meta-Chloroperbenzoic acid to form epoxy to obtain the second intermediate;
- Synthesis of cationic lipid compounds: the amine undergoes the ring-opening reaction with the epoxy under heating so as to form the cationic lipid compound by linking the hydrophilic head and hydrophobic tail of the cation.

The method is preferably used for the preparation of compounds H-1, H-3, H-4, H-5, H-6, H-7, H-8, H-9, H-10, H-11, H-12, H-13, H-14, H-15, H-16, H-18, H-19, H-20.

This invention provides another method for the preparation of cationic lipid compound, which comprises the following steps:

- Synthesis of the first intermediate: long-chain alkyl carboxylic acid dissolved in dichloromethane is esterified with long-chain alkyl alcohol compound with the existence of 1-(3-dimethylaminopropyl)-3-ethylcarbodiimide as an activator to obtain the first intermediate;
- Synthesis of cationic lipid compounds: the first intermediate, long-chain alkyl carboxylic acid, is dissolved in dichloromethane and then esterified with triethanolamine with the existence of 1-(3-dimethylaminopropyl)-3-ethylcarbodiimide as an activator.

The method is preferably used for the preparation of compound H-21 or H-23.

This invention provides another method for the preparation of cationic lipid compound, which comprises the following steps:

- Synthesis of the first intermediate: long-chain alkyl carboxylic acid dissolved in dichloromethane is esterified with triethanolamine with the existence of 1-(3-dimethylaminopropyl)-3-ethylcarbodiimide as an activator;
- Synthesis of the second intermediate: long-chain alkyl carboxylic acid dissolved in dichloromethane is esterified with long-chain alkyl alcohol compound with the existence of 1-(3-dimethylaminopropyl)-3-ethylcarbodiimide as activators to obtain the second intermediate;
- Synthesis of cationic lipid compounds: the second intermediate dissolved in dichloromethane is esterified with the first intermediate with the existence of 1-(3-dimethylaminopropyl)-3-ethylcarbodiimide as an activator.

The method is preferably used for the preparation of compounds H-22 and H-24.

This invention provides another method for the preparation of cationic lipid compound, which comprises the following steps:

- Synthesis of the first intermediate: under alkalines condition, using long-chain alkyl amine and carbon disulfide to form the corresponding isothiocyanate with the existence of 4-dimethylaminopyridine and di-tert-butyl dicarbonate ester as an catalyst;
- Synthesis of the second intermediate: isothiocyanate reacts with amine through affinity substitution in solvent to form the corresponding thiourea;
- Synthesis of the third intermediate: long-chain alkyl carboxylic acid dissolved in dichloromethane is esterified with long-chain alkyl alcohol compound with the existence of 1-(3-dimethylaminopropyl)-3-ethylcarbodiimide as an activator;
- Synthesis of cationic lipid compounds: the third intermediate dissolved in dichloromethane is esterified with the second intermediate with the existence of 1-(3-dimethylaminopropyl)-3-ethylcarbodiimide as an activator.

The method is preferably used for the preparation of compounds H-25, H-26, H-27.

This invention provides another method for the preparation of cationic lipid compound, which comprises the following steps:

- Synthesis of the first intermediate: amine is used to react with triphosgene to form isocyanate under alkaline conditions, then the corresponding first intermediate containing urea unit was formed by the reaction between the isocyanate reacts and amine;
- Synthesis of the second intermediate: long-chain alkyl carboxylic acid dissolved in dichloromethane is esterified with long-chain alkyl alcohol compound with the existence of 1-(3-dimethylaminopropyl)-3-ethylcarbodiimide as an activator;

Synthesis of cationic lipid compounds: the second intermediate dissolved in dichloromethane is esterified with the first intermediate with the existence of 1-(3-dimethylaminopropyl)-3-ethylcarbodiimide as an activator.

The method is preferably used for the preparation of compounds H-28, H-29.

This invention provides another method for the preparation of cationic lipid compounds, characterized in that it comprises the following steps:

Synthesis of the first intermediate: esterification occurs between linoleic alcohol and bromoacyl chloride under alkaline condition to obtain brominated long-chain alkane;

Synthesis of the second intermediate: the double bond is oxidized by meta-Chloroperbenzoic acid to form epoxy;

Synthesis of the third intermediate: the intermediate was formed by the nucleophilic substitution reaction between the brominated long-chain alkane of the first intermediate under alkaline conditions;

Synthesis of cationic lipid compounds: under heating condition, the compound was formed by ring opening reaction between the epoxy of the second intermediate and the amine of the third intermediate.

The method is preferably used for the preparation of compound H-17.

This invention provides another method for the preparation of cationic lipid compound which comprises the following steps:

Synthesis of the first intermediate: long-chain alkyl carboxylic acid compound dissolved in dichloromethane is esterified with dihydric alcohol with the existence of 1-(3-dimethylaminopropyl)-3-ethylcarbodiimide as an activator;

Synthesis of the second intermediate: the first intermediate long-chain alkyl alcohol is oxidized to long-chain alkyl aldehyde using Dess-Martin periodinane;

Synthesis of cationic lipid compounds: obtained by reduction amination reaction between amine and aldehyde group of the second intermediate.

The method is preferably used for the preparation of compound H-2.

This invention provides another method for the preparation of cationic lipid compound which comprises the following steps:

The synthesis of the first intermediate: the double bond is oxidized by meta-Chloroperbenzoic acid to form epoxy to obtain the first intermediate;

Synthesis of the second intermediate: long-chain epoxy alkyl carboxylic acid dissolved in dichloromethane is esterified with terminal long-chain alkyl alcohol under the activation of 1-(3-dimethylaminopropyl)-3-ethylcarbodiimide to obtain the second intermediate;

Synthesis of cationic lipid compounds: cationic lipid compound was formed by the ring opening reaction between amine and epoxy under heating condition to link the hydrophilic head and hydrophobic tail of the cation.

The method is preferably used for the preparation of compounds H-30, H-31.

Pharmaceutical Compositions Comprising the Cationic Lipid Compounds

As an application, the above compounds can be used to prepare a combination for pharmaceutical use, including: carriers, loaded drug reagents, and drug adjuvants, wherein:

The carriers comprise one or more ionizable lipid compounds, helper lipids, structural lipids, or polymer-conjugated lipids. As an embodiment, the carriers are LNPs with an average size ranging from 30-200 nm and the polydispersity index of the nanoparticles is ≤0.5. It should be noted that any nanoparticles prepared using the lipid compounds described in this invention fall within the scope of this patent and are disclosed by this invention. For example, aside from LNPs, they may also be one or more doped nanoparticles formed by lipid compounds and polymers containing carbamate bonds, such as PLGA-PEG, PLA-PEG, PCL, etc. The examples are not exhaustive.

The helper lipids include: phosphatidylcholine, phosphatidylethanolamine, sphingomyelin (SM), sterols and their derivatives, ceramides, and combinations of one or more charged lipids. Preferred phosphatidylcholines include: DSPC, DPPC, DMPC, DOPC, POPC; DOPE is a preferred phosphatidylethanolamine; cholesterol is a preferred sterol; as an embodiment, charged lipids such as DOTAP, DOTMA, or 18PA can be used. The examples are not exhaustive, any combination of lipid compounds using the structure described in present invention falls within protection scope and is disclosed by the present invention. The examples are not exhaustive, and the selection of helper lipids is unrestricted. As long as the lipid compounds utilize the structure described in present invention, they fall within the protection scope and disclosed by this invention.

The structural lipids include one or more cholesterols, nonsterols, sitosterols, ergosterols, campesterols, stigmasterols, brassisterols, tomatines, tomatines, ursolic acids, α-tocopherols, or corticosteroids. The examples are not exhaustive, and the selection of structural lipids is not restricted. Any lipid compounds with the structure listed in this invention fall within the scope of protection of this invention and are disclosed by this invention.

The polymer-conjugated lipids are pegylated lipids; as an embodiment, the pegylated lipids include one or more PEG-modified phosphatidylethanolamines, PEG-modified phosphatidic acids, PEG-modified ceramides, PEG-modified dialkylamines, PEG-modified diacylglycerols, or PEG-modified dialkylglycerols. The examples are not exhaustive, and the selection of polymer-conjugated lipids is not limited. Any lipid compounds with the structure listed in the present invention fall within the scope of protection described in present invention and are inspired by this invention.

The loaded drugs include one or more nucleic acid molecules, small molecule compounds, peptides, or proteins. The examples are not exhaustive, as any lipid compounds with the structure listed in the present invention, regardless of the selected drug, they fall within the protective scope described in present invention and are inspired by this invention.

The pharmaceutical adjuvants include one or more diluents, stabilizers, preservatives, or lyoprotectants. The examples are not exhaustive, as any lipid compounds with the structure listed in the present invention, regardless of the selected pharmaceutical adjuvants, they fall within the protective scope described in present invention and are disclosed by this invention.

The cationic lipid compounds were prepared using the preparation methods described in Examples 1-7.

Example 1

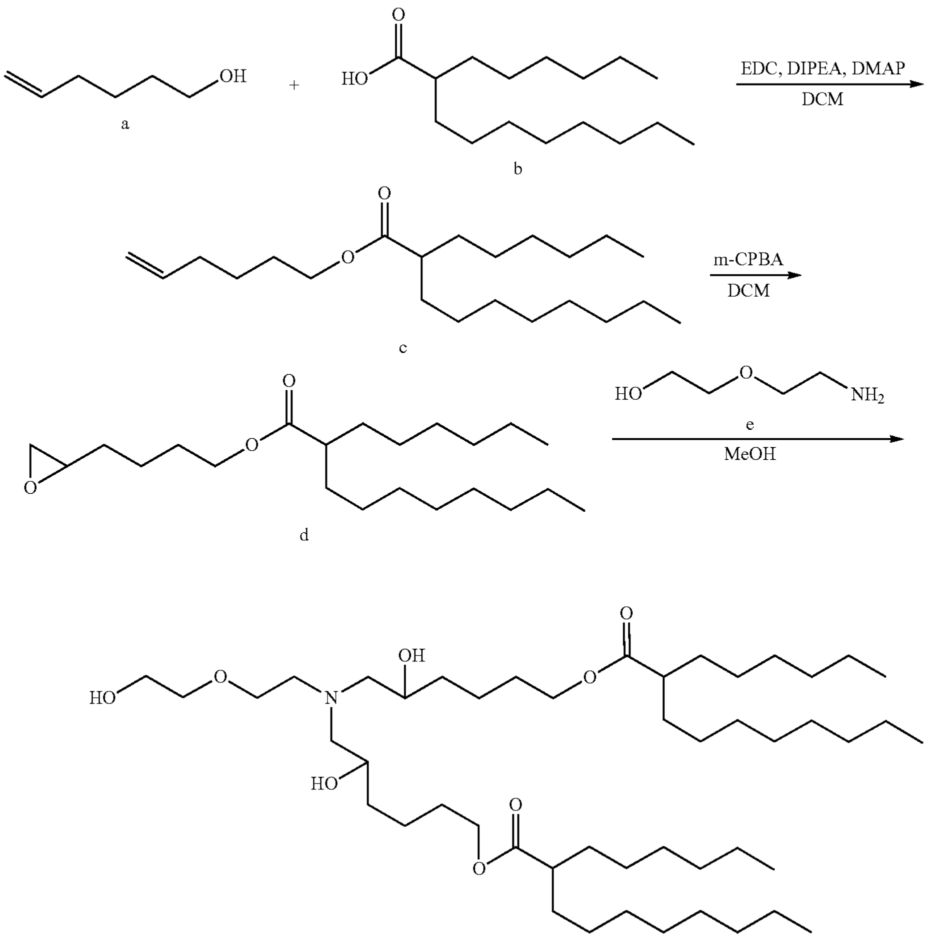

a b c d e

H-15

Synthesis of compound c: 2-Hexidodecanoic acid (compound b, 9.22 g, 36 mmol) was dissolved in 100 mL dichloromethane (DCM), 1-(3-dimethylaminopropyl)-3-ethylcarbodiimide (EDC, 9.2 g, 36 mmol), 4-dimethylaminopyridine (DMAP, 1.46 g, 12 mmol) and N,N-diisopropylethylamine (DIPEA, 7.74 g, 60 mmol) were added to the solution and stirred for 10 minutes. 5-Hexen-1-ol (compound a, 3 g, 30 mmol) was added and the solution was stirred overnight at room temperature. After the reaction, monitored by TLC, was completed, dichloromethane was removed by rotary evaporation, then 200 mL of ethyl acetate was added. The residue was washed with equal volume of saturated sodium chloride solution for three times, the organic phase was dried by anhydrous sodium sulfate for 30 minutes. After the ethyl acetate was removed by rotary evaporation, and the residue was]purified by column (silica gel column, the eluent was PE: EA=3:1 (volume ratio)) to obtain 8.2 g of colorless liquid, yield: 81%.

Synthesis of compound d: compound c (8 g, 24 mmol) was dissolved in 100 mL of DCM, meta-Chloroperbenzoic acid (m-CPBA, 7.2 g, 36 mmol, mass fraction 85%) was added under ice bath and stirred for 15 minutes. After the ice bath was removed, the mixture was stirred overnight. TLC monitored that the reaction was completed, then excess amount of saturated sodium bisulfite solution (10 mL) was added to consume the remaining meta-Chloroperbenzoic acid, and dichloromethane was removed by rotary evaporation, then 200 mL of ethyl acetate was added. The mixture was washed with 200 mL of saturated sodium bicarbonate solution three times and 200 mL of saturated sodium chloride solution for one time, then the organic phase was dried by anhydrous sodium sulfate for 30 minutes. The ethyl acetate was removed by evaporation, separated and purified by column (silica gel column, the eluent was PE: EA=1:1 (volume ratio)) to obtain 6 g of colorless liquid, yield: 72%.

Synthesis of compound H-15: diethylenetriamine (compound e, 0.6 g, 6 mmol) was dissolved in anhydrous methanol, compound d (6 g, 0.17 mmol) was added and stirred at room temperature for 10 minutes, then heated to reflux for 12 hours. TLC monitored that the reaction was completed, then the solvent was removed by rotary evaporation, and the residue was purified by column (silica gel column, the eluent was DCM: MeOH=200:1 (volume ratio)) to obtain 3.9 g of colorless liquid, yield: 85%. MS m/z (ESI): 814.72 $[M+H]^+$ The following compounds were prepared by the method of Example 1: H-1, H-3, H-4, H-5, H-6, H-7, H-8, H-9, H-10, H-11, H-12, H-13, H-14, H-15, H-16, H-18, H-19, H-20.

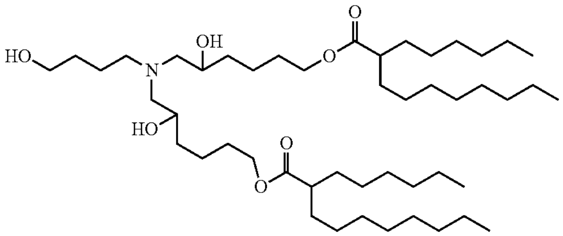 [SMILES: CCCCCCCCC(CCCCCC)C(=O)OCCCCC(O)CN(CCCCO)CC(O)CCCCOC(=O)C(CCCCCC)CCCCCCCC]
H-1
$^1$H NMR (400 MHz, Chloroform-d) δ 4.05 (t, J = 6.5 Hz, 4H), 3.86-3.74 (m, 2H), 3.69-3.57 (m, 2H), 2.80-2.52 (m, 5H), 2.47-2.40 (m, 1H), 2.28 (td, J = 8.9, 5.2 Hz, 2H), 1.74-1.49 (m, 14H), 1.47-1.34 (m, 10H), 1.29-1.17 (m, 40H), 0.85 (t, J = 6.6 Hz, 12H).
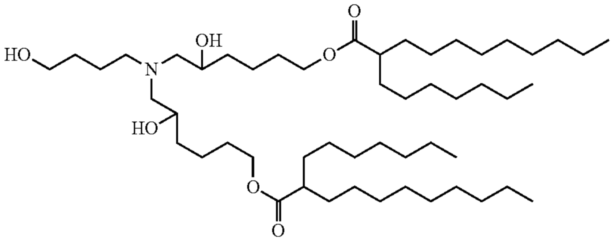 [SMILES: CCCCCCCCCC(CCCCCCC)C(=O)OCCCCC(O)CN(CCCCO)CC(O)CCCCOC(=O)C(CCCCCCC)CCCCCCCCC]
H-3
$^1$H NMR (400 MHz, Chloroform-d) δ 4.05 (t, J = 6.3 Hz, 4H), 3.80-3.70 (m, 2H), 3.68-3.57 (m, 2H), 2.73-2.47 (m, 5H), 2.38 (d, J = 12.5 Hz, 1H), 2.27 (t, J = 7.5 Hz, 4H), 1.78-0.97 (m, 70H), 0.90-0.76 (m, 12H).
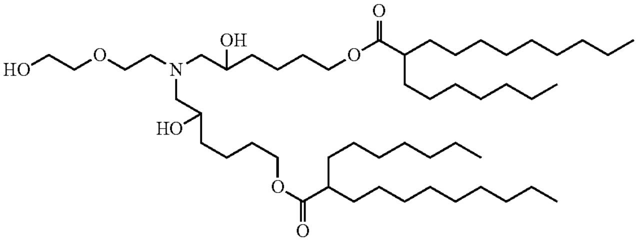 [SMILES: CCCCCCCCCC(CCCCCCC)C(=O)OCCCCC(O)CN(CCOCCO)CC(O)CCCCOC(=O)C(CCCCCCC)CCCCCCCCC]
H-4
$^1$H NMR (400 MHz, Chloroform-d) δ 4.05 (t, J = 6.5 Hz, 4H), 3.81-3.53 (m, 8H), 3.18-2.55 (m, 8H), 2.27 (t, J = 7.6 Hz, 4H), 1.81-0.98 (m, 64H), 0.93-0.73 (m, 12H).
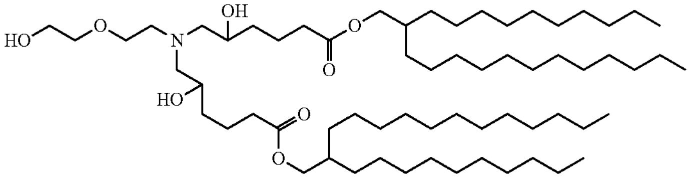 [SMILES: CCCCCCCCCCCCC(CCCCCCCCCC)COC(=O)CCCC(O)CN(CCOCCO)CC(O)CCCC(=O)OCC(CCCCCCCCCC)CCCCCCCCCCCC]
H-5
$^1$H NMR (400 MHz, Chloroform-d) δ 3.94 (d, J = 5.8 Hz, 4H), 3.76-3.53 (m, 8H), 2.99-2.50 (m, 8H), 2.38-2.28 (m, 4H), 1.84-1.50 (m, 12H), 1.46-1.17 (m, 76H), 0.86 (t, J = 6.6 Hz, 12H).
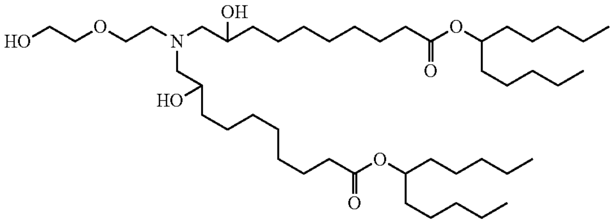 [SMILES: CCCCCC(CCCCC)OC(=O)CCCCCCCC(O)CN(CCOCCO)CC(O)CCCCCCCC(=O)OC(CCCCC)CCCCC]
H-6
$^1$H NMR (400 MHz, Chloroform-d) δ 4.85 (p, J = 6.4 Hz, 2H), 3.81-3.53 (m, 8H), 3.02-2.59 (m, 6H), 2.25 (t, J = 7.5 Hz, 4H), 1.64-1.19 (m, 56H), 0.86 (t, J = 6.5 Hz, 12H).
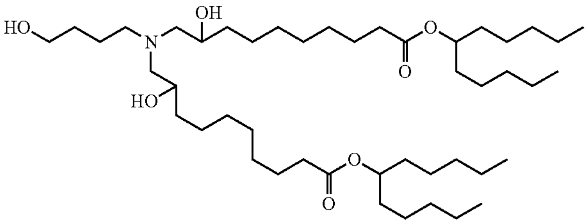 [SMILES: CCCCCC(CCCCC)OC(=O)CCCCCCCC(O)CN(CCCCO)CC(O)CCCCCCCC(=O)OC(CCCCC)CCCCC]
H-7
$^1$H NMR (400 MHz, Chloroform-d) δ 4.85 (p, J = 6.3 Hz, 2H), 3.99-3.86 (m, 2H), 3.71-3:64 (m, 2H), 2.99-2.87 (m, 2H), 2.86-2.74 (m, 3H), 2.61 (d, J = 11.9 Hz, 1H), 2.26 (t, J = 7.5 Hz, 4H), 1.83-1.74 (m, 2H), 1.71-1.19 (m, 58H), 0.94-0.74 (m, 12H).

-continued
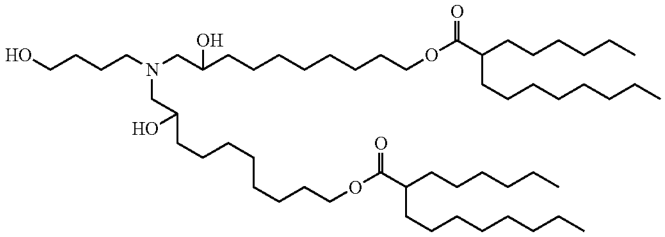 [SMILES: CCCCCCCCC(CCCCCC)C(=O)OCCCCCCCCC(O)CN(CCCCO)CC(O)CCCCCCCCOC(=O)C(CCCCCC)CCCCCCCC]
$^1$H NMR (400 MHz, Chloroform-d) δ 4.04 (t, J = 6.7 Hz, 4H), 3.96-3.86 (m, 2H), 3.71-3.64 (m, 2H), 2.97-2.86 (m, 2H), 2.83-2.72 (m, 3H), 2.59 (d, J = 12.9 Hz, 1H), 2.29 (tt, J = 9.4, 5.3 Hz, 2H), 1.82-1.73 (m, 2H), 1.71-1.64 (m, 2H), 1.63-1.15 (m, 76H), 0.86 (t, J = 6.6 Hz, 12H).
H-8
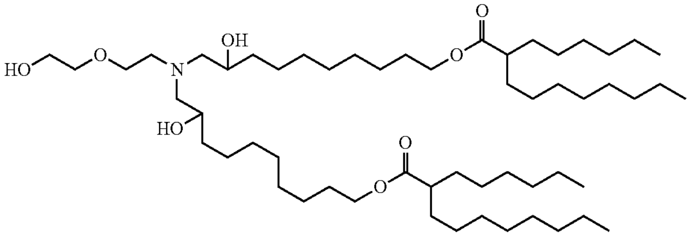 [SMILES: CCCCCCCCC(CCCCCC)C(=O)OCCCCCCCCC(O)CN(CCOCCO)CC(O)CCCCCCCCOC(=O)C(CCCCCC)CCCCCCCC]
$^1$H NMR (400 MHz, Chloroform-d) δ 4.04 (t, J = 6.7 Hz, 4H), 3.80-3.54 (m, 8H), 3.02-2.62 (m, 6H), 2.33-2.24 (m, 2H), 1.70-1.09 (m, 76H), 0.86 (t, J = 6.6 Hz, 12H).
H-9
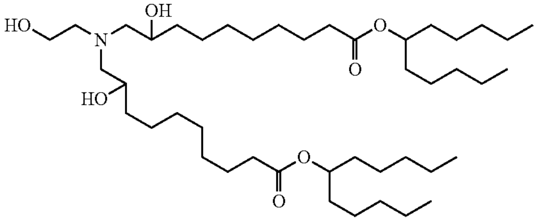 [SMILES: CCCCCC(CCCCC)OC(=O)CCCCCCCC(O)CN(CCO)CC(O)CCCCCCCC(=O)OC(CCCCC)CCCCC]
$^1$H NMR (400 MHz, Chloroform-d) δ 4.85 (p, J = 6.1 Hz, 2H), 3.82-3.63 (m, 4H), 2.94 (s, 1H), 2.81-2.53 (m, 5H), 2.26 (t, J = 7.5 Hz, 4H), 1.66-1.13 (m, 56H), 0.94-0.77 (m, 12H).
H-10
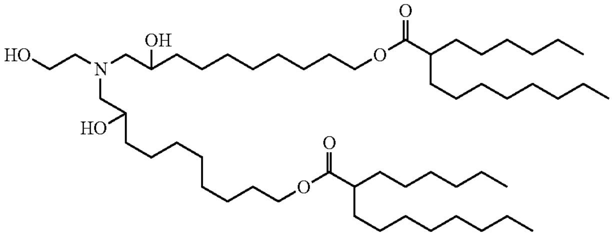 [SMILES: CCCCCCCCC(CCCCCC)C(=O)OCCCCCCCCC(O)CN(CCO)CC(O)CCCCCCCCOC(=O)C(CCCCCC)CCCCCCCC]
$^1$H NMR (400 MHz, Chloroform-d) δ 4.04 (t, J = 6.7 Hz, 4H), 3.92-3.75 (m, 4H), 3.06 (s, 1H), 2.92-2.66 (m, 5H), 2.33-2.24 (m, 2H), 1.67-1.14 (m, 76H), 0.86 (t, J = 6.7 Hz, 12H).
H-11
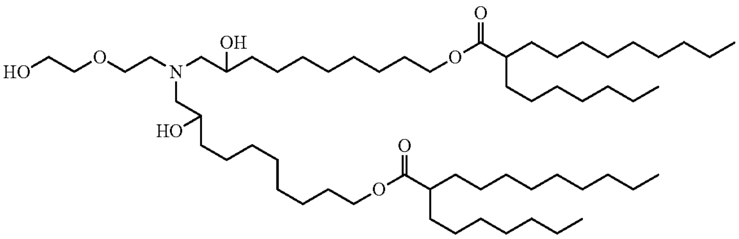 [SMILES: CCCCCCCCCC(CCCCCCC)C(=O)OCCCCCCCCC(O)CN(CCOCCO)CC(O)CCCCCCCCOC(=O)C(CCCCCCC)CCCCCCCCC]
$^1$H NMR (400 MHz, Chloroform-d) δ 4.03 (t, J = 6.7 Hz, 4H), 3.82-3.54 (m, 8H), 2.94-2.50 (m, 6H), 2.27 (t, J = 7.5 Hz, 4H), 1.84-0.98 (m, 82H), 0.93-0.74 (m, 12H).
H-12

-continued
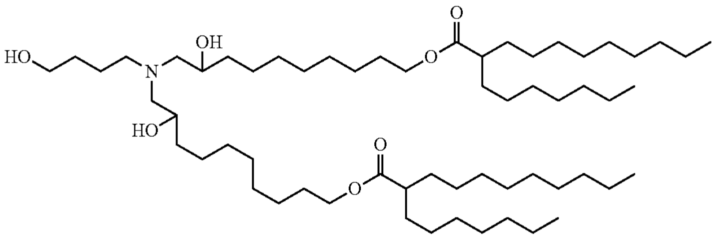 [SMILES: CCCCCCCCCC(CCCCCCC)C(=O)OCCCCCCCCC(O)CN(CCCCO)CC(O)CCCCCCCCOC(=O)C(CCCCCCC)CCCCCCCCC]
$^1$H NMR (400 MHz, Chloroform-d) δ 4.03 (t, J = 6.8 Hz, 4H), 3.99-3.88 (m, 2H), 3.72-3.64 (m, 2H), 2.99-2.77 (m, 5H), 2.63 (d, J = 12.9 Hz, 1H), 2.27 (t, J = 7.5 Hz, 4H), 1.89-0.98 (m, 86H), 0.93-0.75 (m, 12H).
H-13
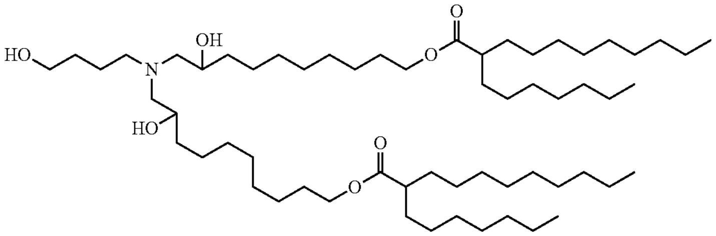 [SMILES: CCCCCCCCCC(CCCCCCC)C(=O)OCCCCCCCCC(O)CN(CCCCO)CC(O)CCCCCCCCOC(=O)C(CCCCCCC)CCCCCCCCC]
$^1$H NMR (400 MHz, Chloroform-d) δ 4.03 (t, J = 6.8 Hz, 4H), 3.86-3.68 (m, 4H), 2.99 (s, 1H), 2.85-2.60 (m, 5H), 2.27 (t, J = 7.5 Hz, 4H), 1.79-0.92 (m, 82H), 0.90-0.75 (m, 12H).
H-14
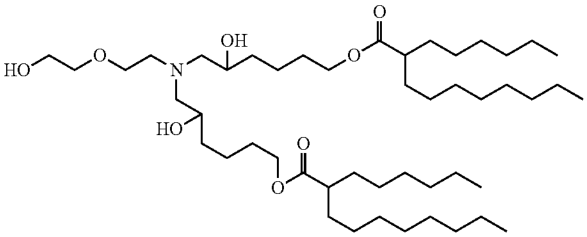 [SMILES: CCCCCCCCC(CCCCCC)C(=O)OCCCCC(O)CN(CCOCCO)CC(O)CCCCOC(=O)C(CCCCCC)CCCCCCCC]
$^1$H NMR (400 MHz, Chloroform-d) δ 4.04 (t, J = 6.5 Hz, 4H), 3.72 (q, J = 4.2 Hz, 2H), 3.68- 3.49 (m, 6H), 3.01-2.21 (m, 8H), 1.69-1.49 (m, 10H), 1.47-1.15 (m, 10H), 1.29-1.32 (m, 40H), 0.85 (t, J = 6.6 Hz, 12H).
H-15
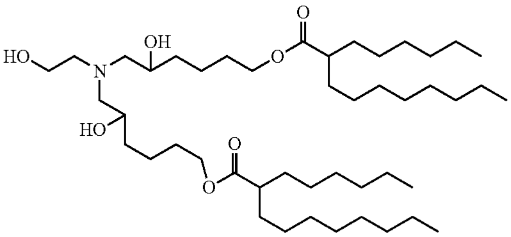 [SMILES: CCCCCCCCC(CCCCCC)C(=O)OCCCCC(O)CN(CCO)CC(O)CCCCOC(=O)C(CCCCCC)CCCCCCCC]
$^1$H NMR (400 MHz, Chloroform-d) δ 4.05 (t, J = 6.6 Hz, 4H), 3.92-3.71 (m, 4H), 3.03 (s, 1H), 2.89-2.63 (m, 5H), 2.29 (tt, J = 9.2, 5.3 Hz, 2H), 1.67-1.16 (m, 60H), 0.86 (t, J = 6.7 Hz, 12H).
H-16
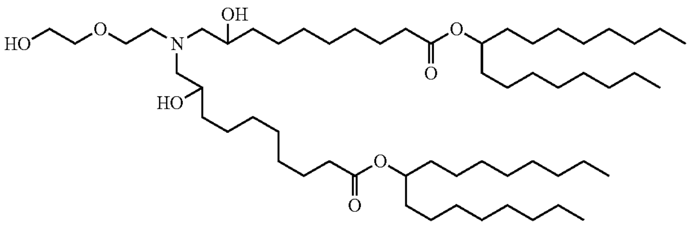 [SMILES: CCCCCCCCC(CCCCCCCC)OC(=O)CCCCCCCC(O)CN(CCOCCO)CC(O)CCCCCCCC(=O)OC(CCCCCCCC)CCCCCCCC]
$^1$H NMR (400 MHz, Chloroform-d) δ 4.84 (p, J = 6.1 Hz, 2H), 3.78-3.55 (m, 8H), 2.94-2.54 (m, 6H), 2.25 (t, J = 7.5 Hz, 4H), 1.71-1.11 (m, 80H), 0.86 (t, J = 6.6 Hz, 12H).
H18

-continued

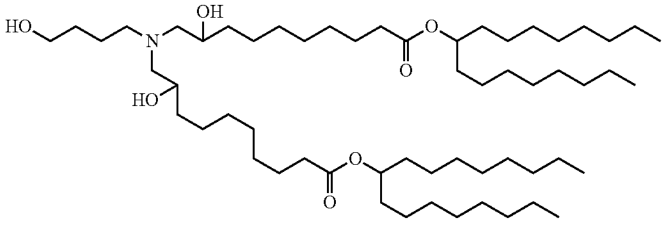 [SMILES: CCCCCCCCC(CCCCCCCC)OC(=O)CCCCCCCC(O)CN(CCCCO)CC(O)CCCCCCCC(=O)OC(CCCCCCCC)CCCCCCCC]

H-19

$^1$H NMR (400 MHz, Chloroform-d) δ 4.84 (p, J = 6.2 Hz, 2H), 3.98-3.85 (m, 2H), 3.71-3.63 (m, 2H), 2.97-2.74 (m, 5H), 2.60 (d, J = 12.9 Hz, 1H), 2.25 (t, J = 7.5 Hz, 4H), 1.83-1.12 (m, 84H), 0.86 (t, J = 6.7 Hz, 12H).

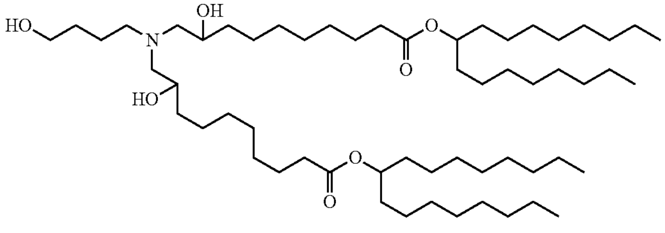 [SMILES: CCCCCCCCC(CCCCCCCC)OC(=O)CCCCCCCC(O)CN(CCCCO)CC(O)CCCCCCCC(=O)OC(CCCCCCCC)CCCCCCCC]

H-20

$^1$H NMR (400 MHz, Chloroform-d) δ 4.84 (p, J = 6.3 Hz, 2H), 3.92-3.73 (m, 4H), 3.05 (s, 1H), 2.92-2.64 (m, 5H), 2.25 (t, J = 7.5 Hz, 4H), 1.69-1.05 (m, 80H), 0.86 (t, J = 6.7 Hz, 12H).

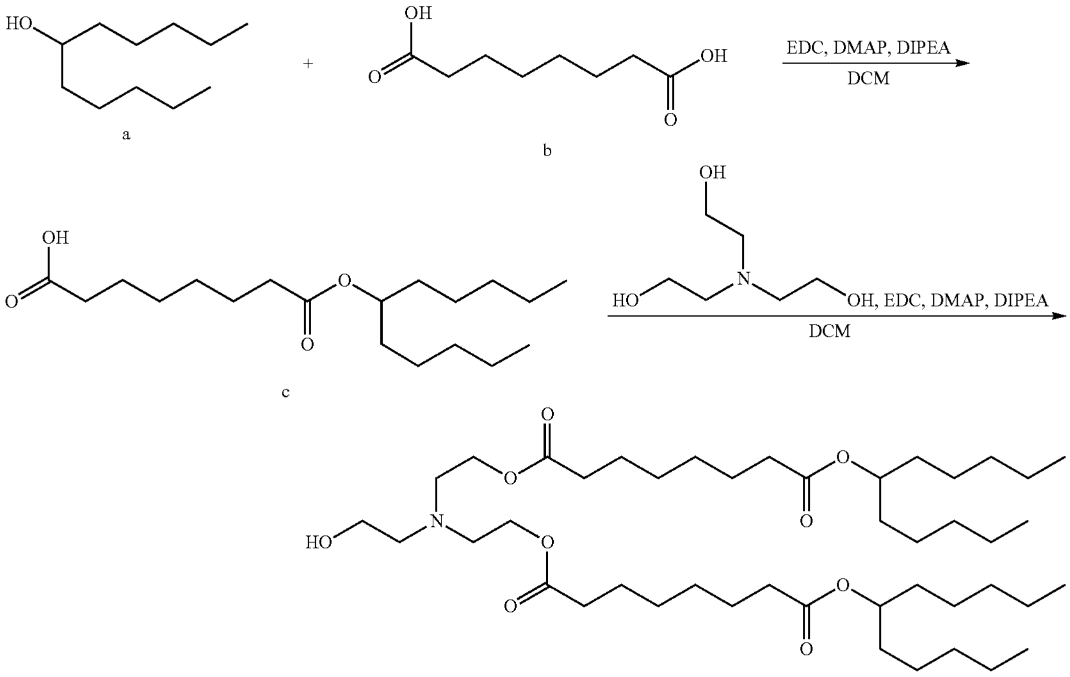

H-21

Example 2

Synthesis of compound c: succinic acid (compound b, 1.52 g, 8.71 mmol) was dissolved in 50 mL of dichloromethane, 1-(3-dimethylaminopropyl)-3-ethylcarbodiimide (EDC, 3.34 g, 17.4 mmol), 4-dimethylaminopyridine (DMAP, 0.3 g, 2.4 mmol) and N,N-diisopropylethylamine (DIPEA, 1.5 g, 11.6 mmol) were added to the solution and stirred for-10 minutes, then 6-undecyl alcohol (compound a, 1 g, 5.8 mmol) was added and stirred at room temperature for 12 hours. After the reaction, monitored by TLC, was completed, the dichloromethane was removed by rotary evaporation, then 100 mL of ethyl acetate was added. The mixture was washed with equal volume of saturated sodium chloride solution for three times, the organic phase was dried by anhydrous sodium sulfate for 30 minutes. After the solvent was removed by rotary evaporation, the residue was purified by column (silica gel column, the eluent was PE: EA=20:1 (volume ratio)) to obtain 1.2 g of colorless liquid, yield: 63%.

Synthesis of compound H-21: compound c (0.88 g, 2.68 mmol) was dissolved in 20 mL of dichloromethane, 1-(3- dimethylaminopropyl)-3-ethylcarbodiimide (EDC, 0.64 g, 3.35 mmol), 4-dimethylaminopyridine (DMAP, 0.065 g, 0.54 mmol) and N, N-diisopropylethylamine (DIPEA, 0.35 g, 2.68 mmol) were added to the solution and stirred for 10 minutes. Triethanolamine (0.2 g, 1.34 mmol) was added and stirred at room temperature for 12 hours. After the reaction, monitored by TLC, was completed, the solvent was removed by rotary evaporation, then 50 mL of ethyl acetate was added. The mixture was washed with saturated sodium chloride solution of an equal volume for three times, then the organic phase was dried with anhydrous sodium sulfate for 30 minutes. After the solvent was removed by rotary evaporation, the residue was purified by column (silica gel column, the eluent was PE: EA=1:1 (volume ratio)) to obtain 0.4 g of colorless liquid, yield: 39%. MS m/z (ESI): 770.71 $[M+H]^+$ The compounds H-21 and H-23 were prepared using the method of Example 2:

| | |
|---|---|
| 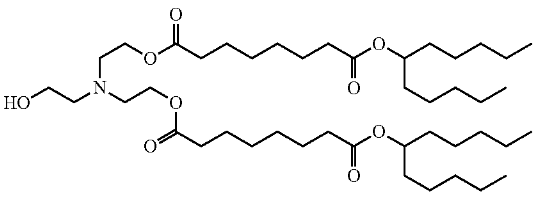 [SMILES: CCCCCC(CCCCC)OC(=O)CCCCCCC(=O)OCCN(CCO)CCOC(=O)CCCCCCC(=O)OC(CCCCC)CCCCC]<br>H-21 | $^1$H NMR (400 MHz, Chloroform-d) δ 4.84 (p, J = 6.3 Hz, 2H), 4.15 (s, 4H), 3.55 (s, 2H), 2.85 (s, 4H), 2.76 (s, 2H), 2.28 (dt, J = 14.1, 7.5 Hz, 8H), 1.66-1.57 (m, 8H), 1.53-1.43 (m, 8H), 1.36-1.18 (m, 32H), 0.94-0.78 (m, 12H). |
| 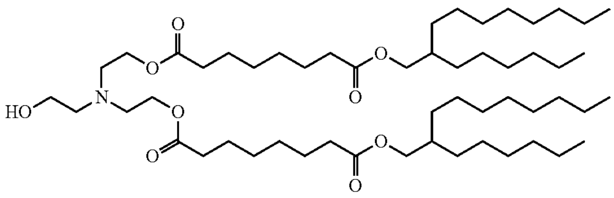 [SMILES: CCCCCCCCC(CCCCCC)COC(=O)CCCCCCC(=O)OCCN(CCO)CCOC(=O)CCCCCCC(=O)OCC(CCCCCC)CCCCCCCC]<br>H-23 | $^1$H NMR (400 MHz, Chloroform-d) δ 4.43-3.82 (m, 8H), 3.55 (s, 2H), 3.08-2.58 (m, 6H), 2.38-2.20 (m, 8H), 1.67-1.58 (m, 8H), 1.36-1.20 (m, 58H), 0.93-0.81 (m, 12H). |

Example 3

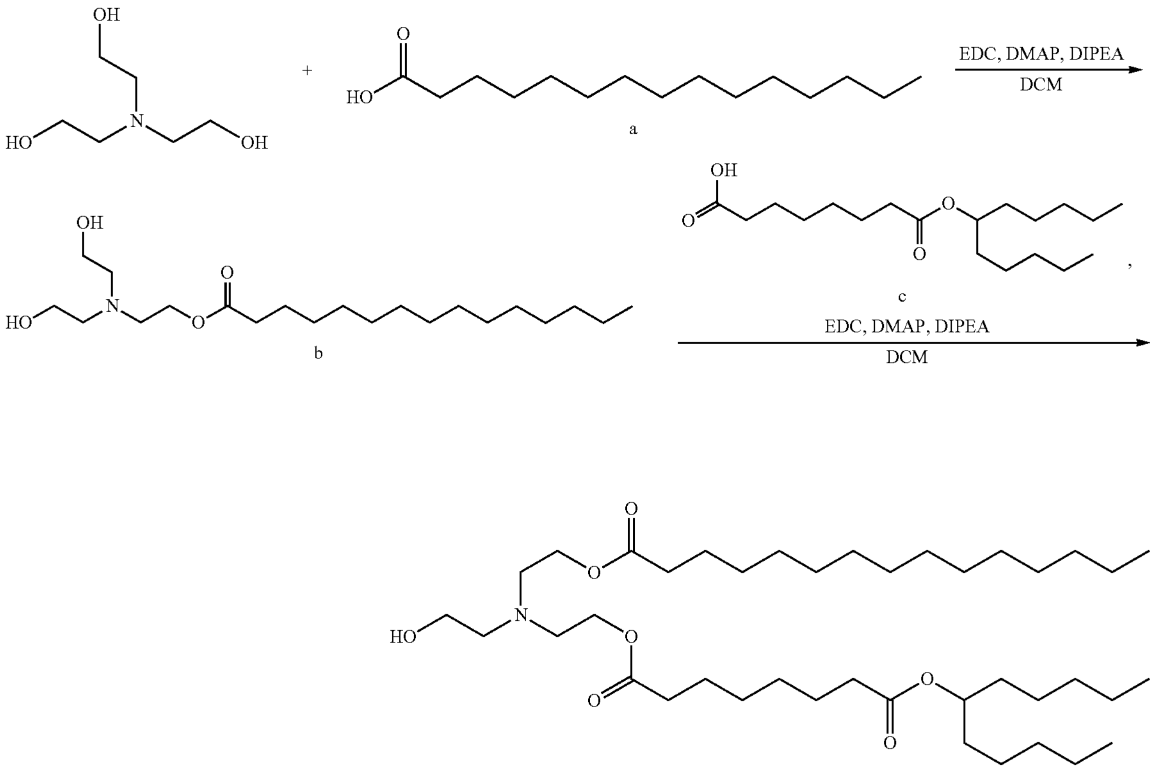

H-22

Synthesis of compound b: Tetradecanoic acid (compound a, 1.57 g, 6.48 mmol) was dissolved in 70 mL of dichloromethane, 1-(3-dimethylaminopropyl)-3-ethylcarbodiimide (EDC, 1.86 g, 9.72 mmol), 4-dimethylaminopyridine (DMAP, 0.32 g, 2.6 mmol), and N,N-diisopropylethylamine (DIPEA, 1.67 g, 12.3 mmol) were added to the solution and stirred for 10 minutes, then triethanolamine (2.9 g, 19.44 mmol) was added and stirred at room temperature for 12 hours. After the reaction, monitored by TLC, was completed, the solvent was removed by rotary evaporation, and 120 mL of ethyl acetate was added. The mixture was washed with equal volume of saturated sodium chloride solution for three times. The organic phase was dried by anhydrous sodium sulfate for 30 minutes, after the solvent was removed by rotary evaporation, the residue was purified by column (silica gel column, the eluent was PE: EA=1:5 (volume ratio)) to obtain 1.8 g of colorless liquid, yield: 74%.

Synthesis of compound c: the compound is synthesized by referring to the method of compound c in Example 2.

Synthesis of compound H-22: compound c (0.88 g, 2.68 mmol) was dissolved in 30 mL of dichloromethane, 1-(3-dimethylaminopropyl)-3-ethylcarbodiimide (EDC, 0.51 g, 2.68 mmol), 4-dimethylaminopyridine (DMAP, 0.13 g, 1.07 mmol) and N,N-diisopropylethylamine (DIPEA, 0.52 g, 4.02 mmol) were added to the solution and stirred for 10 minutes, then compound b (1 g, 2.68 mmol) was added and stirred at room temperature for 12 hours. TLC monitored that the reaction was completed, then the solvent was removed by rotary evaporation, then 70 mL of ethyl acetate was added. The mixture was washed with equal volume of saturated sodium chloride solution for three times, and the organic phase was dried by anhydrous sodium sulfate for 30 minutes. After the solvent was removed by rotary evaporation, the residue was purified by column (silica gel column, the eluent was PE: EA=1:1 (volume ratio)) to obtain 1.0 g of colorless liquid, yield: 55%. MS m/z (ESI): 684.57 $[M+H]^+$ The compounds H-22 and H-24 were prepared by the method of Example 3.

| | |
|---|---|
| 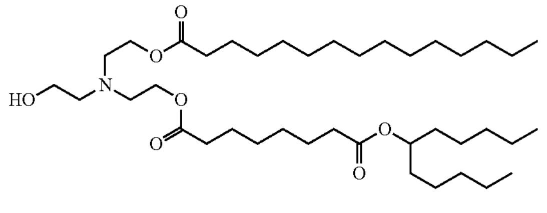 [SMILES: CCCCCCCCCCCCCCC(=O)OCCN(CCO)CCOC(=O)CCCCCCC(=O)OC(CCCCC)CCCCC]<br>H-22 | $^1$H NMR (400 MHz, Chloroform-d) δ 4.85 (t, J = 6.2 Hz, 1H), 4.16 (s, 4H), 3.56 (s, 2H), 3.04-2.66 (m, 6H), 2.39-2.17 (m, 6H), 1.65-1.56 (m, 6H), 1.51-1.44 (m, 4H), 1.36-1.21 (m, 38H), 0.93-0.80 (m, 9H). |
| 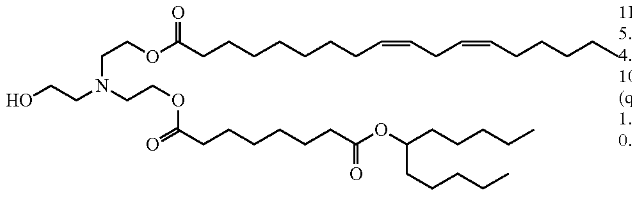<br>H-24 | 1H NMR (400 MHz, Chloroform-d) δ 5.44-5.24 (m, 4H), 4.85 (p, J = 6.3 Hz, 1H), 4.15 (s, 4H), 3.55 (s, 2H), 3.00-2.62 (m, 10H), 2.28 (dt, J = 14.7, 7.6 Hz, 6H), 2.03 (q, J = 6.9 Hz, 4H), 1.65-1.56 (m, 6H), 1.52-1.44 (m, 4H), 1.38-1.18 (m, 28H), 0.92-0.81 (m, 9H). |

Example 4

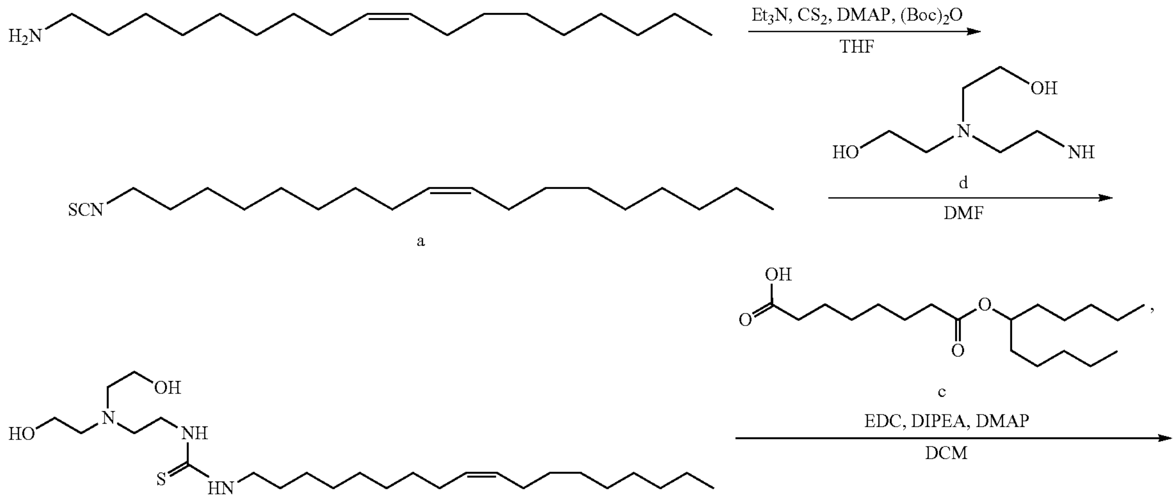

-continued

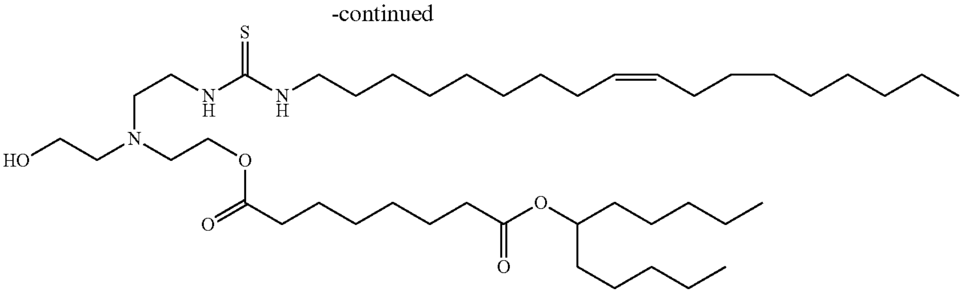

H-25

Synthesis of compound a: oleylamine (2 g, 7.48 mmol) was dissolved in 50 mL of THF, triethylamine (1.13 g, 11.21 mmol) was added to the solution, and $CS_2$ (0.74 g, 9.72 mmol) was added dropwise under ice bath, then the solution was stirred at room temperature for 12 hours. 4-Dimethylaminopyridine (DMAP, 0.27 g, 2.24 mmol) was added, and di-tert-butyl dicarbonate ($(Boc)_2O$, 2.12 g, 9.72 mmol) was added under ice bath condition and stirred at room temperature for 3 hours. TLC monitored that the reaction was completed, then the solvent was removed by rotary evaporation. 100 mL of ethyl acetate was added to the mixture and then washed with equal volume of saturated sodium chloride solution for three times, dried with anhydrous sodium sulfate for 30 minutes. After the solvent was removed by rotary evaporation, the residue was separated and purified by column (silica gel column, the eluent was PE: EA=100:1 (volume ratio)) to obtain 1.78 g of light yellow liquid, yield: 77%.

Synthesis of compound b: compound a (0.5 g, 1.62 mmol) was dissolved in 10 mL of DMF, compound d (0.24 g, 1.62 mmol) was added to the solution and stirred at room temperature for 12 hours. TLC monitored that the reaction was completed, most of the solvent was removed by rotary evaporation. 70 mL of ethyl acetate was added, and the mixture was then washed with equal volume of saturated sodium chloride solution for three times, then dried with anhydrous sodium sulfate for 30 minutes. After the solvent was removed by rotary evaporation, the residue was purified by column (silica gel column, the eluent was PE: EA=1:1 (volume ratio)) to obtain 0.5 g of colorless liquid, yield: 68%.

Synthesis of compound c: the compound is synthesized by referring to the method of compound c in Example 2.

Synthesis of compound H-25: compound c (0.36 g, 1.09 mmol) was dissolved in 20 mL of dichloromethane, 1-(3-dimethylaminopropyl)-3-ethylcarbodiimide (EDC, 0.32 g, 1.64 mmol), 4-dimethylaminopyridine (DMAP, 0.05 g, 0.44 mmol), and N,N-diisopropylethylamine (DIPEA, 0.28 g, 2.81 mmol) were added to the solution and stirred for 10 minutes, then compound b (0.5 g, 1.09 mmol) was added and stirred at room temperature for 12 hours. TLC monitored that the reaction was completed, then the solvent was removed by rotary evaporation. 50 mL of ethyl acetate was added, and the mixture was washed for three times with equal volume of saturated sodium chloride solution, then the organic phase was dried with anhydrous sodium sulfate for 30 minutes. After the solvent was removed by rotary evaporation, the residue was purified by column (silica gel column, the eluent was PE: EA=5:1 (volume ratio)) to obtain 0.5 g of colorless liquid, yield: 60%. MS m/z (ESI): 768.62 $[M+H]^+$.

The compounds H-25, H-26, and H-27 were prepared by the method of Example 4.

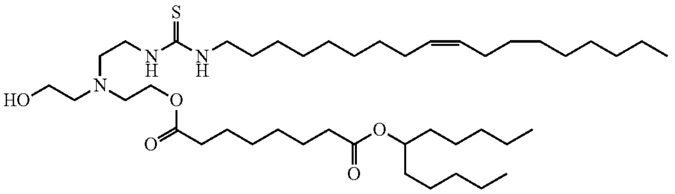 [SMILES: CCCCCCCC/C=C\CCCCCCCCNC(=S)NCCN(CCO)CCOC(=O)CCCCCCC(=O)OC(CCCCC)CCCCC]

H-25

$^1H$ NMR (400 MHz, Chloroform-d) δ 7.02 (s, 1H), 5.46-5.24 (m, 2H), 4.85 (p, J = 6.2 Hz, 1H), 4.30 (t, J = 6.2 Hz, 2H), 3.97-3.75 (m, 6H), 3.57 (dq, J = 7.0, 4.0 Hz, 2H), 2.28 (dt, J = 14.9, 7.4 Hz, 4H), 2.05-1.91 (m, 4H), 1.83-1.70 (m, 2H), 1.65-1.56 (m, 6H), 1.52-1.45 (m, 4H), 1.41-1.16 (m, 42H), 0.90-0.82 (m, 9H).

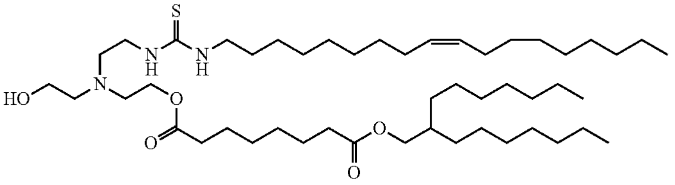 [SMILES: CCCCCCCC/C=C\CCCCCCCCNC(=S)NCCN(CCO)CCOC(=O)CCCCCCC(=O)OCC(CCCCCCC)CCCCCCC]

H-26

$^1H$ NMR (400 MHz, Chloroform-d) δ 7.02 (s, 1H), 5.39-5.29 (m, 2H), 4.30 (t, J = 6.3 Hz, 2H), 3.94 (d, J = 5.8 Hz, 2H), 3.91-3.80 (m, 6H), 3.57 (t, J = 7.4 Hz, 2H), 2.29 (q, J = 7.7 Hz, 4H), 1.99 (q, J = 6.6 Hz, 4H), 1.72 (s, 6H), 1.64-1.56 (m, 7H), 1.38-1.19 (m, 50H), 0.91-0.81 (m, 9H).

-continued

| | |
|---|---|
| 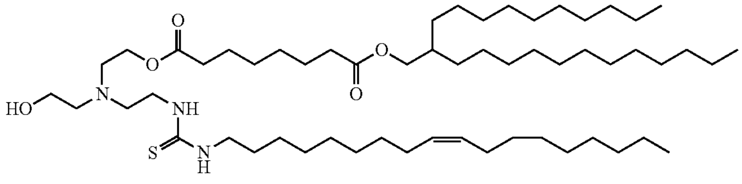 [SMILES: CCCCCCCC/C=C\CCCCCCCCNC(=S)NCCN(CCO)CCOC(=O)CCCCCCC(=O)OCC(CCCCCCCCCC)CCCCCCCCCCCC]<br>H-27 | $^1$H NMR (400 MHz, Chloroform-d) δ 7.01 (s, 1H), 5.38-5.27 (m, 2H), 4.31 (t, J = 6.3 Hz, 2H), 3.96-3.80 (m, 8H), 3.62-3.53 (m, 2H), 2.29 (q, J = 8.0 Hz, 4H), 2.04-1.91 (m, 4H), 1.78-1.55 (m, 14H), 1.36-1.17 (m, 65H), 0.86 (t, J = 6.6 Hz, 9H). |

Example 5

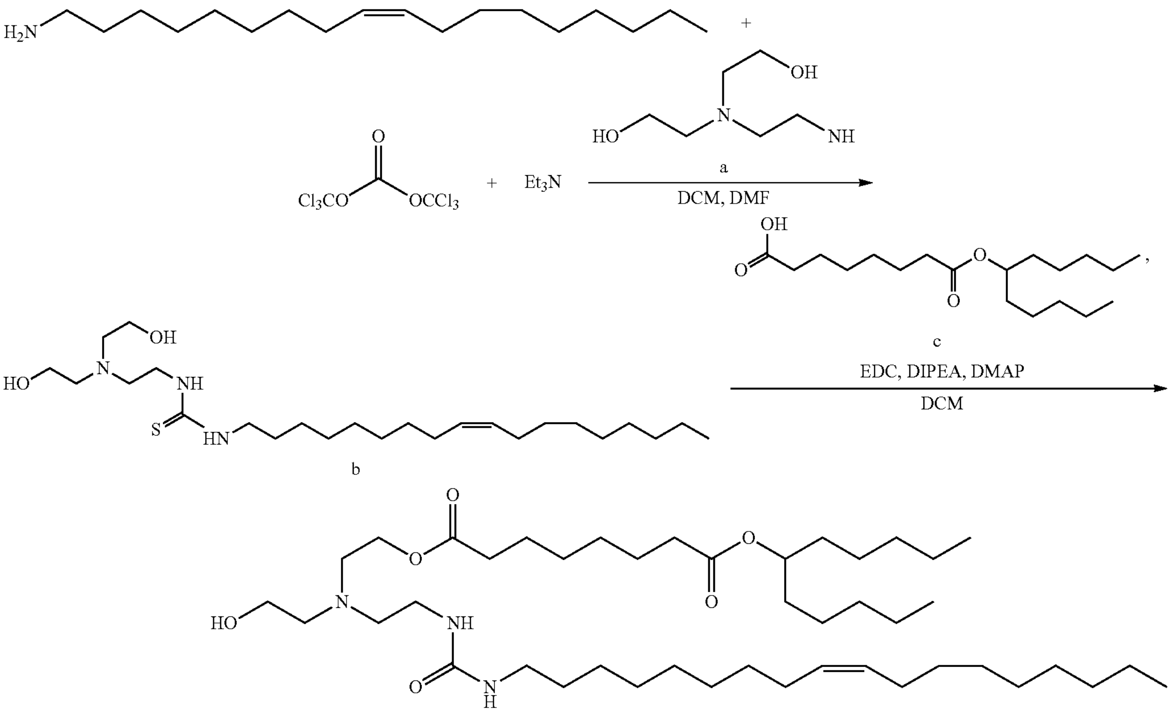

H-28

Synthesis of compound b: oleyamine (1 g, 3.74 mmol) was dissolved in 50 mL of DCM, triethylamine (1.13 g, 11.21 mmol) was added to the solution, and triphosgene (0.44 g, 1.5 mmol) was added dropwise under ice bath condition, then stirred at room temperature for 3 hours. TLC monitored that the reaction was completed, the solvent was removed by rotary evaporation. 30 mL of DMF and compound a (1.11 g, 7.48 mmol) were added to the solution and stirred at room temperature for 12 hours. TLC monitored that the reaction was completed, most of the solvent was removed by rotary evaporation. 100 mL of ethyl acetate was added, and the mixture was washed with equal volume of saturated sodium chloride solution for three times, then dried with anhydrous sodium sulfate for 30 minutes. After the solvent was removed by rotary evaporation, the residue was purified by column (silica gel column, the eluent was PE: EA=1:1 (volume ratio)) to obtain 1.0 g of light yellow liquid, yield: 61%.

Synthesis of compound c: the compound is synthesized by referring to the method of compound c in Example 2.

Synthesis of compound H-28: compound c (0.5 g, 1.52 mmol) was dissolved in 20 mL of dichloromethane, 1-(3-dimethylaminopropyl)-3-ethylcarbodiimide (EDC, 0.44 g, 2.28 mmol), 4-dimethylaminopyridine (DMAP, 0.07 g, 0.61 mmol) and N,N-diisopropylethylamine (DIPEA, 0.39 g, 3.04 mmol) were added and stirred for 10 minutes, then compound b (0.67 g, 1.52 mmol) was added to the solution and stirred at room temperature for 12 hours. TLC monitored that the reaction was completed, then the solvent was removed by rotary evaporation. 100 mL of ethyl acetate was added, and the mixture was washed with equal volume of saturated sodium chloride solution for three times. The organic phase was dried with anhydrous sodium sulfate for 30 minutes. After the solvent was removed by rotary evaporation, the residue was purified by column (silica gel column, the eluent was PE: EA=5:1 (volume ratio)) to obtain 0.4 g of colorless liquid, yield: 35%. MS m/z (ESI): 752.64 $[M+H]^+$.

The compounds H-28 and H-29 were prepared by the method of Example 5.

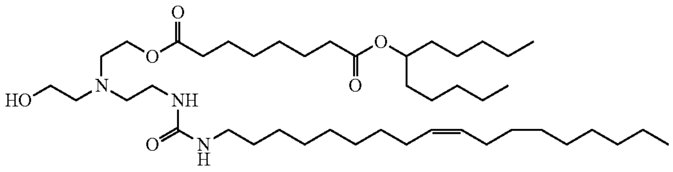 [SMILES: CCCCCCCC/C=C\CCCCCCCCNC(=O)NCCN(CCO)CCOC(=O)CCCCCCC(=O)OC(CCCCC)CCCCC]

H-28

$^1$H NMR (400 MHz, Chloroform-d) δ 5.39-5.27 (m, 2H), 4.85 (dt, J = 12.0, 6.1 Hz, 1H), 4.18 (t, J = 6.1 Hz, 2H), 3.77-3.72 (m, 2H), 3.49-3.40 (m, 4H), 3.18 (t, J = 7.3 Hz, 2H), 2.28 (dt, J = 14.7, 7.4 Hz, 4H), 2.06-1.81 (m, 8H), 1.66-1.55 (m, 4H), 1.53-1.44 (m, 6H), 1.35-1.19 (m, 38H), 0.92-0.76 (m, 9H).

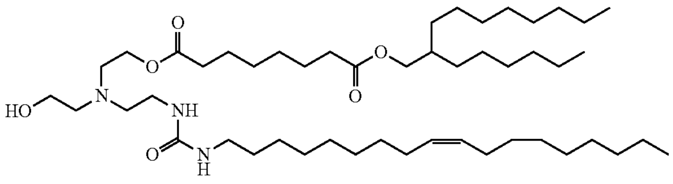 [SMILES: CCCCCCCC/C=C\CCCCCCCCNC(=O)NCCN(CCO)CCOC(=O)CCCCCCC(=O)OCC(CCCCCC)CCCCCCCC]

H-29

$^1$H NMR (400 MHz, Chloroform-d) δ 5.40-5.26 (m, 2H), 4.18 (t, J = 6.1 Hz, 2H), 3.95 (d, J = 6.0 Hz, 2H), 3.74 (s, 2H), 3.51-3.38 (m, 4H), 3.18 (t, J = 7.2 Hz, 2H), 2.29 (q, J = 8.3, 7.9 Hz, 4H), 2.24-1.88 (m, 8H), 1.66-1.55 (m, 5H), 1.53-1.45 (m, 2H), 1.42-1.16 (m, 50H), 0.93-0.79 (m, 9H).

Example 6

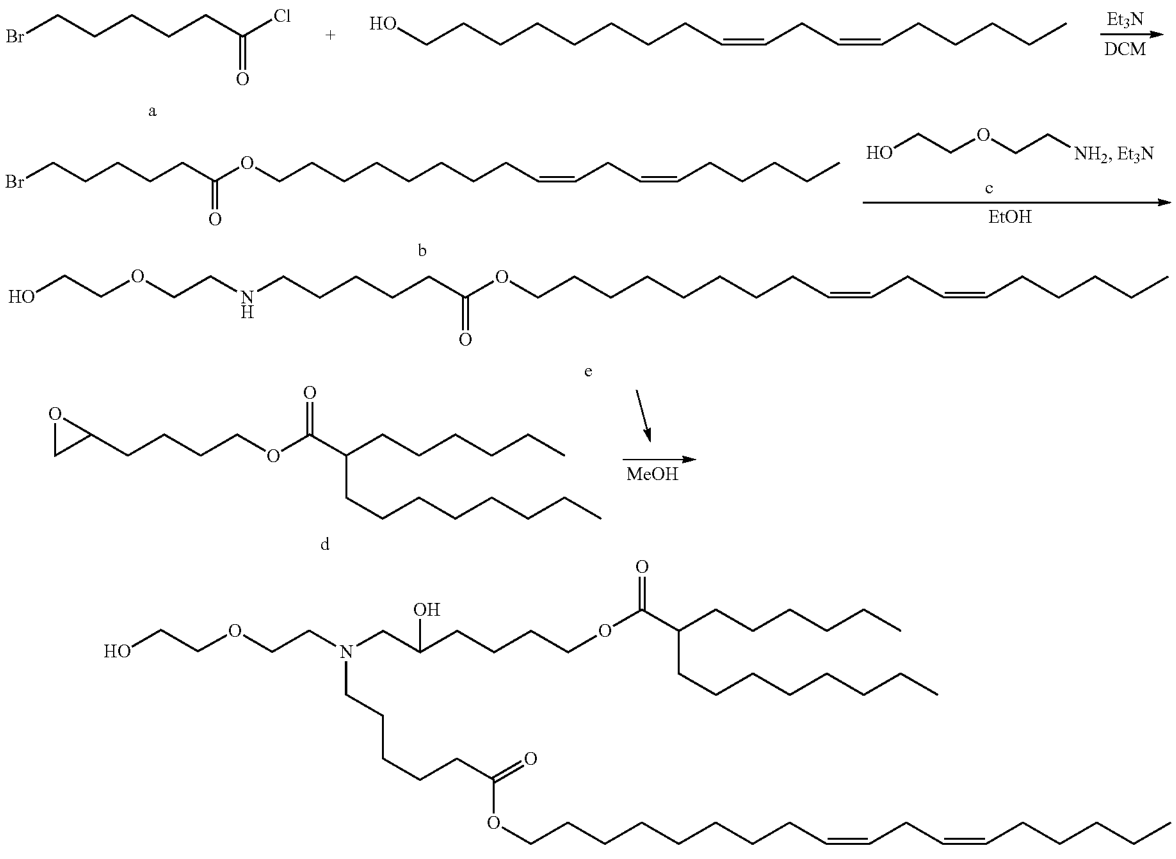

H-17

Synthesis of compound b: linoleic acid (1.25 g, 4.68 mmol) was dissolved in 50 mL of DCM, triethylamine (0.62 g, 6.09 mmol) was added and stirred in an ice bath for 10 minutes, then 6-bromohexanoyl chloride (compound a, 1 g, 4.68 mmol) was added dropwise, gradually returned to room temperature, then stirred at room temperature for 12 hours. TLC monitored that the reaction was completed, the solvent was removed by rotary evaporation. 100 mL of ethyl acetate was added, and the mixture was washed with equal volume of saturated sodium bicarbonafe solution for three times, then washed with equal volume of saturated sodium chloride solution for three times, and dried by anhydrous sodium sulfate for 30 minutes. After the solvent was removed by rotary evaporation, the residue was purified by column (silica gel column, the eluent was PE: EA=20:1 (volume ratio)) to obtain 1.8 g of colorless liquid, yield: 87%.

Synthesis of compound d: refer to the synthesis method of compound d in the synthesis of compound H-15.

Synthesis of compound e: compound b (1.5 g, 3.38 mmol) dissolved in 50 mL of anhydrous ethanol, triethylamine (0.44 g, 4.4 mmol) and compound c (1.07 g, 10.25 mmol) were added to the solution, heated at 50° C. and stirred for 24 hours. TLC monitored that the reaction was completed, then the solvent was removed by rotary evaporation. 100 mL of ethyl acetate was added, and the mixture was washed with equal volume of saturated sodium chloride for three times, then dried with anhydrous sodium sulfate for 30 minutes. After the solvent was removed by rotary evaporation, the residue was purified by column (silica gel column, the eluent was DCM: MeOH=20:1 (volume ratio)) to obtain 1.1 g of colorless liquid, yield: 70%.

Synthesis of compound H-17: compound e (0.4 g, 0.85 mmol) was dissolved in 10 mL of absolute ethyl alcohol, compound d (0.3 g, 0.85 mmol) was added and stirred for 10 minutes, then heated to reflux for 12 hours. TLC monitored that the reaction was completed, the solvent was removed by rotary evaporation, then the residue was separated and purified by column (silica gel column, the eluent was PE: EA=5:1 (volume ratio)) to obtain 0.4 g of colorless liquid, yield: 57%. MS m/z (ESI): 822.72 $[M+H]^+$ The compound H-17 was prepared using the method of Example 6.

| | |
|---|---|
| 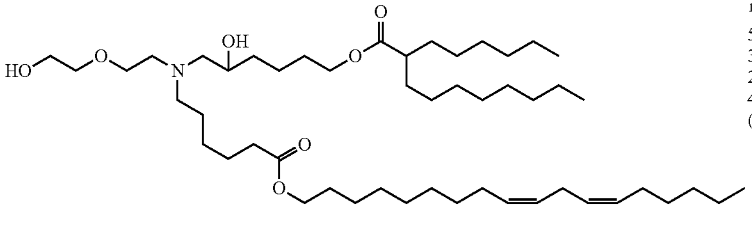 H-17 | $^1$H NMR (400 MHz, Chloroform-d) δ 5.42-5.28 (m, 4H), 4.10-4.00 (m, 4H), 3.79-3.49 (m, 7H), 2.76 (t, J = 6.5 Hz, 2H), 2.65-2.44 (m, 3H), 2.37-2.24 (m, 4H), 2.03 (q, J = 6.9 Hz, 4H), 1.69-1.19 (m, 56H), 0.86 (q, J = 6.6 Hz, 9H). |

Example 7

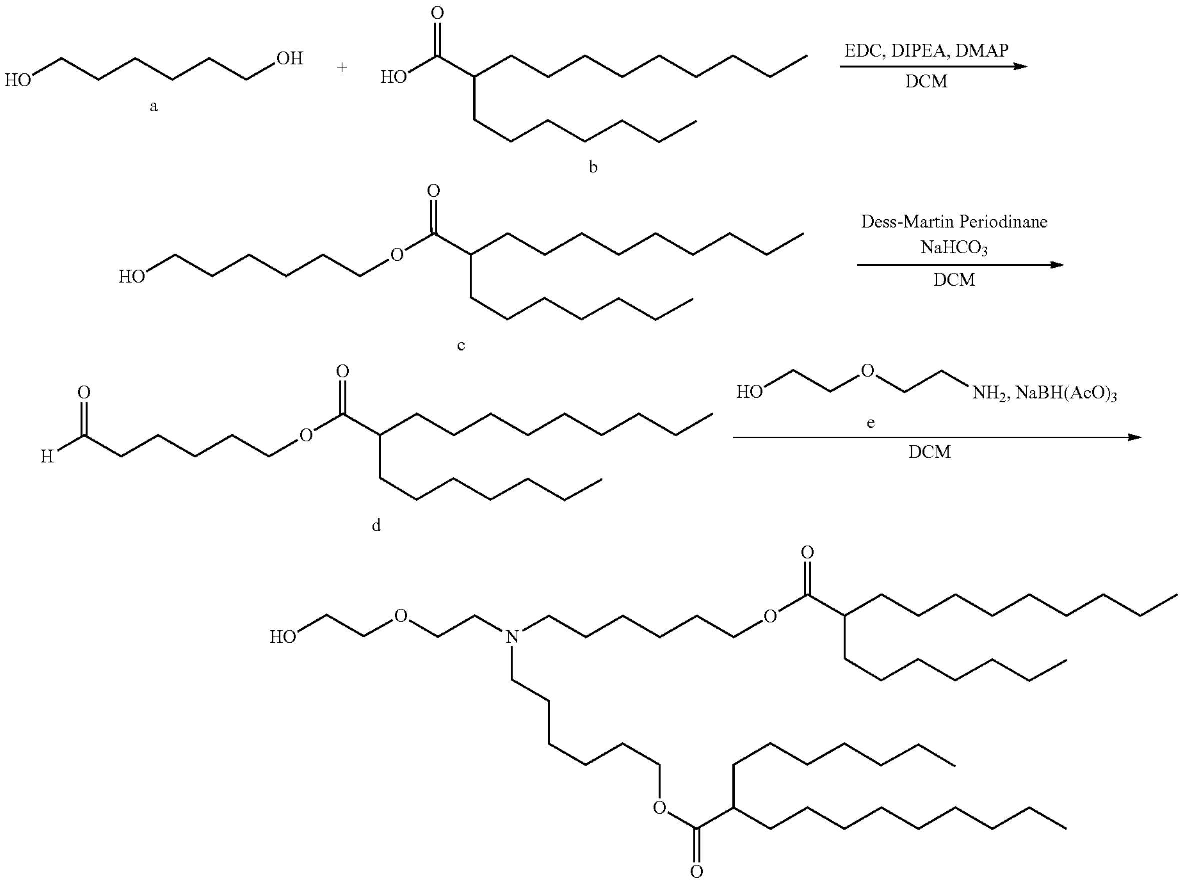

H-15

Synthesis of compound c: compound b (1.6 g, 5.64 mmol) dissolved in 50 mL of dichloromethane, 1-(3-dimethylaminopropyl)-3-ethyl carbodiimide (EDC, 1.3 g, 6.77 mmol), 4-dimethylaminopyridine (DMAP, 0.28 g, 2.26 mmol) and N,N-diisopropylethylamine (DIPEA, 1.09 g, 8.46 mmol) were added and stirred for 10 minutes, then hexanediol (compound a, 1 g, 8.46 mmol) was added and stirred at room temperature for 12 hours. TLC monitored that the reaction was completed, then the solvent was removed by rotary evaporation. 100 mL of ethyl acetate was added, and the mixture was washed with equal volume of saturated sodium chloride solution for three times. The organic phase was dried with anhydrous sodium sulfate for 30 minutes. After the solvent was removed by rotary evaporation, the residue was purified by column (silica gel column, the eluent was PE: EA=50:1 (volume ratio)) to obtain 1.5 g of colorless liquid, yield: 69%.

Compound d (1.0 g, 2.6 mmol) was dissolved in 50 mL of DCM, $NaHCO_3$ (1.75 g, 20.8 mmol) was added and stirred for 5 minutes, then compound Dess-Martin Periodinane (1.75 g, 4.16 mmol) was added and stirred at room temperature for 3 hours. TLC monitored that the reaction was completed, the solvent was removed by rotary evaporation. The petroleum ether was added, and the mixture was washed three times with equal volume of saturated sodium bicarbonate solution, then washed once with equal volume of saturated salt solution. The organic phase was dried with anhydrous sodium sulfate for 30 minutes. After the solvent was removed by rotary evaporation, the residue was purified by column (silica gel column, the eluent was PE: EA=10:1 (volume ratio)) to obtain 0.5 g of colorless liquid, yield: 50%.

Synthesis of compound H-2: compound d (0.3 g, 0.78 mmol) was dissolved in 10 mL of DCM, compound e (0.08 g, 0.78 mmol) was added to the solution and stirred for 10 minutes, then sodium triacetoxyborohydride (0.22 g, 1.02 mmol) was added and stirred overnight at room temperature. TLC monitored that the reaction was completed, the solvent was removed by rotary evaporation. 50 mL of ethyl acetate was added, and the mixture was washed with equal volume of saturated sodium chloride solution for three times. The organic phase was dried with anhydrous sodium sulfate for 30 minutes. The solvent was removed by rotary evaporation, and the residue was purified by column (silica gel column, the eluent was PE: EA=5:1 (volume ratio)) to obtain 0.3 g of colorless liquid, yield: 46%. MS m/z (ESI): 838.79 [M+H]+

The compound H-2 was prepared by the method of Example 7.

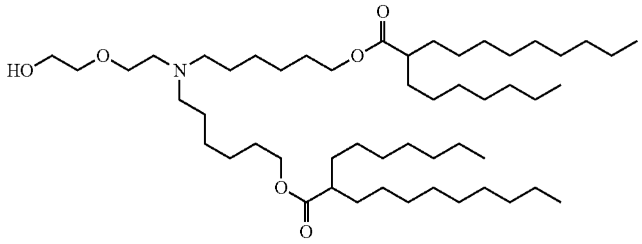 [SMILES: CCCCCCCCCC(CCCCCCC)C(=O)OCCCCCCN(CCCCCCOC(=O)C(CCCCCCC)CCCCCCCCC)CCOCCO]

H-2

$^1H$ NMR (400 MHz, Chloroform-d) δ 4.03 (t, J = 6.7 Hz, 4H), 3.75-3.55 (m, 6H), 2.75-2.38 (m, 6H), 2.27 (t, J = 7.5 Hz, 4H), 1.77-0.96 (m, 70H), 0.91-0.75 (m, 12H).

Example 8

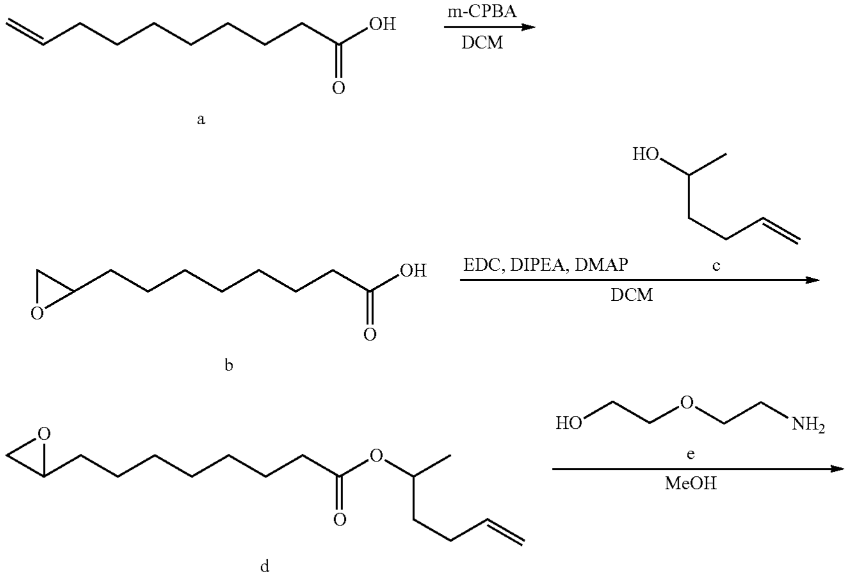

-continued

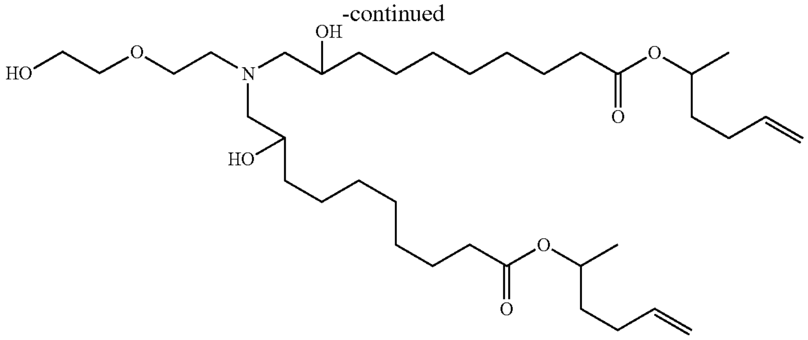

H-30

Synthesis of compound b: compound a (5 g, 29 mmol) was dissolved in 100 mL of DCM, meta-Chloroperbenzoic acid (m-CPBA, 8.9 g, 44 mmol, mass fraction 85%) was added to the solution under ice bath conditions and stirred for 15 minutes, then the ice bath was removed and the mixture was stirred overnight. TLC monitored that the reaction was completed, excess saturated sodium bisulfite solution (10 mL) was added to consume the unreacted meta-Chloroperbenzoic acid, and DCM was removed by rotary evaporation. 200 mL of ethyl acetate was added, washed with 200 mL of saturated sodium bicarbonate solution for three times, then washed with 200 mL of saturated sodium chloride solution for one time. The organic phase was dried with anhydrous sodium sulfate for 30 minutes, after the ethyl acetate was removed by rotary evaporation, the residue was purified by column (silica gel column, the eluent was PE: EA=1:2 (volume ratio)) to obtain 4.5 g of colorless liquid, yield: 82%.

Synthesis of compound d: compound b (3.0 g, 16 mmol) was dissolved in 50 mL of dichloromethane (DCM), 1-(3-dimethylaminopropyl)-3-ethylcarbodiimide (EDC, 4.01 g, 21 mmol), 4-dimethylaminopyridine (DMAP, 0.79 g, 6 mmol), and N,N-diisopropylethylamine (DIPEA, 3.12 g, 24 mmol) were added and stirred for 10 minutes, then hex-5-en-2-ol (compound c, 1.94 g, 19 mmol) was added and stirred overnight at room temperature. TLC monitored that the reaction was completed, then dichloromethane was removed by rotary evaporation. 100 mL of ethyl acetate was added, washed with equal volume of saturated sodium chloride solution for three times. The organic phase was dried with anhydrous sodium sulfate for 30 minutes. After the ethyl acetate was removed by rotary evaporation, the residue was purified by column (silica gel column, the eluent was PE: EA=20:1 (volume ratio)) to obtain 3.5 g of colorless liquid, yield: 81%.

Synthesis of compound H-30: diethylenetriamine (compound e, 0.65 g, 6 mmol) was dissolved in anhydrous methanol, compound d (5 g, 0.19 mmol) was added to the solution and stirred at room temperature for 10 minutes, then heated to reflux for 12 hours. TLC monitored that the reaction was completed, then the solvent was removed by rotary evaporation. The residue was purified by column (silica gel column, the eluent was DCM: MeOH=100:1 (volume ratio)) resulted in 3.0 g of colorless liquid, yield: 75%. MS m/z (ESI): 642.47 $[M+H]^+$.

The compounds H-30 and H-31 were prepared using the method of Example 8:

H-30

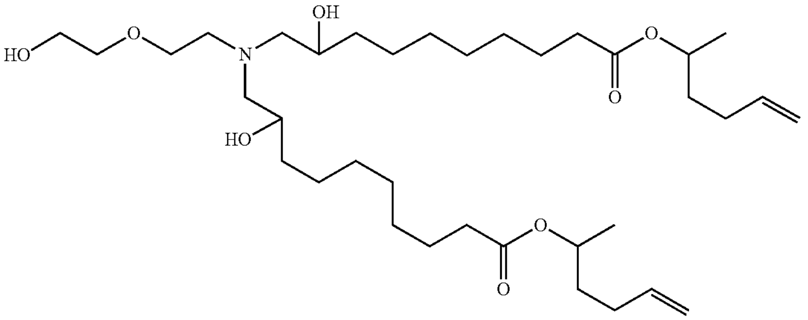

-continued

H-31

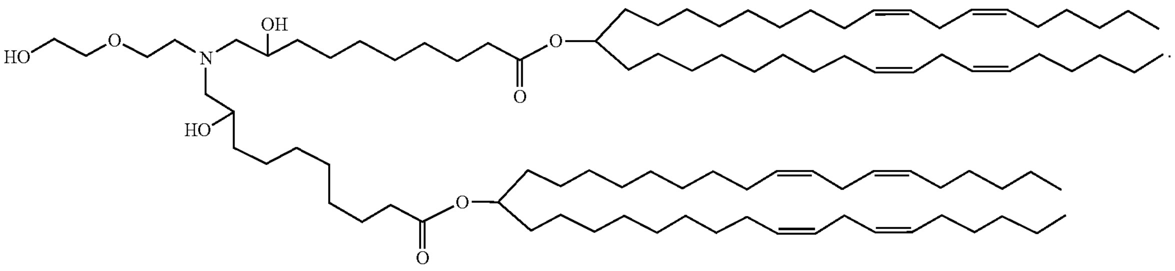

It should be noted that the aforementioned compounds are not exhaustive, and any cationic lipid compounds adopting the synthetic method described in this invention (with a hydroxyl group in the head part and having a small head part and a large tail part) fall within the scope of protection of this invention. The "small head part and a large tail part" mean that when the N atom is taken as a center, the molecular structure space occupied by the head part with hydroxyl group is smaller than that occupied by the tail part with alkane chain at the end.

Experimental Example 1: Preparation and Detection of the LNPs

Compounds H-1 through H-29 were used to prepare mRNA-LNP for the following experiments: The cationic lipids, DSPC or DOPE (AVT (Shanghai) Pharmaceutical Tech Co., Ltd.), cholesterol (AVT (Shanghai) Pharmaceutical Tech Co., Ltd.), and PEG lipids were dissolved in ethanol (Lipid concentration 20 mg/mL) according to the designed prescription ratio (Lipid (cationic lipid compound)/DOPC/Cholesterol/DMG-PEG (conjugated lipid) a molar ratio of 40/10/50/1.7), then the solution was mixed thoroughly. The mass ratio of LNPs to mRNA ranges from 10:1 to 30:1. mRNA was diluted to 0.2 mg/mL using citrate or sodium acetate buffer (pH=3 or 5). The aforementioned lipid ethanol solution and mRNA solution were mixed thoroughly at a volume ratio ranging from 1:5 to 1:1. The yielded nanoparticles were purified by ultrafiltration and dialysis, followed by filtration and sterilization. The particle size and particle dispersion index (PDI) of mRNA-LNPs (mRNA loaded LNPs) were characterized by dynamic light scattering using Malvern Zetasizer Nano ZS in 173 reverse phase scattering detection mode. The particle dispersion index represents the degree of particle size uniformity and is an important index for particle size characterization. The encapsulation efficiency of mRNA was detected using the Ribogreen RNA quantification kit (Thermo Fisher), and the results are shown in Table 1.

TABLE 1

| mRNA-LNP Sample | Structure of the cationic lipid | Size (nm) | PDI (particle dispersion index) | Encapsulation efficiency (%) |
|---|---|---|---|---|
| Sample 1 | 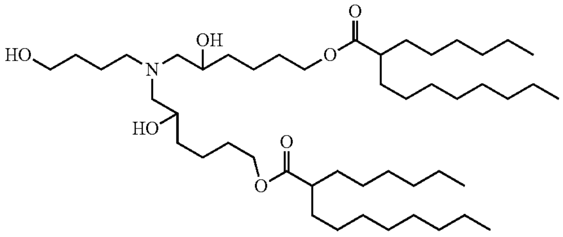 [SMILES: CCCCCCCCC(CCCCCC)C(=O)OCCCCC(O)CN(CCCCO)CC(O)CCCCOC(=O)C(CCCCCC)CCCCCCCC] | 85.25 | 0.112 | 96.1 |
| Sample 2 | 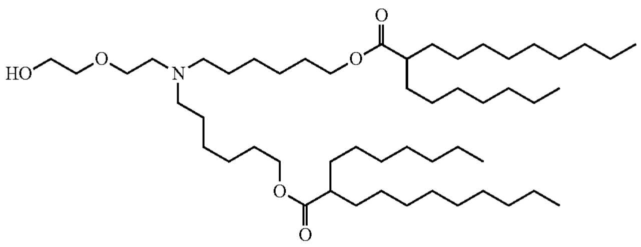 [SMILES: CCCCCCCCCC(CCCCCCC)C(=O)OCCCCCCN(CCCCCCOC(=O)C(CCCCCCC)CCCCCCCCC)CCOCCO] | 91.23 | 0.134 | 92.2 |

TABLE 1-continued
| mRNA-LNP Sample | Structure of the cationic lipid | Size (nm) | PDI (particle dispersion index) | Encapsulation efficiency (%) |
|---|---|---|---|---|
| Sample 3 | 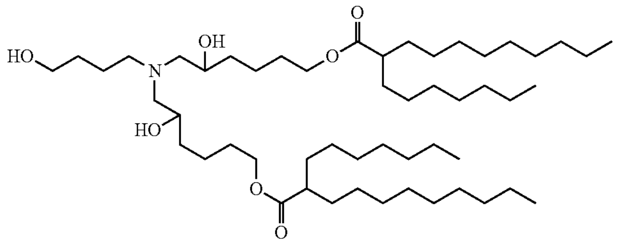 [SMILES: CCCCCCCCCC(CCCCCCC)C(=O)OCCCCC(O)CN(CCCCO)CC(O)CCCCOC(=O)C(CCCCCCC)CCCCCCCCC] | 93.23 | 0.126 | 93.4 |
| Sample 4 | 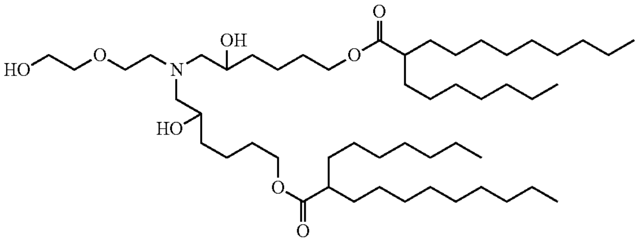 [SMILES: CCCCCCCCCC(CCCCCCC)C(=O)OCCCCC(O)CN(CCOCCO)CC(O)CCCCOC(=O)C(CCCCCCC)CCCCCCCCC] | 92.14 | 0.136 | 89.1 |
| Sample 5 | 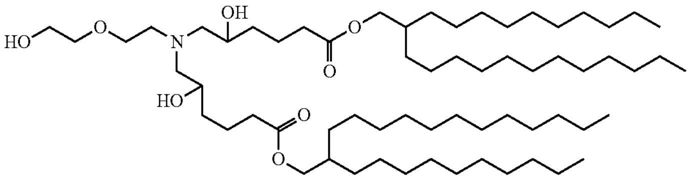 [SMILES: CCCCCCCCCCCCC(CCCCCCCCCC)COC(=O)CCCC(O)CN(CCOCCO)CC(O)CCCC(=O)OCC(CCCCCCCCCC)CCCCCCCCCCCC] | 82.26 | 0.118 | 86.2 |
| Sample 6 | 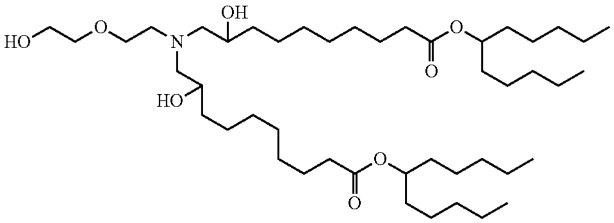 [SMILES: CCCCCC(CCCCC)OC(=O)CCCCCCCC(O)CN(CCOCCO)CC(O)CCCCCCCC(=O)OC(CCCCC)CCCCC] | 80.51 | 0.125 | 94.7 |
| Sample 7 | 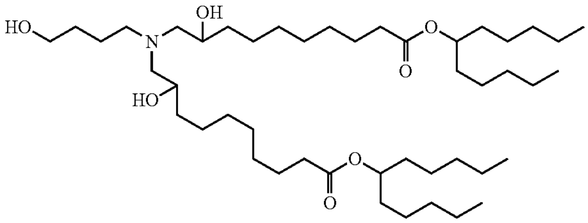 [SMILES: CCCCCC(CCCCC)OC(=O)CCCCCCCC(O)CN(CCCCO)CC(O)CCCCCCCC(=O)OC(CCCCC)CCCCC] | 78.32 | 0.141 | 90.8 |
| Sample 8 | 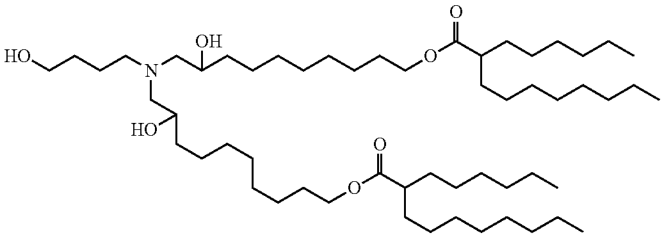 [SMILES: CCCCCCCCC(CCCCCC)C(=O)OCCCCCCCCC(O)CN(CCCCO)CC(O)CCCCCCCCOC(=O)C(CCCCCC)CCCCCCCC] | 98.45 | 0.131 | 91.3 |

TABLE 1-continued
| mRNA-LNP Sample | Structure of the cationic lipid | Size (nm) | PDI (particle dispersion index) | Encapsulation efficiency (%) |
|---|---|---|---|---|
| Sample 9 | 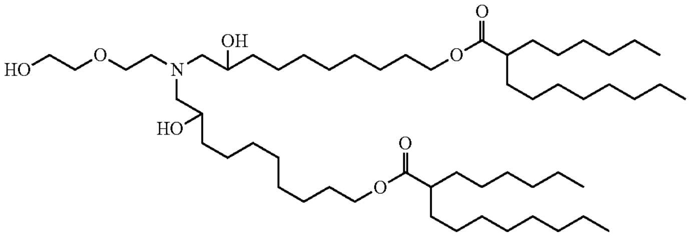 [SMILES: CCCCCCCCC(CCCCCC)C(=O)OCCCCCCCCC(O)CN(CCOCCO)CC(O)CCCCCCCCOC(=O)C(CCCCCC)CCCCCCCC] | 105.18 | 0.137 | 96.5 |
| Sample 10 | 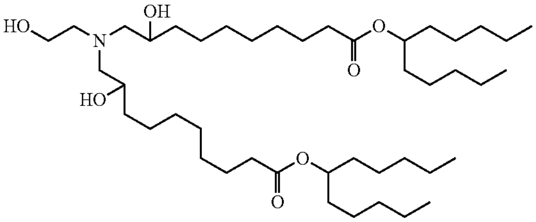 | 87.55 | 0.125 | 94.2 |
| Sample 11 | 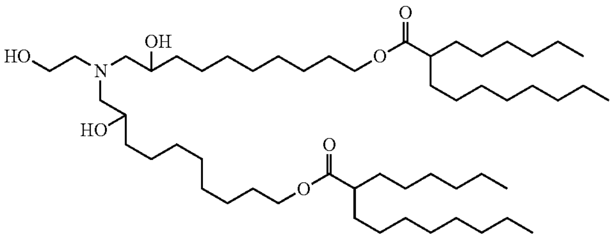 [SMILES: CCCCCCCCC(CCCCCC)C(=O)OCCCCCCCCC(O)CN(CCO)CC(O)CCCCCCCCOC(=O)C(CCCCCC)CCCCCCCC] | 79.89 | 0.127 | 91.1 |
| Sample 12 | 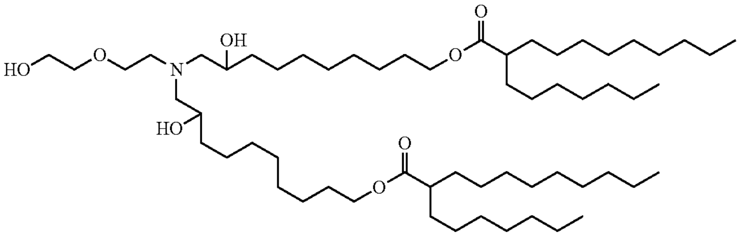 [SMILES: CCCCCCCCCC(CCCCCCC)C(=O)OCCCCCCCCC(O)CN(CCOCCO)CC(O)CCCCCCCCOC(=O)C(CCCCCCC)CCCCCCCCC] | 85.58 | 0.135 | 92.3 |
| Sample 13 | 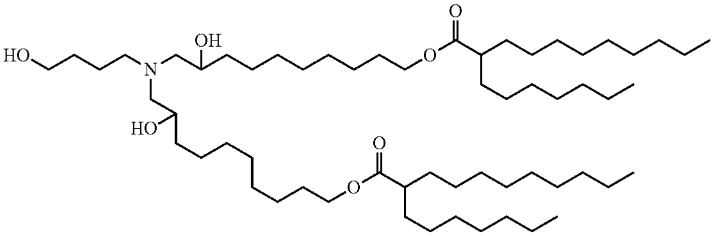 [SMILES: CCCCCCCCCC(CCCCCCC)C(=O)OCCCCCCCCC(O)CN(CCCCO)CC(O)CCCCCCCCOC(=O)C(CCCCCCC)CCCCCCCCC] | 91.63 | 0.126 | 93.6 |
| Sample 14 | 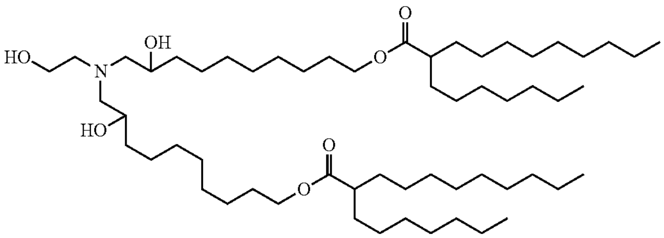 [SMILES: CCCCCCCCCC(CCCCCCC)C(=O)OCCCCCCCCC(O)CN(CCO)CC(O)CCCCCCCCOC(=O)C(CCCCCCC)CCCCCCCCC] | 97.18 | 0.133 | 91.3 |

TABLE 1-continued
| mRNA-LNP Sample | Structure of the cationic lipid | Size (nm) | PDI (particle dispersion index) | Encapsulation efficiency (%) |
|---|---|---|---|---|
| Sample 15 | 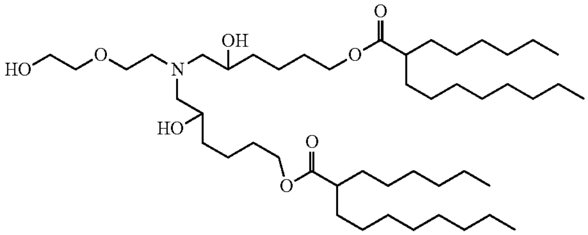 [SMILES: CCCCCCCCC(CCCCCC)C(=O)OCCCCC(O)CN(CCOCCO)CC(O)CCCCOC(=O)C(CCCCCC)CCCCCCCC] | 85.34 | 0.119 | 96.2 |
| Sample 16 | 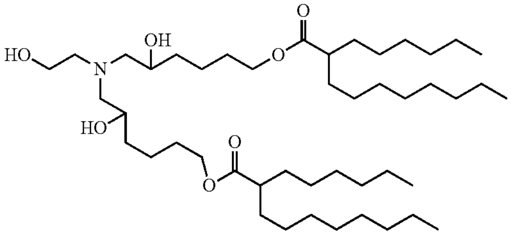 | 83.66 | 0.128 | 94.8 |
| Sample 17 | 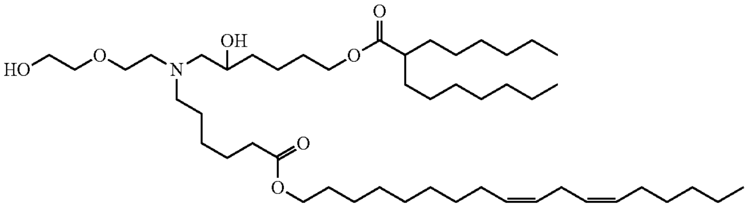 [SMILES: CCCCC/C=C\C/C=C\CCCCCCCCOC(=O)CCCCCN(CCOCCO)CC(O)CCCCOC(=O)C(CCCCCC)CCCCCCC] | 69.36 | 0.155 | 88.2 |
| Sample 18 | 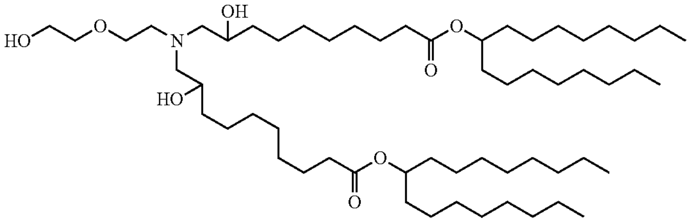 [SMILES: CCCCCCCCC(CCCCCCCC)OC(=O)CCCCCCCC(O)CN(CCOCCO)CC(O)CCCCCCCC(=O)OC(CCCCCCCC)CCCCCCCC] | 79.15 | 0.158 | 93.6 |
| Sample 19 | 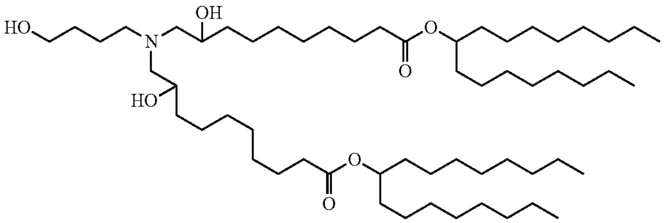 [SMILES: CCCCCCCCC(CCCCCCCC)OC(=O)CCCCCCCC(O)CN(CCCCO)CC(O)CCCCCCCC(=O)OC(CCCCCCCC)CCCCCCCC] | 81.48 | 0.161 | 91.8 |
| Sample 20 | 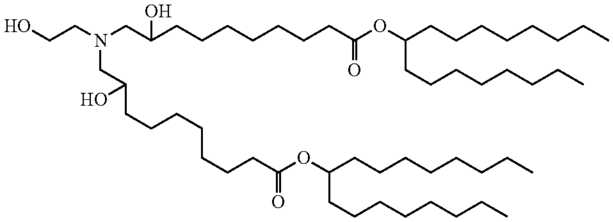 [SMILES: CCCCCCCCC(CCCCCCCC)OC(=O)CCCCCCCC(O)CN(CCO)CC(O)CCCCCCCC(=O)OC(CCCCCCCC)CCCCCCCC] | 99.12 | 0.164 | 93.2 |

TABLE 1-continued
| mRNA-LNP Sample | Structure of the cationic lipid | Size (nm) | PDI (particle dispersion index) | Encapsulation efficiency (%) |
|---|---|---|---|---|
| Sample 21 | 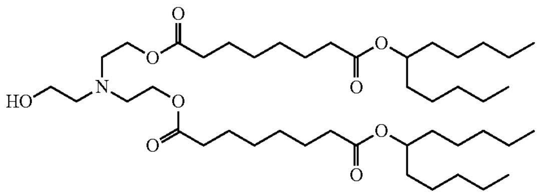 [SMILES: CCCCCC(CCCCC)OC(=O)CCCCCCC(=O)OCCN(CCO)CCOC(=O)CCCCCCC(=O)OC(CCCCC)CCCCC] | 81.87 | 0.147 | 81.1 |
| Sample 22 | 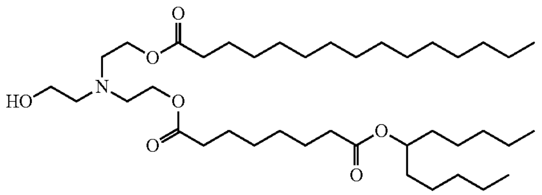 [SMILES: CCCCCCCCCCCCCCC(=O)OCCN(CCO)CCOC(=O)CCCCCCC(=O)OC(CCCCC)CCCCC] | 102.46 | 0.161 | 85.8 |
| Sample 23 | 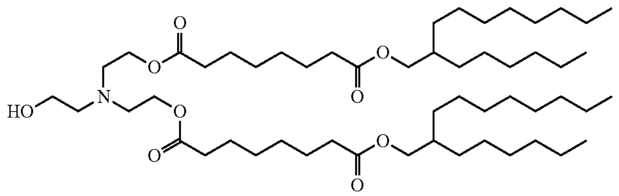 [SMILES: CCCCCCCCC(CCCCCC)COC(=O)CCCCCCC(=O)OCCN(CCO)CCOC(=O)CCCCCCC(=O)OCC(CCCCCC)CCCCCCCC] | 84.31 | 0.164 | 84.3 |
| Sample 24 | 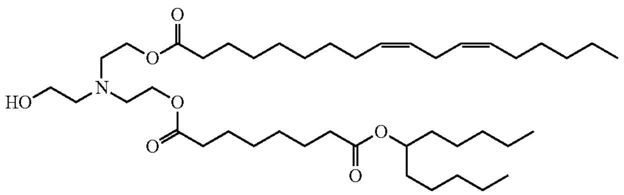 [SMILES: CCCCC/C=C\C/C=C\CCCCCCCC(=O)OCCN(CCO)CCOC(=O)CCCCCCC(=O)OC(CCCCC)CCCCC] | 81.56 | 0.181 | 92.7 |
| Sample 25 | 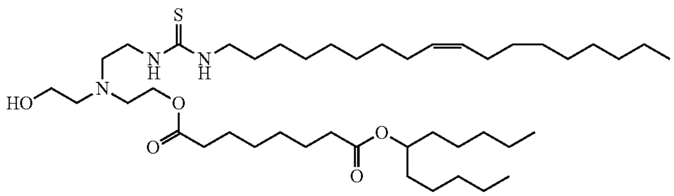 [SMILES: CCCCCCCC/C=C\CCCCCCCCNC(=S)NCCN(CCO)CCOC(=O)CCCCCCC(=O)OC(CCCCC)CCCCC] | 77.38 | 0.172 | 78.2 |
| Sample 26 | 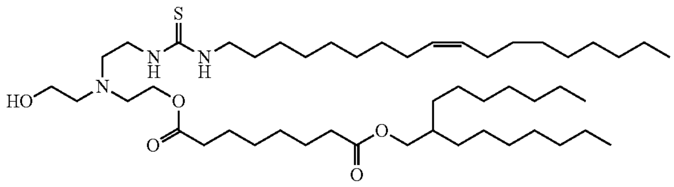 [SMILES: CCCCCCCC/C=C\CCCCCCCCNC(=S)NCCN(CCO)CCOC(=O)CCCCCCC(=O)OCC(CCCCCCC)CCCCCCC] | 65.12 | 0.157 | 76.6 |
| Sample 27 | 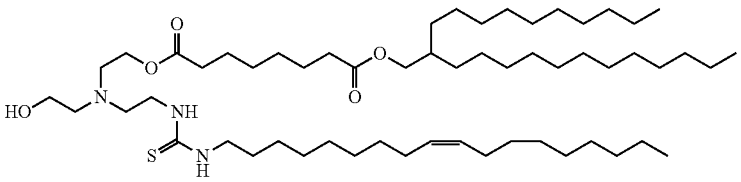 [SMILES: CCCCCCCC/C=C\CCCCCCCCNC(=S)NCCN(CCO)CCOC(=O)CCCCCCC(=O)OCC(CCCCCCCCCC)CCCCCCCCCCCC] | 70.43 | 0.163 | 73.9 |

TABLE 1-continued

| mRNA-LNP Sample | Structure of the cationic lipid | Size (nm) | PDI (particle dispersion index) | Encapsulation efficiency (%) |
|---|---|---|---|---|
| Sample 28 | 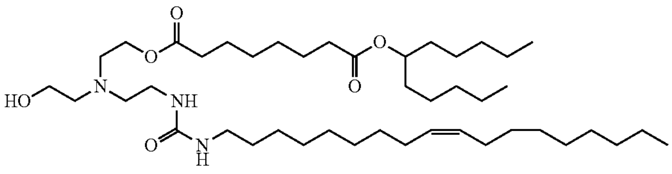 [SMILES: CCCCCCCC/C=C\CCCCCCCCNC(=O)NCCN(CCO)CCOC(=O)CCCCCCC(=O)OC(CCCCC)CCCCC] | 110.25 | 0.192 | 70.1 |
| Sample 29 | 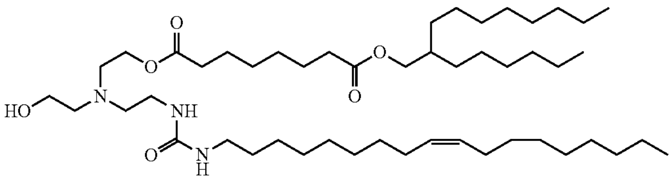 [SMILES: CCCCCCCC/C=C\CCCCCCCCNC(=O)NCCN(CCO)CCOC(=O)CCCCCCC(=O)OCC(CCCCCC)CCCCCCCC] | 67.12 | 0.187 | 71.7 |
| Sample 30 | 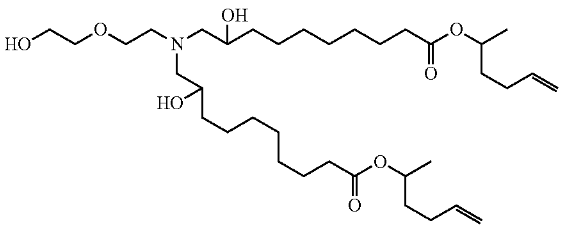 [SMILES: C=CCCC(C)OC(=O)CCCCCCCC(O)CN(CCOCCO)CC(O)CCCCCCCC(=O)OC(C)CCC=C] | 87.52 | 0.156 | 93.3 |
| Sample 31 | 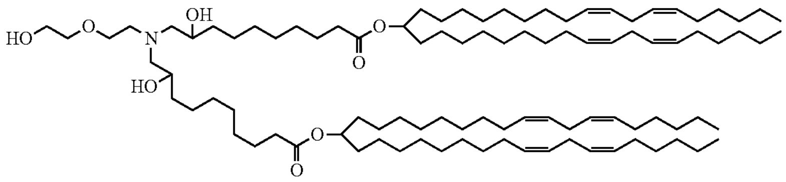 [SMILES: CCCCC/C=C\C/C=C\CCCCCCCCC(CCCCCCCC/C=C\C/C=C\CCCCC)OC(=O)CCCCCCCC(O)CN(CCOCCO)CC(O)CCCCCCCC(=O)OC(CCCCCCCC/C=C\C/C=C\CCCCC)CCCCCCCC/C=C\C/C=C\CCCCC] | 97.43 | 0.171 | 85.2 |

Experimental Example 2: Animal Experiments for LNPs Using the Samples Prepared in Experimental Example 1

Male ICR mice (6-8 weeks, Shanghai Jiesijie Experimental Animal Co., Ltd.) were housed under experimental conditions with a temperature of 22±2° C. and relative humidity of 45-75%, with a light/dark cycle of 12 hours. mRNA encoding luciferase was used as the reporter gene. Luciferase catalyzes fluorescein to produce biofluorescence, and the transfection efficiency of LNPs was determined by measuring the biofluorescence intensity per unit time. Taking luciferase mRNA (purchased from ApexBio Technology) as an Example, the mRNA-LNP samples 1-29 obtained above were compared with an existing commercially available compound MC3

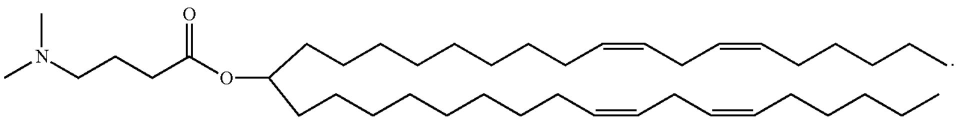 [SMILES: CCCCC/C=C\C/C=C\CCCCCCCCC(CCCCCCCC/C=C\C/C=C\CCCCC)OC(=O)CCCN(C)C]

The LNPs used as a positive control were formulated based on the well-known optimal PEG-lipid composition for MC3, with the molar ratio of Lipid (cationic lipid)/DSPC/Cholesterol/DMG-PEG (conjugated lipid) set at 50/10/38.5/1.5. A dose of 150 μg/kg mRNA was administered via intramuscular injection to two legs of one mouse in each group. At a specific time point, fluorescein (20 g/mL) was injected intraperitoneally into mice. After 5 minutes, the fluorescence intensity of each mouse were measured using a small animal in vivo imaging system. The final results were represented as the average fluorescence intensity. The experimental results of fluorescence intensity after intraperitoneal injection in mice are shown in Table 2.

TABLE 2

| mRNA-LNP Sample | Structure of the cationic lipid | Average intensity ($p/s/cm^2/sr$) |
|---|---|---|
| Comparative Sample MC3 | 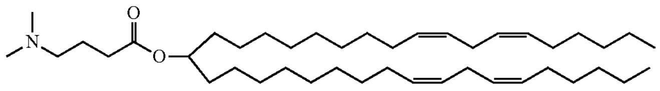 [SMILES: CCCCC/C=C\C/C=C\CCCCCCCCC(CCCCCCCC/C=C\C/C=C\CCCCC)OC(=O)CCCN(C)C] | 4.2E+5 |
| Sample 1 | 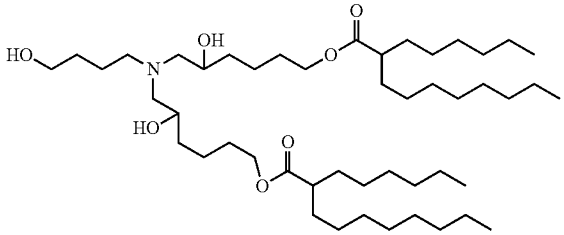 [SMILES: CCCCCCCCC(CCCCCC)C(=O)OCCCCC(O)CN(CCCCO)CC(O)CCCCOC(=O)C(CCCCCC)CCCCCCCC] | 6.32E+7 |
| Sample 2 | 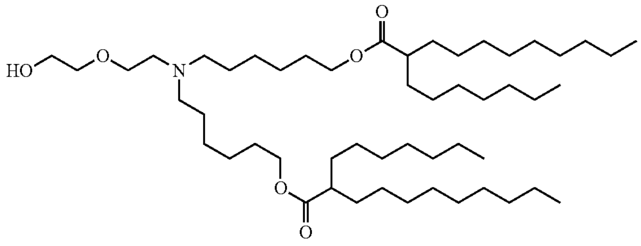 [SMILES: CCCCCCCCCC(CCCCCCC)C(=O)OCCCCCCN(CCCCCCOC(=O)C(CCCCCCC)CCCCCCCCC)CCOCCO] | 7.13E+6 |
| Sample 3 | 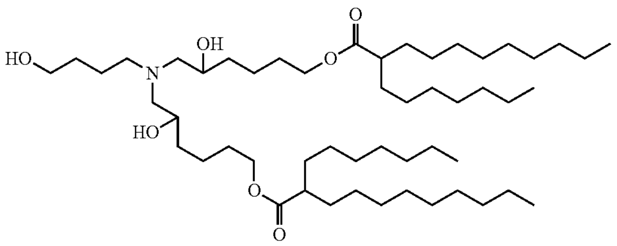 [SMILES: CCCCCCCCCC(CCCCCCC)C(=O)OCCCCC(O)CN(CCCCO)CC(O)CCCCOC(=O)C(CCCCCCC)CCCCCCCCC] | 6.08E+6 |
| Sample 4 | 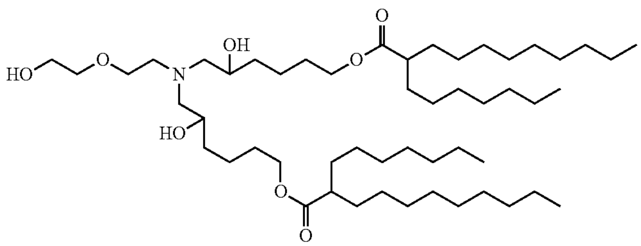 [SMILES: CCCCCCCCCC(CCCCCCC)C(=O)OCCCCC(O)CN(CCOCCO)CC(O)CCCCOC(=O)C(CCCCCCC)CCCCCCCCC] | 8.12E+6 |
| Sample 5 | 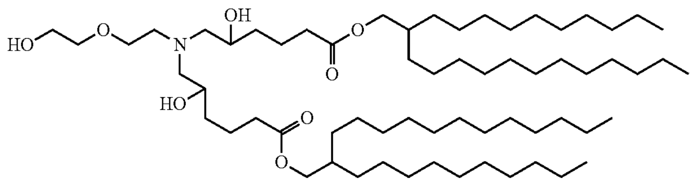 [SMILES: CCCCCCCCCCCCC(CCCCCCCCCC)COC(=O)CCCC(O)CN(CCOCCO)CC(O)CCCC(=O)OCC(CCCCCCCCCC)CCCCCCCCCCCC] | 7.47E+6 |

TABLE 2-continued
| mRNA-LNP Sample | Structure of the cationic lipid | Average intensity (p/s/cm$^2$/sr) |
|---|---|---|
| Sample 6 | 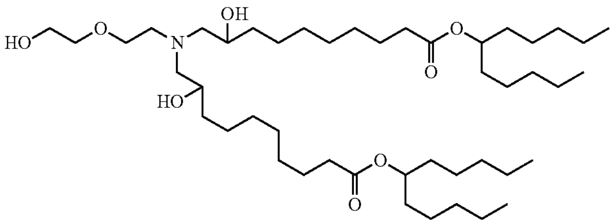 [SMILES: CCCCCC(CCCCC)OC(=O)CCCCCCCC(O)CN(CCOCCO)CC(O)CCCCCCCC(=O)OC(CCCCC)CCCCC] | 1.27E+7 |
| Sample 7 | 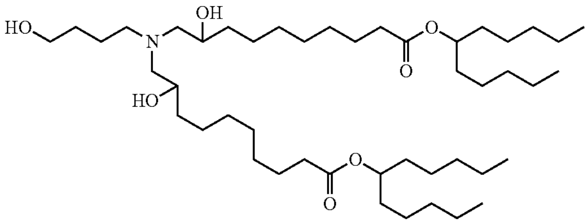 [SMILES: CCCCCC(CCCCC)OC(=O)CCCCCCCC(O)CN(CCCCO)CC(O)CCCCCCCC(=O)OC(CCCCC)CCCCC] | 8.18E+7 |
| Sample 8 | 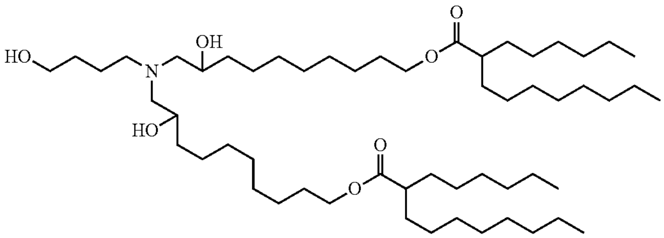 [SMILES: CCCCCCCCC(CCCCCC)C(=O)OCCCCCCCCC(O)CN(CCCCO)CC(O)CCCCCCCCOC(=O)C(CCCCCC)CCCCCCCC] | 7.2E+7 |
| Sample 9 | 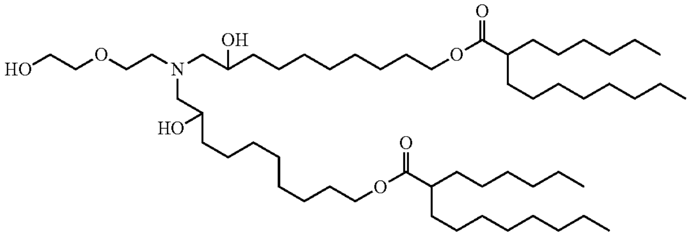 [SMILES: CCCCCCCCC(CCCCCC)C(=O)OCCCCCCCCC(O)CN(CCOCCO)CC(O)CCCCCCCCOC(=O)C(CCCCCC)CCCCCCCC] | 9.67E+7 |
| Sample 10 | 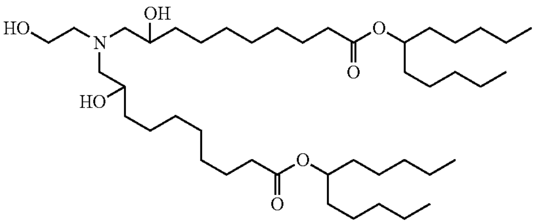 [SMILES: CCCCCC(CCCCC)OC(=O)CCCCCCCC(O)CN(CCO)CC(O)CCCCCCCC(=O)OC(CCCCC)CCCCC] | 8.59E+7 |
| Sample 11 | 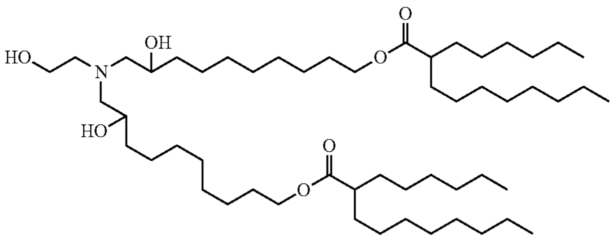 [SMILES: CCCCCCCCC(CCCCCC)C(=O)OCCCCCCCCC(O)CN(CCO)CC(O)CCCCCCCCOC(=O)C(CCCCCC)CCCCCCCC] | 7.16E+7 |

TABLE 2-continued
| mRNA-LNP Sample | Structure of the cationic lipid | Average intensity (p/s/cm²/sr) |
|---|---|---|
| Sample 12 | 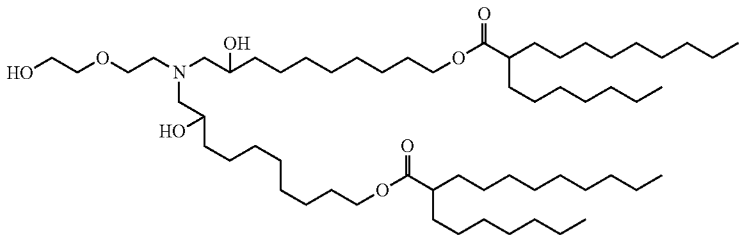 [SMILES: CCCCCCCCCC(CCCCCCC)C(=O)OCCCCCCCCC(O)CN(CCOCCO)CC(O)CCCCCCCCOC(=O)C(CCCCCCC)CCCCCCCCC] | 1.26E+7 |
| Sample 13 | 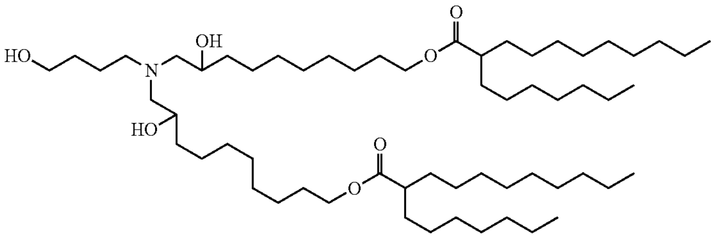 [SMILES: CCCCCCCCCC(CCCCCCC)C(=O)OCCCCCCCCC(O)CN(CCCCO)CC(O)CCCCCCCCOC(=O)C(CCCCCCC)CCCCCCCCC] | 1.77E+7 |
| Sample 14 | 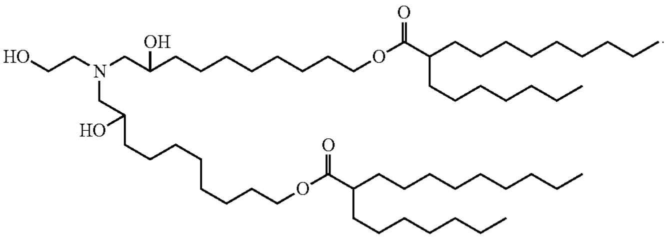 [SMILES: CCCCCCCCCC(CCCCCCC)C(=O)OCCCCCCCCC(O)CN(CCO)CC(O)CCCCCCCCOC(=O)C(CCCCCCC)CCCCCCCCC] | 2.71E+7 |
| Sample 15 | 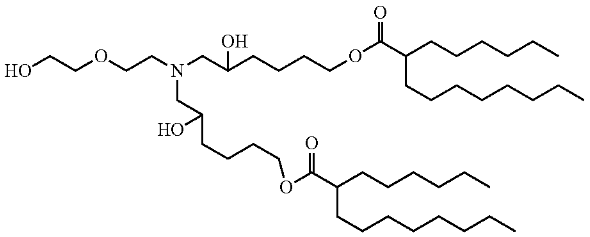 [SMILES: CCCCCCCCC(CCCCCC)C(=O)OCCCCC(O)CN(CCOCCO)CC(O)CCCCOC(=O)C(CCCCCC)CCCCCCCC] | 1.91E+8 |
| Sample 16 | 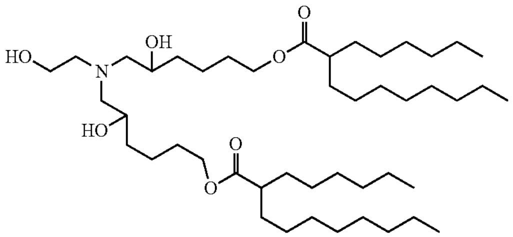 [SMILES: CCCCCCCCC(CCCCCC)C(=O)OCCCCC(O)CN(CCO)CC(O)CCCCOC(=O)C(CCCCCC)CCCCCCCC] | 8.18E+7 |
| Sample 17 | 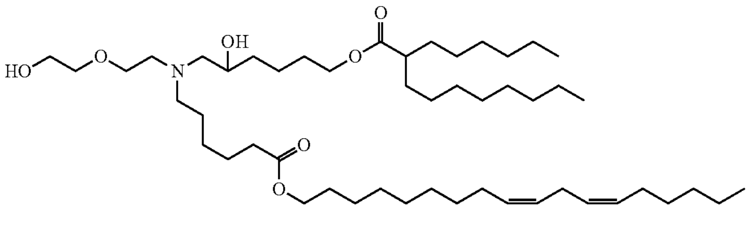 [SMILES: CCCCC/C=C\C/C=C\CCCCCCCCOC(=O)CCCCCN(CCOCCO)CC(O)CCCCOC(=O)C(CCCCCC)CCCCCCCC] | 1.26E+7 |

TABLE 2-continued
| mRNA-LNP Sample | Structure of the cationic lipid | Average intensity (p/s/cm$^2$/sr) |
|---|---|---|
| Sample 18 | 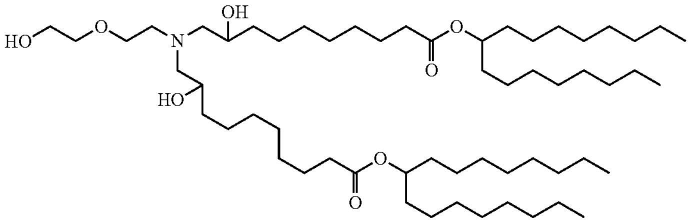 [SMILES: CCCCCCCCC(CCCCCCCC)OC(=O)CCCCCCCC(O)CN(CCOCCO)CC(O)CCCCCCCC(=O)OC(CCCCCCCC)CCCCCCCC] | 1.11E+7 |
| Sample 19 | 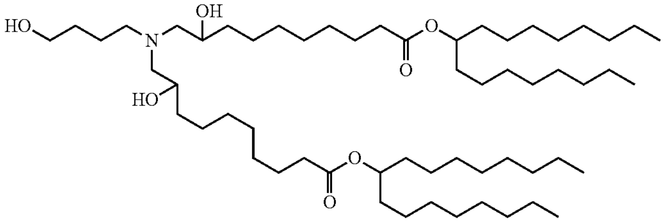 [SMILES: CCCCCCCCC(CCCCCCCC)OC(=O)CCCCCCCC(O)CN(CCCCO)CC(O)CCCCCCCC(=O)OC(CCCCCCCC)CCCCCCCC] | 8.58E+7 |
| Sample 20 | 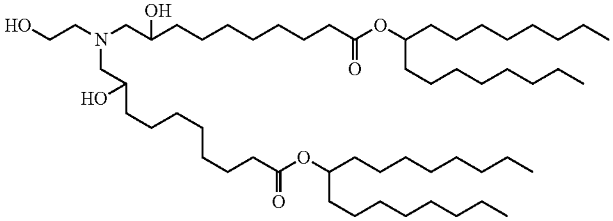 [SMILES: CCCCCCCCC(CCCCCCCC)OC(=O)CCCCCCCC(O)CN(CCO)CC(O)CCCCCCCC(=O)OC(CCCCCCCC)CCCCCCCC] | 1.69E+7 |
| Sample 21 | 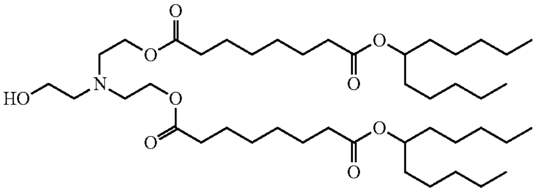 [SMILES: CCCCCC(CCCCC)OC(=O)CCCCCCC(=O)OCCN(CCO)CCOC(=O)CCCCCCC(=O)OC(CCCCC)CCCCC] | 8.39E+6 |
| Sample 22 | 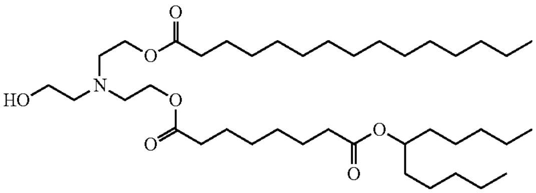 [SMILES: CCCCCCCCCCCCCCC(=O)OCCN(CCO)CCOC(=O)CCCCCCC(=O)OC(CCCCC)CCCCC] | 5.13E+6 |
| Sample 23 | 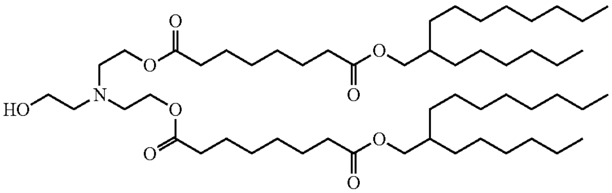 [SMILES: CCCCCCCCC(CCCCCC)COC(=O)CCCCCCC(=O)OCCN(CCO)CCOC(=O)CCCCCCC(=O)OCC(CCCCCC)CCCCCCCC] | 9.45E+6 |
| Sample 24 | 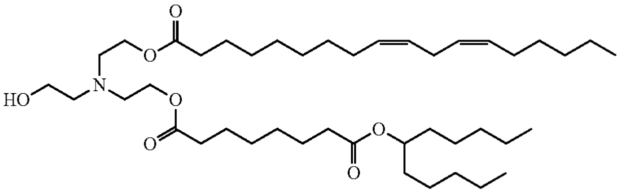 [SMILES: CCCCC/C=C\C/C=C\CCCCCCCC(=O)OCCN(CCO)CCOC(=O)CCCCCCC(=O)OC(CCCCC)CCCCC] | 6.5E+6 |

TABLE 2-continued
| mRNA-LNP Sample | Structure of the cationic lipid | Average intensity ($p/s/cm^2/sr$) |
|---|---|---|
| Sample 25 | 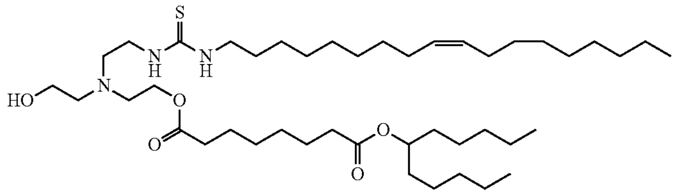 [SMILES: CCCCCCCC/C=C\CCCCCCCCNC(=S)NCCN(CCO)CCOC(=O)CCCCCCC(=O)OC(CCCCC)CCCCC] | 8.15E+7 |
| Sample 26 | 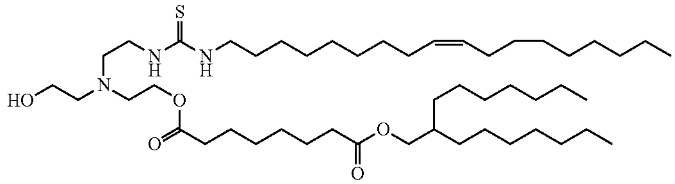 [SMILES: CCCCCCCC/C=C\CCCCCCCCNC(=S)NCCN(CCO)CCOC(=O)CCCCCCC(=O)OCC(CCCCCCC)CCCCCCC] | 1.2E+7 |
| Sample 27 | 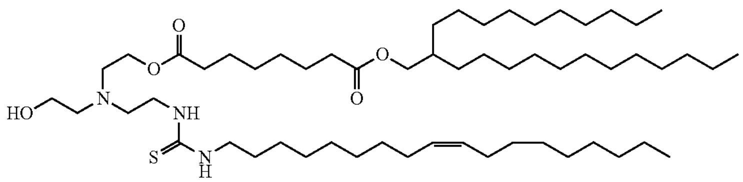 [SMILES: CCCCCCCC/C=C\CCCCCCCCNC(=S)NCCN(CCO)CCOC(=O)CCCCCCC(=O)OCC(CCCCCCCCCC)CCCCCCCCCCCC] | 7.1E+6 |
| Sample 28 | 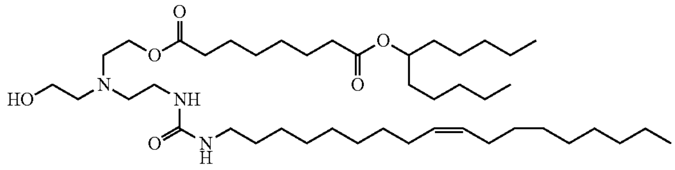 [SMILES: CCCCCCCC/C=C\CCCCCCCCNC(=O)NCCN(CCO)CCOC(=O)CCCCCCC(=O)OC(CCCCC)CCCCC] | 5.76E+6 |
| Sample 29 | 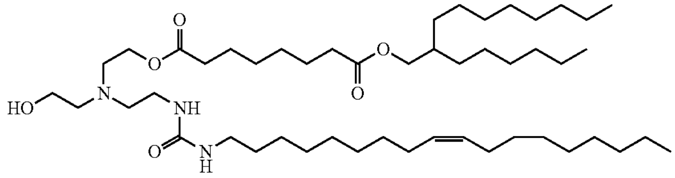 [SMILES: CCCCCCCC/C=C\CCCCCCCCNC(=O)NCCN(CCO)CCOC(=O)CCCCCCC(=O)OCC(CCCCCC)CCCCCCCC] | 6.55E+6 |
| Sample 30 | 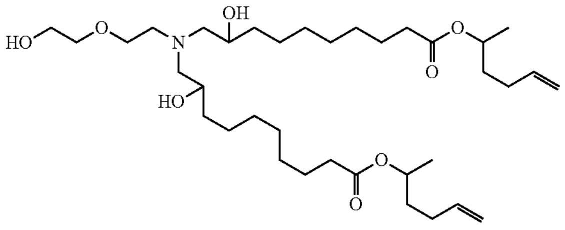 [SMILES: C=CCCC(C)OC(=O)CCCCCCCC(O)CN(CCOCCO)CC(O)CCCCCCCC(=O)OC(C)CCC=C] | 7.17E+7 |
| Sample 31 | 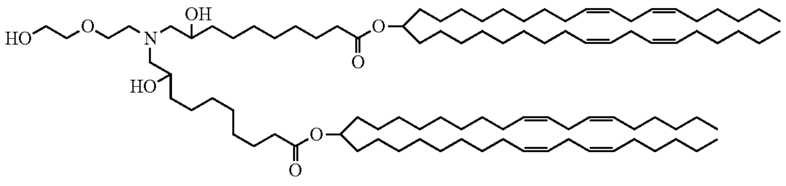 [SMILES: CCCCC/C=C\C/C=C\CCCCCCCCC(CCCCCCCC/C=C\C/C=C\CCCCC)OC(=O)CCCCCCCC(O)CN(CCOCCO)CC(O)CCCCCCCC(=O)OC(CCCCCCCC/C=C\C/C=C\CCCCC)CCCCCCCC/C=C\C/C=C\CCCCC] | 5.36E+7 |

The results showed that compared to the existing commercially available cationic lipid compound MC3, the cationic lipid compounds described in the present invention achieved significantly better biocompatibility and higher in vivo mRNA transfection efficiency.

Experimental Example 3: Structural Stability Experiment of LNPs Using the Sample Prepared in Experimental Example 1

Preparation and characterization of transmission electron microscopy samples (using sample 1 as an Example). 10 μL prepared sample 1 was dripped onto a copper mesh and deposited for 10 minutes, then the extra sample was absorbed and dried. The sample was then stained with uranyl acetate for 5 minutes, followed by blotting with filter paper to remove excess stain. After drying overnight, the morphology was examined using transmission electron microscopy (TEM).

As shown in the FIGURE, the LNPs described in the present invention can form stable nanostructure within a narrow size distribution range (small PDI), The particle size varies depending on the structure of the LNPs, ranging between 30 and 200 nm.

Experimental Example 4: Biocompatibility Verification Experiment Using the Samples Prepared in Experimental Example 1 and the Comparative Samples from Experimental Example 2

Cell viability was detected using CCK-8 (cell counting kit-8) assay kit. Hep3B cells in exponential growth phase (100 μL, cell density of $2\times10^4$ cells/mL) were seeded into a 96-well plate and incubated in a cell culture incubator for 24 hours. After removal of the culture medium from each well, 100 μL of fresh cell culture medium containing mRNA at 20 μg/mL encapsulated in LNPs was added, and the cells were co-incubated for 4 hours. Subsequently, the cell supernatant was removed, fresh cell culture medium was added, and the cells were further incubated for 20 hours. Then, the supernatant was removed, and 100 μL of fresh cell culture medium containing CCK-8 working solution (10 μL/mL) was added and incubated for 2 hours. Blank wells were set up with cell culture medium containing the working solution of CCK-8. The absorbance at 450 nm of each well was measured using a multimode microplate reader (no bubbles should be present in the plate during measurement). Cells without LNPs treatment were used as the control group, and their cell viability was set as 100%.

$$\text{Cell viability (\%)}=[A1-A0]/[A2-A0]\times100.$$

A1 represents the absorbance of the treating group, A0 represents the absorbance of the blank group, and A2 represents the absorbance of the control group. The experimental results are shown in Table 3.

TABLE 3

| mRNA LNP sample | Cell viability (%) |
|---|---|
| Comparative sample MC3 | 95% |
| Sample 1 | 96% |
| Sample 2 | 96% |
| Sample 3 | 97% |
| Sample 4 | 95% |

TABLE 3-continued

| mRNA LNP sample | Cell viability (%) |
|---|---|
| Sample 5 | 96% |
| Sample 6 | 95% |
| Sample 7 | 96% |
| Sample 8 | 95% |
| Sample 9 | 96% |
| Sample 10 | 95% |
| Sample 11 | 96% |
| Sample 12 | 95% |
| Sample 13 | 96% |
| Sample 14 | 97% |
| Sample 15 | 98% |
| Sample 16 | 96% |
| Sample 17 | 95% |
| Sample 18 | 96% |
| Sample 19 | 94% |
| Sample 20 | 97% |
| Sample 21 | 96% |
| Sample 22 | 97% |
| Sample 23 | 96% |
| Sample 24 | 97% |
| Sample 25 | 93% |
| Sample 26 | 91% |
| Sample 27 | 93% |
| Sample 28 | 92% |
| Sample 29 | 93% |
| Sample 30 | 97% |
| Sample 31 | 95% |

The experimental results showed that within the specified concentration range of LNPs, most cells had a viability no less than 95%, with no significant cytotoxicity observed.

Experimental Example 5: Low temperature Storage Effect Experiment of LNPs

Taking sample 1 as an Example, the LNPs prepared according to the formulation were stored at a low temperature of 4° C. At different time points (0 day, 6 days, 10 days, 15 days, 30 days, 45 days, 60 days, 90 days), samples were taken to characterize the particle size and PDI of mRNA-LNPs(mRNA loaded LNPs) using Malvern Zetasizer Nano ZS. The encapsulation efficiency of mRNA was determined using the Ribogreen RNA quantification kit (Thermo Fisher). The results are shown in Table 4.

TABLE 4

| Storage condition | Storage time (day) | Size (nm) | PDI | Encapsulation efficiency (%) |
|---|---|---|---|---|
| 4° C. | 0 | 85.3 | 0.112 | 96.1 |
| | 6 | 83.5 | 0.116 | 95.0 |
| | 10 | 84.4 | 0.113 | 95.3 |
| | 15 | 85.7 | 0.117 | 96.3 |
| | 30 | 82.4 | 0.113 | 95.3 |
| | 45 | 83.1 | 0.114 | 95.1 |

According to Table 4, the LNPs formed by the lipid molecules described in the present invention can be stored at low temperatures for a long time, which facilitates the transportation and preservation of the product.

In summary, the lipid compounds described in this invention feature hydroxyl group in the head structure, which confers hydrophilicity and capacities of fusing membrane. Meanwhile, the overall structure resembles a cone with a small head (nitrogen-containing moiety) and a large tail (long-chain alkane of hydrophobic moiety). The LNPs prepared using the cationic lipid compounds with the aforementioned optimal structure usually exhibit enhanced biocompatibility and higher in vivo mRNA transfection efficiency, achieving unexpected technical effects. Degradable ester bonds introduced into the hydrophobic tail part of the cationic lipid compounds described in this invention can be rapidly degraded by esterolytic enzymes in vivo. Compared with long-chain alkane in MC3, the introduction of ester bonds can alter the metabolic behavior of lipid molecules in vivo, thereby enhancing the biosafety of mRNA-LNPs. In terms of synthesis process, MC3 requires a five step reaction and involves highly dangerous Grignard reagents. Compared with MC3, the synthesis route described in this invention is simple and easy to implement, with inexpensive and readily available raw materials, which is conducive to industrial production. The LNPs prepared from the compounds described in this invention can be stored at low temperature for a long time, which facilitates the transportation and preservation of the product. Therefore, the novel cationic lipid compounds described in this invention have promising application prospects.

The basic principles, main features, and advantages of the present invention are shown and described herein. Those skilled in the art should understand that the aforementioned embodiments do not limit the present invention in any form, and all technical solutions obtained by means of equivalent substitution or equivalent transformation fall within the scope of protection of the present invention.

The invention claimed is:

1. A cationic lipid compound selected from the group consisting of:

H-6

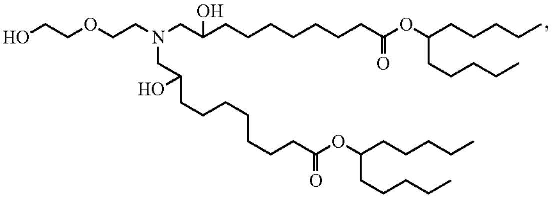

,

H-7

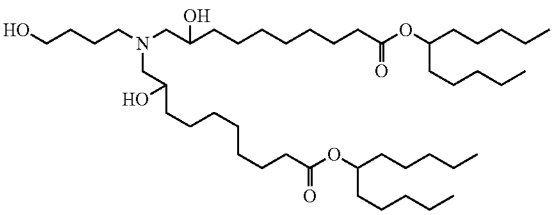

H-8

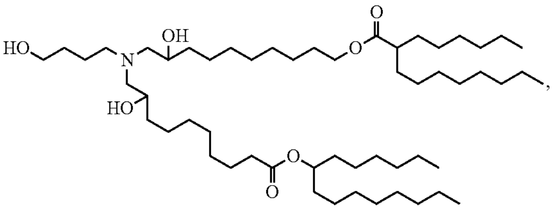

,

H-9

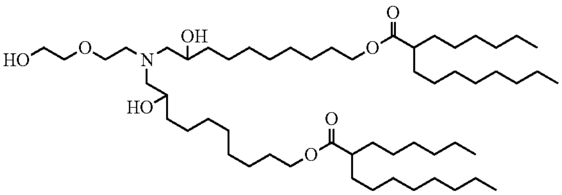

-continued

H-10

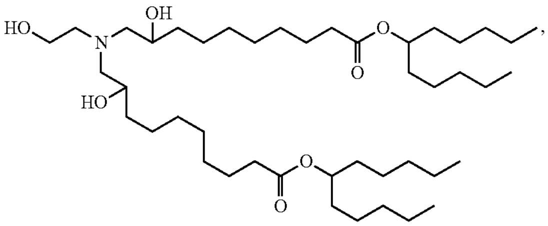

,

H-11

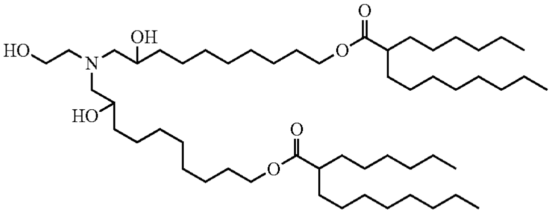

H-12

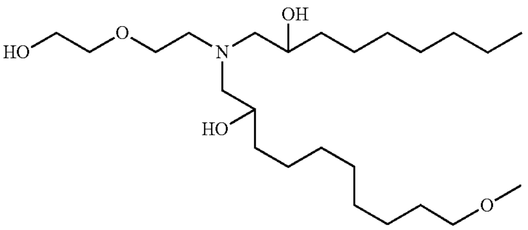

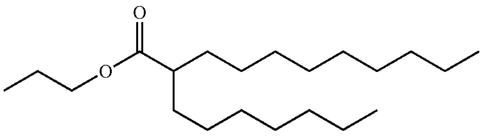

,

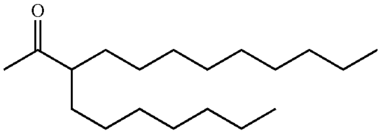

H-13

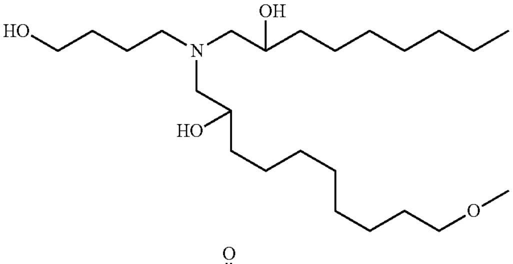

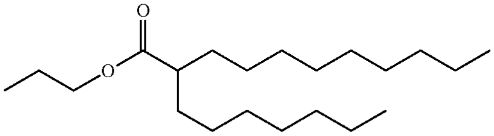

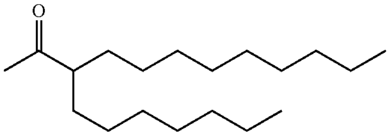

-continued
H-14
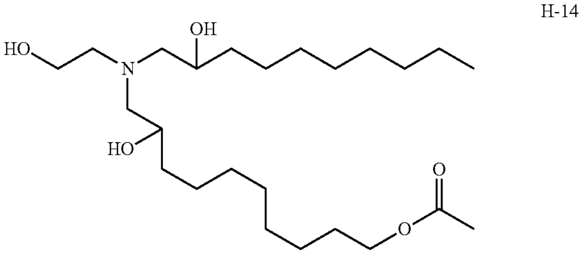
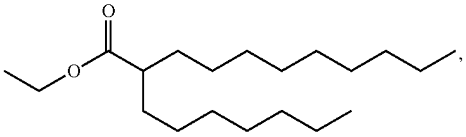
,
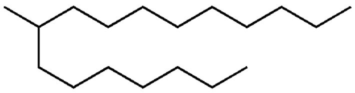
H-15
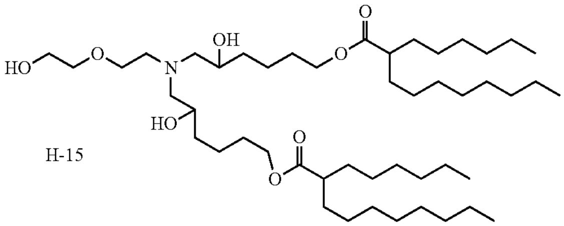
H-15
H-16
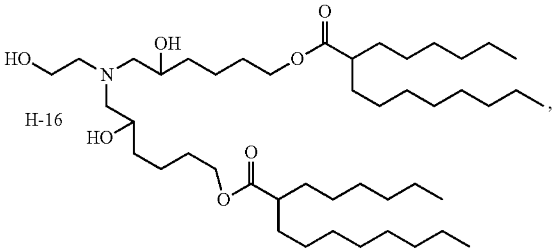
H-16
,
-continued
H-18
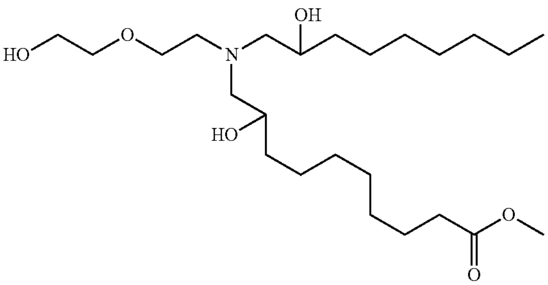
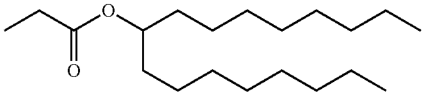
,
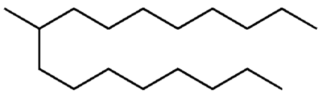
H-19
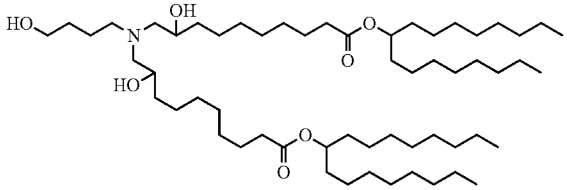
H-20
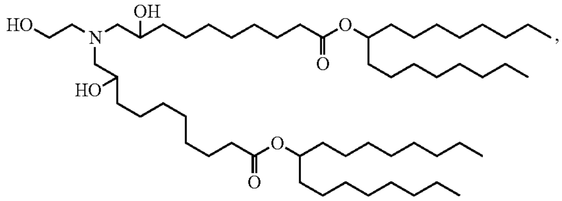
,
or a stereoisomer thereof, tautomer thereof, or pharmaceutically acceptable salt thereof.
2. A cationic lipid compound selected from the group consisting of:
H-30
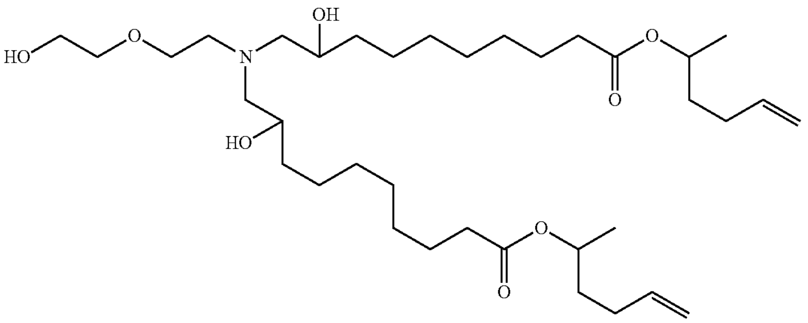

-continued

H-31

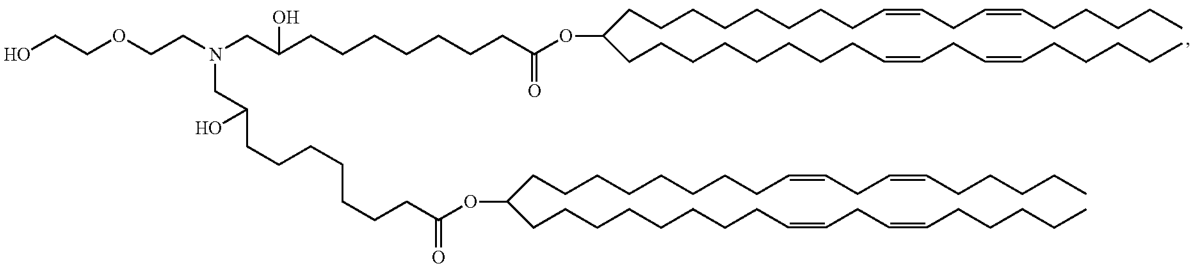

, or a stereoisomer thereof, tautomer thereof, or pharmaceutically acceptable salt thereof.

3. A method for preparation of a composition, which comprises: using the cationic lipid compound of claim 1, a stereoisomer thereof, tautomer thereof, or pharmaceutically acceptable salt thereof as the cationic lipid compound to prepare the composition.

4. The method of claim 3, wherein the composition further comprises: a carrier, a loaded drug, a pharmaceutical adjuvant.

5. The method of claim 4, wherein the carrier is LNPs, the average size of the LNPs ranges from 30-200 nm, and the polydispersity index of the LNPs is ≤0.5.

6. The method of claim 5, wherein the carrier comprises one or more ionizable lipid compounds.

7. The method of claim 6, wherein the carrier further comprises: helper lipids, and the molar ratio of cationic lipid compounds to helper lipids ranges from 0.5:1-10:1; the helper lipid comprises one or more of phosphatidylcholine, phosphatidylethanolamine, sphingomyelin, sterol and derivative thereof, ceramide, and charged lipid.

8. The method of claim 6 for the composition comprising the cationic lipid compounds, wherein the carrier further comprises structural lipids or polymer-conjugated lipids.

9. The method of claim 8, wherein the carrier further comprises: structural lipids, and the molar ratio of the cationic lipid compounds to structural lipids ranges from 0.5:1 to 5:1.

10. The method of claim 7, wherein the carrier further comprises: polymer-conjugated lipids, and the molar ratio of the cationic lipid compounds to polymer-conjugated lipids ranges from 20:1-250:1; the polymer-conjugated lipid is PEGylated lipid.

11. The method of claim 4, wherein the loaded drug comprises one or more of nucleic acid molecules, small molecule compounds, peptides, or proteins.

12. The method of claim 4, wherein the pharmaceutical adjuvant comprises one or more of diluents, stabilizers, preservatives, or lyoprotectants.

* * * * *